(12) United States Patent
Kebebew et al.

(10) Patent No.: US 9,428,813 B2
(45) Date of Patent: Aug. 30, 2016

(54) DNA METHYLATION ANALYSIS FOR THE DIAGNOSIS, PROGNOSIS AND TREATMENT OF ADRENAL NEOPLASMS

(71) Applicant: The United States of America, as Represented by the Secretary, Department of Health and Human Services, Washington, DC (US)

(72) Inventors: Electron Kebebew, Rockville, MD (US); Nesrin S. Rechache, Rockville, MD (US); Paul S. Meltzer, Rockville, MD (US); Yong-hong Wang, Clarksburg, MD (US)

(73) Assignee: The United States of America, as Represented by the Secretary, Dept. of Health & Human Services, Washington, DC (US)

( * ) Notice: Subject to any disclaimer, the term of this patent is extended or adjusted under 35 U.S.C. 154(b) by 0 days.

(21) Appl. No.: 14/384,583

(22) PCT Filed: Mar. 12, 2013

(86) PCT No.: PCT/US2013/030347
§ 371 (c)(1),
(2) Date: Sep. 11, 2014

(87) PCT Pub. No.: WO2013/148147
PCT Pub. Date: Oct. 3, 2013

(65) Prior Publication Data
US 2015/0119350 A1    Apr. 30, 2015

Related U.S. Application Data

(60) Provisional application No. 61/615,869, filed on Mar. 26, 2012.

(51) Int. Cl.
C12Q 1/68 (2006.01)

(52) U.S. Cl.
CPC ....... *C12Q 1/6886* (2013.01); *C12Q 2600/118* (2013.01); *C12Q 2600/154* (2013.01); *C12Q 2600/16* (2013.01)

(58) Field of Classification Search
CPC ............ C12Q 1/6886; C12Q 2600/16; C12Q 2600/154; C12Q 2600/118
USPC .................................................. 514/43; 506/3
See application file for complete search history.

(56) References Cited

U.S. PATENT DOCUMENTS

| | | |
|---|---|---|
| 2006/0003322 A1 | 1/2006 | Bentwich |
| 2007/0172844 A1 | 7/2007 | Lancaster et al. |
| 2009/0105167 A1 | 4/2009 | Potti et al. |
| 2009/0181393 A1 | 7/2009 | Mulligan et al. |
| 2011/0098189 A1 | 4/2011 | Lapointe et al. |
| 2011/0236903 A1 | 9/2011 | McClelland et al. |
| 2011/0320390 A1 | 12/2011 | Kuznetsov et al. |
| 2012/0219559 A1 | 8/2012 | Chen |

FOREIGN PATENT DOCUMENTS

| | | |
|---|---|---|
| CA | 2612021 A1 | 12/2006 |
| CA | 2662508 A1 | 7/2008 |
| CA | 2692973 A1 | 1/2009 |
| CA | 2713909 A1 | 8/2009 |
| CA | 2754610 A1 | 9/2010 |
| WO | WO 2007/030531 | 3/2007 |
| WO | WO 2007/102812 | 9/2007 |
| WO | WO 2010/070637 | 6/2010 |
| WO | WO 2012/115885 | 8/2012 |

OTHER PUBLICATIONS

Gicquel et al. Structural and Functional Abnormalities at 11p15 Are Associated with the Malignant Phenotype in Sporadic Adrenocortical Tumors: Study on a Series of 82 Tumors. J Clin Endocrinol Metab 82:2559-2565, 1997.*
Bibikova et al. High density DNA methylation array with single CpG site resolution. Genomics 98 (2011) 288-295.*
Fernandez-Ranvier et al., "Identification of Biomarkers of Adrenocortical Carcinoma Using Genomewide Gene Expression Profiling," *Archives of Surgery*, vol. 143, No. 9, Sep. 15, 2008.
Fonseca et al., "Comprehensive DNA methylation analysis of benign and malignant adrenocortical tumors," *Genes, Chromosomes and Cancer*, vol. 51, No. 10, Oct. 1, 2012.
Gao et al., "Association of H19 Promoter Methylation with the Expression of H19 and IGF-II Genes in Adrenocortical Tumors," *Journal of Clinical Endocrinology & Metabolism*, vol. 87, No. 3, Mar. 1, 2002.
International Search Report and Written Opinion issued Jun. 5, 2013, by the European Patent Office, for PCT Patent Application No. PCT/US2013/030347, filed Mar. 12, 2013.
Suh et al., "Antineoplastic effects of Decitabine, an Inhibitor of DNA Promoter Methylation, in Adrenocortical Carcinoma Cells," *Arch. Surg.* Mar. 2010: 145(3): 226-232.
Wong, "Ubiquitous Aberrant RASSF1A Promoter Methylation in Childhood Neoplasial," *Clinical Cancer Research*, vol. 10, No. 3, Feb. 1, 2004.

* cited by examiner

Primary Examiner — Clinton Brooks
Assistant Examiner — Yih-Horng Shiao
(74) Attorney, Agent, or Firm — Klarquist Sparkman, LLP

(57) ABSTRACT

Disclosed herein are methods for detecting, diagnosing and/or prognosing a malignant adrenocortical tumor. Also disclosed are methods of treating a malignant adrenocortical tumor, such as ACC. In some examples, the method of diagnosing and/or prognosing includes obtaining a sample comprising genomic DNA from a subject at risk of acquiring or suspected to have an adrenocortical tumor; isolating genomic DNA from the sample; and measuring the level of one or more methylated genomic CpG dinucleotide sequences in one or more of the adrenocortical genomic targets in the sample, wherein an increase in the level of methylation of the one or more genomic CpG dinucleotide sequences in the sample compared to a control indicates a malignant adrenocortical tumor.

16 Claims, 18 Drawing Sheets

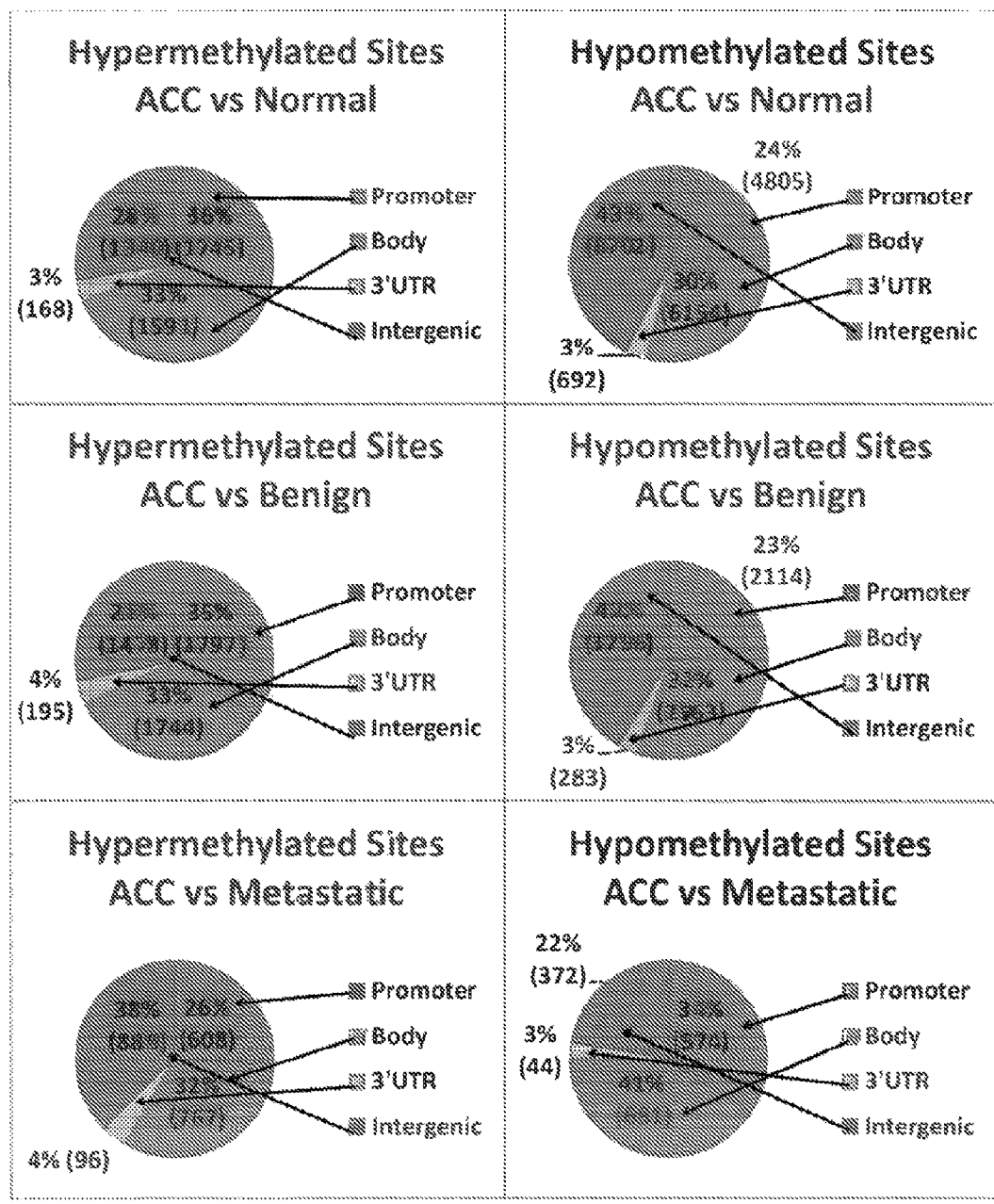

DNA METHYLATION ANALYSIS FOR THE DIAGNOSIS, PROGNOSIS AND TREATMENT OF ADRENAL NEOPLASMS

CROSS REFERENCE TO RELATED APPLICATIONS

This is the U.S. National Stage of International Application No. PCT/US2013/030347, filed Mar. 12, 2013, which was published in English under PCT Article 21(2), which in turn claims the benefit of U.S. Provisional Application No. 61/615,869, filed on Mar. 26, 2012, which is incorporated herein by reference in its entirety.

FIELD

The present disclosure relates to conditions characterized by differentially methylated genomic CpG dinucleotide sequences. Further, it relates to diagnostic and prognostic methods that exploit the presence of genomic DNA sequences that exhibit altered methylation patterns, including altered CpG methylation patterns, for the diagnosis and prognosis of adrenocortical neoplasms.

BACKGROUND

Adrenal neoplasms include benign and malignant tumors of the adrenal gland. Adrenocortical adenomas are benign tumors of the adrenal cortex and are extremely common. In contrast, malignant adrenal tumors such as adrenocortical carcinomas (ACC) are rare malignancies that have an annual incidence of 0.5-2 cases per million.

ACC has a very poor prognosis with only a 15-45% survival at 5 years. The incidence of ACC is highest in the fifth and sixth decade of life, however a high incidence of ACC has been found in children in southern Brazil which was associated with a germline mutation in p53. Over half of ACC are considered functional (producers of steroid hormones) when excess hormones are produced and Cushing's syndrome is the most common clinical manifestation. The majority of ACC cases are sporadic, however, several genetic syndromes have been associated with ACC including Beckwith-Wiedemann and Li-Fraumeni syndromes, Carney complex, familial adenomatous polyposis, congenital adrenal hyperplasia, and multiple endocrine neoplasia type 1. Without the clear presentation of local invasion or distant metastasis, the diagnosis and pathological distinction between benign and malignant adrenocortical tumors can be difficult. Histologically, the 9 Weiss parameters (0-9 score) are commonly used for diagnosis, with Weiss scores of ≤2 being considered benign and ≥3 malignant. However, given the subjective nature of the Weiss histologic features, particularly in regards to scores of 2-3 that are of indeterminate classification and the most common group of adrenocortical tumors, there is a need for better diagnostic tools for assessing adrenocortical tumors, preoperatively and as an adjunct to routine histopathology.

SUMMARY

Described herein is the surprising finding that methylation profile differences accurately distinguish between malignant and benign adrenocortical tumors. Prior to the present disclosure, the understanding of the molecular events involved in adrenocortical carcinogenesis remained to be elucidated. The inventors established a methylation profile for normal, benign, primary malignant and metastatic malignant adrenocortical tissue samples to determine if epigenetic differences exist in adrenocortical neoplasms. Further, the inventors investigated whether this approach could be used for classification of adrenocortical neoplasms, as well as, to serve to identify possible therapeutic targets. The present disclosure not only characterizes DNA methylation changes associated with adrenocortical neoplasms, such as ACC, but indicates that differential DNA methylation status may serve as diagnostic markers and/or targets for therapy for ACC.

Based upon these findings, disclosed herein are methods for detecting, diagnosing, prognosing and/or treating an adrenocortical tumor, such as a malignant adrenocortical tumor. In some embodiments, a method of diagnosing and/or prognosing an adrenocortical tumor includes obtaining a sample comprising genomic DNA from a subject at risk of acquiring or suspected to have an adrenocortical tumor and measuring the level of one or more methylated genomic CpG dinucleotide sequences in one or more genomic targets, such as one or more malignant adrenocortical tumor-related molecules (e.g., KCTD12, KIRREL, SYNGR1, NTNG2, GATA6, TP53, β-catenin (CTNNB1), IGF2, H19, IGF1R, AKT1, IL13RA2, HTR2B, CCNB2, RARRES2, SLC16A9 and/or molecules listed in Tables 2-5), wherein an increase in the level of methylation of the one or more genomic CpG dinucleotide sequences in the sample compared to a control indicates a malignant adrenocortical tumor. In some examples, the method further includes isolating genomic DNA from the sample prior to measuring the level of one or more methylated genomic CpG dinucleotide sequences. In some examples, the method includes contacting the isolated genomic DNA with sodium bisulfite prior to measuring the level of one or more methylated genomic CpG dinucleotide sequences thereby converting an unmethylated cytosine to a uracil in the genomic DNA while a methylated cytosine in the genomic DNA is resistant to the sodium bisulfite and remains unchanged prior to measuring the level of one or more methylated genomic CpG dinucleotide sequences.

Also disclosed are methods for detecting an adrenocortical cell proliferative disorder, such as a malignant adrenocortical cell proliferative disorder. In some embodiments, a method for detecting a malignant adrenocortical cell proliferative disorder in a subject includes contacting at least one malignant adrenocortical tumor-related nucleic acid in a sample from the subject with a reagent that detects methylation, wherein the one or more malignant adrenocortical tumor-related nucleic acid comprises KCTD12, KIRREL, SYNGR1, NTNG2 GATA6, TP53, β-catenin (CTNNB1), IGF2, H19, IGF1R, AKT1, RARRES2, SLC16A9, IL13RA2, HTR2B, CCNB2, and/or one or more nucleic acids listed in Tables 2-5; and detecting methylation of the at least one malignant adrenocortical tumor-related nucleic acid, wherein an increase in methylation of the at least one malignant adrenocortical tumor-related nucleic acid as compared with the level of methylation of the corresponding nucleic acid in a control sample, is indicative of a malignant adrenocortical cell proliferative disorder.

Further disclosed are methods of treating a malignant adrenocortical tumor, such a primary malignant or a metastatic adrenocortical tumor. In some embodiments, the method includes administering to a subject with a malignant adrenocortical tumor an effective amount of a demethylating agent that alters the activity and/or expression of one or more malignant adrenocortical tumor molecules listed in Tables 2-5 (which was indicated to be hypermethylated and/or down-regulated), thereby treating the malignant adrenocortical tumor. In some embodiments, the method of treatment further includes selecting a subject with a malignant adrenocortical tumor prior to administering the treatment. For example, selecting a subject with a malignant adrenocortical tumor includes detecting methylation and mRNA expression of one or more malignant adrenocortical tumor molecules disclosed herein and including one or more listed in Tables 2-5, whereby an increase in methylation and a decrease in mRNA expression of the one or more malignant adrenocortical tumor molecules indicate the subject has a malignant adrenocortical tumor.

In any of the provided methods, the sample may comprise adrenocortical tissue or biological fluid (such as for instance blood, a fraction of blood, saliva, or urine).

In any of the provided methods, the adrenocortical tumor is ACC.

The foregoing and other features and advantages of the disclosure will become more apparent from the following detailed description, which proceeds with reference to the accompanying figures.

BRIEF DESCRIPTION OF THE DRAWINGS

(FIG. 1A) Normal tissue samples compared to benign tissue samples have the least number of differences in methylation and they are predominantly hypermethylated (104 total, 34 hypomethylated and 70 hypermethylated). Primary and metastatic ACC samples compared to normal tissue samples have the greatest number of differences in methylation and they are both predominantly hypomethylated (primary ACC vs. normal 24,229 total, 19,689 hypomethylated 4,540 hypermethylated and metastatic vs. normal samples 21,736 total, 17,569 hypomethylated and 4,167 hypermethylated). (FIG. 1B) Primary and metastatic ACC samples compared to benign tissue samples have the next largest differences in methylation and they are also both predominantly hypomethylated (primary ACC vs. benign 13,727 total, 8824 hypomethylated and 4903 hypermethylated and metastatic vs. benign 11,849 total, 7650 hypomethylated and 4199 hypermethylated). Primary ACC samples compared to metastatic samples however have only 3,799 differentially methylated sites and they are predominantly hypermethylated (1,556 hypomethylated and 2,243 hypermethylated).

FIGS. 4C and 4D include a series of pie charts illustrating methylation differences by functional genomics (promoter, body, 3'UTR and intergenic regions) stratified by hypermethylation or hypomethylation status.

DETAILED DESCRIPTION OF SEVERAL EMBODIMENTS

I. Terms

Figure 1A:
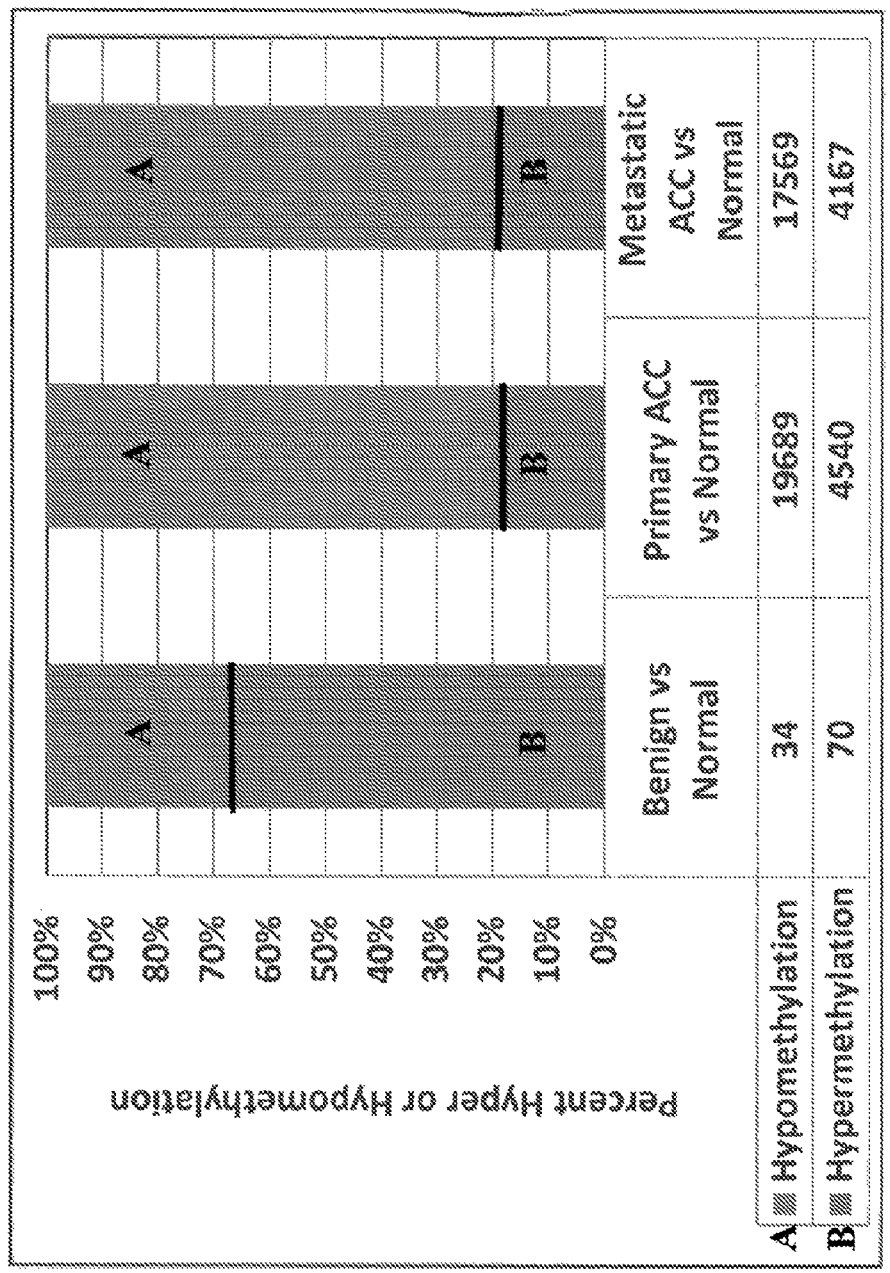
FIGS. 1A and 1B are bar graphs showing differential methylation across all tissue comparisons.

Unless otherwise noted, technical terms are used according to conventional usage. Definitions of common terms in molecular biology may be found in Benjamin Lewin, *Genes IX*, published by Jones and Bartlett Publishers, 2007 (ISBN 0763740632); Kendrew et al. (eds.), *The Encyclopedia of Molecular Biology*, published by Blackwell Science Inc., 1998; and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, intratumoral and intravenous), oral, intraductal, sublingual, rectal, transdermal, intranasal, and inhalation routes.

Adrenocortical carcinoma (ACC): A rare but aggressive malignancy of the adrenal cortex. Adrenocortical carcinoma (also called "adrenal carcinoma) is cancer that affects 1 to 2 people per million per year and accounts for 0.02-0.2% of all cancer deaths. Approximately half of all patients have metastatic disease at the time of diagnosis resulting in an average five-year survival of less than 10%. Currently there is limited knowledge regarding the initiation and pathophysiology of ACC.

Metastatic disease or local invasion is the only absolute indicator of malignancy. Masses without these features are assessed preoperatively based on size, and imaging characteristics, although the findings of these studies often are unable to definitively categorize the tumor as benign or malignant. After resection, tumor pathology is assessed based on several histologic criteria including cell morphology, cellular proliferation, and tumor invasiveness (Weiss criteria). The only curative treatment is complete surgical excision of the tumor, which can be performed even in the case of invasion into large blood vessels, such as the renal vein or inferior vena cava. A large percentage of patients are not surgical candidates. Radiation therapy and radiofrequency ablation may be used for palliation in patients who are not surgical candidates.

Chemotherapy regimens typically include the drug mitotane, an inhibitor of steroid synthesis which is toxic to cells of the adrenal cortex, as well as standard cytotoxic drugs. One widely used regimen consists of cisplatin, doxorubicin, etoposide, and mitotane. The endocrine cell toxin streptozotocin has also been included in some treatment protocols. Chemotherapy may be given to patients with unresectable disease, to shrink the tumor prior to surgery (neoadjuvant chemotherapy), or in an attempt to eliminate microscopic residual disease after surgery (adjuvant chemotherapy). Hormonal therapy with steroid synthesis inhibitors such as aminoglutethimide may be used in a palliative manner to reduce the symptoms of hormonal syndromes.

Agent: Any protein, nucleic acid molecule (including chemically modified nucleic acids), compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject, including inhibiting or treating a malignant adrenocortical tumor, such as inhibiting or treating ACC). For example, a "therapeutic agent" is a chemical compound, small molecule, or other composition, such as an antisense compound, antibody, protease inhibitor, hormone, chemokine or cytokine, capable of inducing a desired therapeutic or prophylactic effect when properly administered to a subject. In some examples, the therapeutic agent includes a demethylating agent.

Amplification: Amplification of a nucleic acid molecule (such as a DNA or RNA molecule) refers to use of a technique that increases the number of copies of a nucleic acid molecule in a sample.

In one example, amplification is multiple strand displacement amplification, such as described in U.S. Pat. No. 6,617,137.

Another example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid molecule. This cycle can be repeated multiple times.

The product of amplification can be characterized by such techniques as electrophoresis, restriction endonuclease cleavage patterns, oligonucleotide hybridization, and/or nucleic acid sequencing.

Other examples of in vitro amplification techniques include quantitative real-time PCR; reverse transcriptase PCR; real-time reverse transcriptase PCR; nested PCR; transcription-free isothermal amplification (see U.S. Pat. No. 6,033,881), repair chain reaction amplification (see PCT publication No. WO 90/01069); ligase chain reaction amplification (see published European Patent No. EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

Array: An arrangement of molecules, particularly biological macromolecules (such as polypeptides or nucleic acids, for example molecules that can detect methylation of a disclosed malignant adrenocortical tumor-associated molecule, such as a KCTD12, KIRREL, SYNGR1, NTNG2, IL13RA2, HTR2B, CCNB2, RARRES2, SLC16A9 gene or a gene listed in Tables 2-4) or cell or tissue samples, in addressable locations on or in a substrate. The array may be regular (arranged in uniform rows and columns, for instance) or irregular. The number of addressable locations on the array can vary, for example from a few (such as three) to more than 50, 100, 200, 500, 1000, 10,000, or more. A "microarray" is an array that is miniaturized so as to require or be aided by microscopic examination for evaluation or analysis.

Within an array, each arrayed sample (feature) is addressable, in that its location can be reliably and consistently determined within the at least two dimensions of the array. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (e.g., in radially distributed lines, spiral lines, or ordered clusters). Addressable arrays usually are computer readable, in that a computer can be programmed to correlate a particular address on the array with information about the sample at that position (e.g., hybridization or binding data, including for instance signal intensity). In some examples of computer readable formats, the individual features in the array are arranged regularly, for instance in a Cartesian grid pattern, which can be correlated to address information by a computer.

The sample application location on an array (the "feature") may assume many different shapes. Thus, though the term "spot" may be used herein, it refers generally to a localized placement of molecules or tissue or cells, and is not limited to a round or substantially round region. For instance, substantially square regions of application can be used with arrays encompassed herein, as can be regions that are, for example substantially rectangular, triangular, oval, irregular, or another shape.

In certain example arrays, one or more features will occur on the array a plurality of times (e.g., twice) to provide internal controls.

β-catenin (CTNNB1): Catenin (cadherin-associated protein), beta 1 (also known as OK/SW-cl.35, CTNNB), GeneID: 1499 (available on-line on the World Wide Web at ncbi.nlm.nih.gov/gene/1499, the entire content of which is incorporated by reference as of Mar. 26, 2012). In one example, a β-catenin nucleic acid molecule includes a potentially methylated cytosine within a CpG site. In one example, a β-catenin nucleic acid includes the sequence provided in Table 3 wherein the bracketed CG is a potentially methylated CpG site.

Binding or stable binding: An oligonucleotide binds or stably binds to a target nucleic acid (such as a malignant adrenocortical tumor molecule, e.g., KCTD12, KIRREL, SYNGR1, NTNG2, IL13RA2, HTR2B, CCNB2, RARRES2, or SLC16A9 nucleic acid) if a sufficient amount of the oligonucleotide forms base pairs or is hybridized to its target nucleic acid, to permit detection of that binding. Binding can be detected by either physical or functional properties of the target: oligonucleotide complex. Binding between a target and an oligonucleotide can be detected by any procedure known to one skilled in the art, including both functional and physical binding assays. Binding may be detected functionally by determining whether binding has an observable effect upon a biosynthetic process such as expression of a gene, DNA replication, transcription, translation, and the like.

Physical methods of detecting the binding of complementary strands of DNA or RNA are well known in the art, and include such methods as DNase I or chemical footprinting, gel shift and affinity cleavage assays, Northern blotting, dot blotting and light absorption detection procedures. For example, one method that is widely used, because it is so simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt.

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Biological sample: A biological specimen containing genomic DNA, RNA, protein, or combinations thereof, obtained from a subject. Examples include, but are not limited to, tissue biopsy, saliva, peripheral blood, urine, surgical specimen, and autopsy material. In one example, a sample includes a biopsy of an adrenal cortex, such as from a patient with a malignant or benign adrenocortical tumor or a healthy control subject. In other embodiments, the biological sample is blood, or a component thereof, such as plasma or serum.

Bisulfite treatment: The treatment of DNA with bisulfite or a salt thereof, such as sodium bisulfite ($NaHSO_3$). Bisulfite reacts readily with the 5,6-double bond of cytosine, but poorly with methylated cytosine. Cytosine reacts with the bisulfite ion to form a sulfonated cytosine reaction intermediate which is susceptible to deamination, giving rise to a sulfonated uracil. The sulfonate group can be removed under alkaline conditions, resulting in the formation of uracil. Uracil is recognized as a thymine by polymerases and amplification will result in an adenine-thymine base pair instead of a cytosine-guanine base pair.

CCNB2: A gene which encodes G2/mitotic-specific cyclin-B2. CCNB2 is also known as HsT17299. Cyclin B2 is a member of the cyclin family, specifically the B-type cyclins. The B-type cyclins, B1 and B2, associate with p34cdc2 and are essential components of the cell cycle regulatory machinery. B1 and B2 differ in their subcellular localization. Cyclin B1 co-localizes with microtubules, whereas cyclin B2 is primarily associated with the Golgi region. Cyclin B2 also binds to transforming growth factor beta RII and thus cyclin B2/cdc2 may play a key role in transforming growth factor beta-mediated cell cycle control. CCNB2 nucleic acid and protein sequences are publically available. For example GENBANK® Accession number NM_004701 discloses a human CCNB2 mRNA sequence and GENBANK® Accession numbers NP_004692 a human CCNB2 protein sequence each of which is incorporated by reference as of Mar. 15, 2013). In one example, a CCNB2 nucleic acid molecule is a malignant adrenocortical tumor-related molecule.

cDNA (complementary DNA): A piece of DNA lacking internal, non-coding segments (introns) and transcriptional regulatory sequences. cDNA may also contain untranslated regions (UTRs) that are responsible for translational control in the corresponding RNA molecule. cDNA is usually synthesized in the laboratory by reverse transcription from messenger RNA extracted from cells.

Chemotherapeutic agents: Any chemical agent with therapeutic usefulness in the treatment of diseases characterized by abnormal cell growth. Such diseases include tumors, neoplasms, and cancer, including ACC. In some cases, a chemotherapeutic agent is a radioactive compound. One of skill in the art can readily identify a chemotherapeutic agent of use (e.g., see Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., ©2000 Churchill Livingstone, Inc; Baltzer, L., Berkery, R. (eds): Oncology Pocket Guide to Chemotherapy, 2nd ed. St. Louis, Mosby-Year Book, 1995; Fischer, D. S., Knobf, M. F., Durivage, H. J. (eds): The Cancer Chemotherapy Handbook, 4th ed. St. Louis, Mosby-Year Book, 1993). Combination chemotherapy is the administration of more than one agent to treat cancer.

Comparative genomic hybridization: A technique of differential labeling of test DNA and normal reference DNA, which are hybridized simultaneously to chromosome spreads, as described in Kallioniemi et al. (*Science* 258:818-821, 1992), incorporated by reference.

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with the bases in a second nucleic acid strand. Complementarity is conveniently described by percentage, e.g, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between the oligonucleotide and the target nucleic acid (such as one or more of the disclosed malignant adrenocortical tumor molecules, such as KCTD12, KIRREL, SYNGR1 and/or NTNG2 nucleic acids) to achieve detectable binding. When expressed or measured by percentage of base pairs formed, the percentage complementarity that fulfills this goal can range from as little as about 50% complementarity to full (100%) complementary. In general, sufficient complementarity is at least about 50%, about 75% complementarity, about 90% or 95% complementarity, and or about 98% or even 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Contacting: Placement in direct physical association, including both in solid and in liquid form.

Control: A "control" refers to a sample or standard used for comparison with an experimental/test sample. In some embodiments, the control is a sample obtained from a healthy subject (such as a subject without cancer), a non-tumor tissue sample obtained from a patient diagnosed with cancer or a non-cancerous tissue sample from a cadaver. In some embodiments, the control is a historical control or standard reference value or range of values (such as a previously tested control sample, such as a group of cancer patients with good prognosis, or group of samples that represent baseline or normal values, such as the level of methylation of a target nucleic acid (for example, a malignant adrenocortical tumor molecules, such as KCTD12, KIRREL, SYNGR1, NTNG2, IL13RA2, HTR2B, CCNB2, RARRES2, and/or SLC16A9) in non-tumor tissue. In some embodiments, a control is a benign adrenocortical tumor or a reference value known to represent the level of methylation of a target nucleic acid in a benign adrenocortical tumor. In some embodiments, the control is a benign adrenocortical tumor obtained from a different subject. In some embodiments, the control is non-cancerous tissue sample obtained from the same subject, such as a benign tumor adjacent to the tumor. In other embodiments, the control is non-cancerous tissue sample obtained from the same subject, such as non-cancerous tissue surrounding the malignant tumor. In other embodiments, the control is an adrenocortical tissue sample obtained from a healthy patient or a non-cancerous tissue sample from a cadaver. In other embodiments, the reference sample is a standard or reference value based on an average of historical values.

Decrease or downregulate: To reduce the quality, amount, or strength of something. In one example, a therapy decreases a tumor (such as the size of a tumor, the number of tumors, the metastasis of a tumor, or combinations thereof), or one or more symptoms associated with a tumor, for example as compared to the response in the absence of the therapy (such as a therapy administered to affect tumor size via administration of an agent capable of decreasing methylation of one or more of the disclosed malignant adrenocortical tumor associated molecules). In a particular example, a therapy decreases the size of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein.

In some examples, when used in reference to the expression of nucleic acid molecules (such as mRNA), a reduction or downregulation refers to any process which results in a decrease in production of a gene product. In the context of the present disclosure, a gene product can be a primary transcript microRNA (pri-miRNA), precursor microRNA (pre-miRNA), mature microRNA or mRNA. Gene downregulation includes any detectable decrease in the production of a microRNA or mRNA. In certain examples, production of a microRNA or mRNA decreases by at least 2-fold, at least 3-fold, at least 4-fold, at least 5-fold, at least 6-fold, at least 8-fold, at least 10-fold, at least 15-fold, at least 20-fold, at least 30-fold or at least 40-fold, as compared to a control.

Deletion: The removal of one or more bases from a DNA molecule, the regions on either side of the removal being joined together.

Demethylating agent: An agent that can inhibit methylation, resulting in the expression of the previously hypermethylated silenced genes. In some examples, a demethylating agent is a histone deacetylase inhibitors belonging to the following class of drugs: hydroxamic acids (e.g., trichostatin A), cyclic tetrapeptides (e.g., trapoxin B, depsipeptides), benzamides, electrophilic ketones, and aliphatic acid (as phenylbutyrate and valproic acid) compounds such. In some examples, a demethylating agent is a second-generation histone deacetylase inhibitors such as the hydroxamic acids (vorinostat, belinostat, panobinostat), and the benzamides (entinostat, mocetinostat).

In some examples, a demethylating agent is a cytidine analog such as 5-azacytidine (azacitidine) and 5-azadeoxycytidine (decitabine). Cytidine analogs bind to DNA methyltransferases that catalyse the methylation reaction and titrate out these enzymes. Azacitidine and decitabine are marketed as Vidaza and Dacogen, respectively. In some examples, a demethylating agent is procaine.

Detect: To measure or determine the presence or absence of. In one example, to detect is to detect, if a particular nucleotide, for example a cytosine, guanine, or methylated cytosine, is present or absent. In some examples, this can further include quantification. In some examples, "detecting a beta difference" is a difference derived from calculating beta-values at each locus ($\beta$=Intensity of methylated allele/intensity of unmethylated allele+intensity of methylated allele+100) followed by analysis with R package to normalize the data. In some examples, detection of a beta difference of ≥0.2 in methylation of a DNA sample relative to control values is indicative that the subject has a malignant adrenocortical tumor or a malignant adrenocortical proliferative disorder.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, and biopsy.

DNA (deoxyribonucleic acid): DNA is a long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide, or for a stop signal. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

DNA methylation: The covalent addition of a methyl group (—$CH_3$) to the 5'-carbon of cytosine, usually in a CpG dinucleotide, or sometimes adenine (particularly in bacteria). CpG sites are located throughout the genome. In eukaryotic cells, methylation is a means of inhibiting gene expression.

A "CpG Island" refers to a region of at least 200bp with increased GC content. CpG islands tend to be found in promoter regions, the first exons of housekeeping genes, and other frequently expressed genes (Li et al., *Cell* 69: 915-926, 2002). In some examples, CpG shores are regions 0-2 kb from CpG islands, shelves are regions 2-4 kb from CpG islands and other/open sea regions are isolated CpG sites in the genome that do not have a specific designation.

Effective amount: An amount of agent that is sufficient to generate a desired response, such as reducing or inhibiting one or more signs or symptoms associated with a condition or disease. When administered to a subject, a dosage will generally be used that will achieve target tissue concentrations. In some examples, an "effective amount" is one that treats one or more symptoms and/or underlying causes of any of a disorder or disease. In some examples, an "effective amount" is a therapeutically effective amount in which the agent alone with an additional therapeutic agent(s) (for example a chemotherapeutic agent), induces the desired response such as treatment of a tumor, such as a malignant adrenocortical tumor. In one example, a desired response is to decrease tumor size or metastasis in a subject to whom the therapy is administered. Tumor metastasis does not need to be completely eliminated for the composition to be effective. For example, a composition can decrease metastasis by a desired amount, for example by at least 20%, at least 50%, at least 60%, at least 70%, at least 80%, at least 90%, at least 95%, at least 98%, or even at least 100% (elimination of the tumor), as compared to metastasis in the absence of the composition.

In particular examples, it is an amount of an agent effective to decrease a number of malignant adrenocortical carcinoma cells, such as in a subject to whom it is administered, for example a subject having one or more carcinomas. The cancer cells do not need to be completely eliminated for the composition to be effective. For example, a composition can decrease the number of cancer cells by a desired amount, for example by at least 20%, at least 50%, at least 60%, at least 70%, at least 80%, at least 90%, at least 95%, at least 98%, or even at least 100% (elimination of detectable cancer cells), as compared to the number of cancer cells in the absence of the composition.

In other examples, it is an amount of an agent capable of modulating one or more of the disclosed malignant adrenocortical tumor molecules (such as one or more malignant adrenocortical tumor molecules associated with ACC) by least 20%, at least 50%, at least 60%, at least 70%, at least 80%, at least 90%, at least 95%, at least 98%, or even at least 100% (elimination of detectable tumor growth) by the agent.

ERBB3: v-erb-b2 erythroblastic leukemia viral oncogene homolog 3 (avian) (also known as ErbB-3, HER3, LCCS2, MDA-BF-1, c-erbB-3, c-erbB3, erbB3-S, p180-ErbB3, p45-sErbB3, p85-sErbB3), GeneID: 2065 (available on-line on the World Wide Web at ncbi.nlm.nih.gov/gene/2065, the entire content of which is incorporated by reference as of Mar. 26, 2012). In one example, an ERBB3 nucleic acid molecule is hypermethylated and downregulated in a malignant adrenocortical tumor and is a therapeutic target for treating a malignant adrenocortical tumor.

GATA6: GATA binding protein 6 Potassium channel tetramerisation domain containing 12 (also known as AA410133 and GATA-6), GeneID: 2627 (available on-line on the World Wide Web at ncbi.nlm.nih.gov/gene/2627, the entire content of which is incorporated by reference as of Mar. 26, 2012). In one example, a GATA6 nucleic acid molecule includes a potentially methylated cytosine within a CpG site. In one example, a GATA6 nucleic acid includes the sequence provided in Table 3 wherein the bracketed CG is a potentially methylated CpG site.

Gene expression fingerprint (or profile): A distinct or identifiable pattern of gene expression, for instance a pattern of high and low expression of a defined set of genes; in some instances, as few as one or two genes may provide a profile, but often more genes are used in a profile, for instance at least three, at least 5, at least 10, at least 20, at least 25, or at least 50 or more. Gene expression fingerprints (also referred to as profiles) can be linked to a tissue or cell type, to a particular stage of normal tissue growth or disease progression, or to any other distinct or identifiable condition that influences gene expression in a predictable way. Gene expression fingerprints can include relative as well as absolute expression levels of specific genes, and often are best viewed in the context of a test sample compared to a baseline or control sample fingerprint. By way of example, a gene expression profile may be read on an array (e.g., a polynucleotide or polypeptide array). Arrays are now well known, and for instance gene expression arrays have been previously described in published PCT application number PCT/US99/06860, incorporated herein by reference in its entirety.

H19: Imprinted maternally expressed transcript (non-protein coding (also known as ASM, BWS, WT2, ASM1, PRO2605, D11S813E, LINC00008 and NCRNA00008), GeneID: 283120 (available on-line on the World Wide Web at ncbi.nlm.nih.gov/gene/283120, the entire content of which is incorporated by reference as of Mar. 26, 2012). In one example, a H19 nucleic acid molecule includes a potentially methylated cytosine within a CpG site. In one example, a H19 nucleic acid molecule is hypermethylated and downregulated in a malignant adrenocortical tumor and is a therapeutic target for treating a malignant adrenocortical tumor.

HOPX: Homeodomain-only protein is a protein that in humans is encoded by the HOPX gene (also known as CAMEO, HOD, HOP, LACY, NECC1, OB1, SMAP31, TOTO), GeneID: 84525 (available on-line on the World Wide Web at ncbi.nlm.nih.gov/gene/84525, the entire content of which is incorporated by reference as of Mar. 26, 2012). In one example, a HOPX nucleic acid molecule is hypermethylated and downregulated in a malignant adrenocortical tumor and is a therapeutic target for treating a malignant adrenocortical tumor.

HTR2B: A gene that encodes one of the several different receptors for 5-hydroxytryptamine (serotonin) that belongs to the G-protein coupled receptor 1 family. HTR2B nucleic acid and protein sequences are publically available. For example GENBANK® Accession number NM_000867 discloses a human HTR2B mRNA sequence and GENBANK® Accession numbers NP_000858.3 a human HTR2B protein sequence each of which is incorporated by reference as of Mar. 15, 2013). In one example, a CCNB2 nucleic acid molecule is a malignant adrenocortical tumor-related molecule.

IGF2: Insulin-like growth factor 2 (somatomedin A) (also known as IGF-II; PP9974; or C11orf43), GeneID: 3481 (available on-line on the World Wide Web at ncbi.nlm.nih.gov/gene/3481, the entire content of which is incorporated by reference as of Mar. 26, 2012). In one example, a IGF2 nucleic acid molecule includes a potentially methylated cytosine within a CpG site.

IL13RA2: A gene which encodes interleukin-13 receptor subunit alpha-2 (IL-13Rα2), also known as CD213A2 (cluster of differentiation 213A2), a membrane bound protein. IL13RA2 nucleic acid and protein sequences are publically available. For example GENBANK® Accession number NM_000640 discloses a human CCNB2 mRNA sequence and GENBANK® Accession numbers NP_000631 a human CCNB2 protein sequence each of which is incorporated by reference as of Mar. 15, 2013). In one example, a CCNB2 nucleic acid molecule is a malignant adrenocortical tumor-related molecule. In one example, a IL13RA2 nucleic acid molecule includes a potentially methylated cytosine within a CpG site. In one example, a IL13RA2 nucleic acid includes the sequence provided in Table 3 wherein the bracketed CG is a potentially methylated CpG site.

In vitro amplification: Techniques that increase the number of copies of a nucleic acid molecule (such as a KCTD12, KIRREL, SYNGR1, NTNG2, IL13RA2, HTR2B, CCNB2, RARRES2, or SLC16A9 nucleic acid) in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An "isolated" biological component (such as a nucleic acid molecule, protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids KCTD12: Potassium channel tetramerisation domain containing 12 (also known as PFET1, PFETIN, or C13orf2), GeneID: 115207 (available on-line on the World Wide Web at ncbi.nlm.nih.gov/gene/115207, the entire content of which is incorporated by reference as of Mar. 26, 2012). In one example, a KCTD12 nucleic acid molecule includes a potentially methylated cytosine within a CpG site.

KIRREL: Kin of IRRE like (Drosophila)(also known as RP11-444M10.2 or NEPH1), GeneID: 55243 (available on-line on the World Wide Web at ncbi.nlm.nih.gov/gene/155243, the entire content of which is incorporated by reference as of Mar. 26, 2012). In one example, a KIRREL nucleic acid molecule includes a potentially methylated cytosine within a CpG site.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemi-luminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Malignant adrenocortical tumor-related/associated molecule: A molecule that is associated with a malignant adrenocortical tumor. In some examples, a malignant adrenocortical tumor-related/associated molecule is one in which the methylation and/or expression level is altered as compared to a benign or non-tumor control value. In some examples, a malignant adrenocortical tumor-related molecule is KCTD12, KIRREL, SYNGRI, NTNG2, GATA6, TP53, β-catenin (CTNNB1), a hypermethylated CpG sites associated with imprinted genes of the chromosome 11p15 locus (such as IGF2 and H19), one or more genes associated with the IGF2 signaling pathway (such as IGF1R and/or AKT1), RARRES2, SLC16A9 or any molecule listed in Tables 2-5. In one example, a malignant adrenocortical tumor-related molecule is IL13RA2, HTR2B, CCNB2, RARRES2, or SLC16A9.

Measuring the level of expression: As used herein, measuring the level of expression of a gene or gene product, including mRNA, refers to quantifying the amount of the gene or gene product, such as mRNA, present in a sample. Quantification can be either numerical or relative. Detecting expression of the mRNA can be achieved using methods described herein, such as by microarray analysis or RT-PCR. In primary embodiments, the change detected is an increase or decrease in expression as compared to a control, such as a reference value or a healthy control subject. In some examples, the detected increase or decrease is an increase or decrease of at least two-fold compared with the control or standard. Controls or standards for comparison to a sample, for the determination of differential expression, include samples believed to be normal (in that they are not altered for the desired characteristic, for example a sample from a subject who does not have cancer, such as ACC) as well as laboratory values (e.g., range of values), even though possibly arbitrarily set, keeping in mind that such values can vary from laboratory to laboratory.

Laboratory standards and values can be set based on a known or determined population value and can be supplied in the format of a graph or table that permits comparison of measured, experimentally determined values.

In other examples, the detected increase or decrease is a change rounded down to the nearest whole number (so that both 2.05 and 2.67 are rounded down to 2) of the fold change shown for a mRNA in the Example Section, or is rounded to the nearest whole number (so that 2.05 would be rounded to 2 and 2.67 would be rounded to 3). In other embodiments of the methods, the increase or decrease is of a diagnostically significant amount, which refers to a change of a sufficient magnitude to provide a statistical probability of the diagnosis.

Methylation: A chemical or biochemical process of introducing a methyl group into an organic molecule. DNA methylation, the addition of a methyl group onto a nucleotide, is a post-replicative covalent modification of DNA that is catalyzed by a DNA methyltransferase enzyme (Koomar et al., *Nucl. Acids Res.* 22:1-10, 1994; and Bestor et al., *J. Mol. Biol.* 203:971-983, 1988).

In biological systems, DNA methylation can serve as a mechanism for changing the structure of DNA without altering its coding function or its sequence. DNA methylation is a heritable, reversible and epigenetic change. In some embodiments, it can alter gene expression, particularly by inactivating genes, which may have developmental and disease consequences. For example, methylation of CpG islands that are associated with tumor suppressor genes can cause decreased gene expression. Increased methylation of such regions can lead to a reduction of normal gene expression, which may cause the selection of a population of cells having a selective growth advantage and thus may become malignant.

Methylation status: The presence or absence of a methylated cytosine, such as a CG dinucleotide in a nucleic acid molecule (such as a malignant adrenocortical tumor associated nucleic acid molecule, such as a KCTD12, KIRREL, SYNGR1, NTNG2 or IL13RA2, HTR2B, CCNB2, RARRES2, and/or SLC16A9 nucleic acid molecule). Methylation status can be determined directly, for example using a DNA endonuclease that recognizes methylated cytosine. Methylation status can also be determined by exposing a cytosine containing DNA to an agent, such as but not limited to bisulfite, which converts unmethylated cytosine to another nucleotide and determining if the cytosine is resistant to conversion as disclosed herein, In some examples, an "abnormally methylated" cytosine is the presence of a methylated cytosine in a nucleic acid sequence in a sample from a subject with cancer (such as ACC), but not in the same nucleic acid sequence in a control (such as a sample from a subject without cancer). In other examples, and "abnormally methylated" cytosine is an increase in the amount of methylation of a cytosine in a nucleic acid sequence in a sample from a subject with cancer (such as ACC), but not in the same nucleic acid sequence in a control (such as a sample from a subject without cancer).

Modifying agent: An agent, such as a chemical agent, that "converts" an unmethylated cytosine to another nucleotide, thereby producing a converted nucleic acid molecule that includes the converted unmethylated cytosine. The modifying agents described herein do not convert methylated cytosine. Thus, converted unmethylated cytosine will distinguish the unmethylated from the methylated cytosine. In some embodiments, the modifying agent converts unmethylated cytosine to uracil. In one example, the modifying agent used for converting unmethylated cytosine is bisulfite or a salt thereof, such as sodium bisulfite ($NaHSO_3$), however, other agents that similarly convert unmethylated cytosine, but not methylated cytosine can also be used.

Neoplasm: A new and abnormal growth, particularly a new growth of tissue or cells in which the growth is uncontrolled and progressive. A tumor is an example of a neoplasm.

NTNG2: Netrin G2 (also known as RP11-479K20.2, LHLL9381, Lmnt2, NTNG1, bA479K20.1), GeneID: 84628 (available on-line on the World Wide Web at ncbi.nlm.nih.gov/gene/84628, the entire content of which is incorporated by reference as of Mar. 26, 2012). In one example, a NTNG2 nucleic acid molecule includes a potentially methylated cytosine within a CpG site.

Nuclease: An enzyme capable of cleaving the phosphodiester bond between nucleotides. Nuclease resistant refers to a nucleic acid molecule having at least one bond between nucleotides that cannot be cleaved by a nuclease. Nucleases include both endonucleases and exonucleases. Endonucleases are enzymes that cleave the phosphodiester bond within a polynucleotide chain. Restriction endonucleases (restriction enzymes) cleave DNA at specific sites dictated by their recognition sequence. Exonucleases are enzymes that cleave nucleotides one at a time from an end of a polynucleotide chain. These enzymes hydrolyze phosphodiester bonds from either the 3' or 5' terminus of polynucleotide molecules. An "RNAse" is a nuclease that cleaves the phosphodiester bond between ribonucleotides in an RNA strand.

Nucleic acid or nucleic acid molecule: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. Such polynucleotides can be synthesized, for example, using an automated DNA synthesizer.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3'-end of the coding RNA transcript are referred to as "downstream sequences."

A "converted nucleic acid molecule" is a nucleic acid molecule in which one or more of the nucleotides have been chemically converted to another nucleotide, for example with a modifying agent such as bisulfite. In one example, a "converted nucleic acid molecule" is converted such that one or more (for example, all) of the unmethylated cytosines have been chemically converted to uracil. After amplification, such a converted nucleic acid molecule will have thymine in place of the unmethylated cytosines. The complementary amplified strand will have adenine in place of guanine.

Nucleotide: "Nucleotide" includes, but is not limited to, a monomer that includes a base linked to a sugar, such as a pyrimidine, purine or synthetic analogs thereof, or a base linked to an amino acid, as in a peptide nucleic acid. A nucleotide is one monomer in a polynucleotide. A nucleotide sequence refers to the sequence of bases in a polynucleotide.

The major nucleotides are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T) and uridine 5'-triphosphate (UTP or U).

Many modified nucleotides (nucleotide analogs) are known and can be used in oligonucleotides, such as the probes and primers for use in the disclosed methods. A nucleotide analog is a nucleotide which contains some type of modification to either the base, sugar, or phosphate moieties. It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate nucleic acid. Nucleotide substitutes are nucleotides or nucleotide analogs that have had the phosphate moiety and/or sugar moieties replaced.

In one example, a modified nucleotide is a sulfonated cytosine. In one example, a modified nucleotide is a sulfonated uracil.

Oligonucleotide: An oligonucleotide is a plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Probes and primers: Nucleic acid probes and primers can be readily prepared based on the nucleic acid molecules provided in this disclosure as indicators of disease or disease progression. It is also appropriate to generate probes and primers based on fragments or portions of these nucleic acid molecules. Also appropriate are probes and primers specific for the reverse complement of these sequences, as well as probes and primers to 5' or 3' regions.

A probe comprises an isolated nucleic acid attached to a detectable label or other reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, e.g., in Sambrook et al. (In *Molecular Cloning: A Laboratory Manual,* CSHL, New York, 1989) and Ausubel et al. (In Current Protocols in Molecular Biology, John Wiley & Sons, New York, 1998).

Primers are short nucleic acid molecules, for instance DNA oligonucleotides 10 nucleotides or more in length. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the polymerase chain reaction (PCR) or other nucleic acid amplification methods known in the art.

Methods for preparing and using nucleic acid probes and primers are described, for example, in Sambrook et al. (In *Molecular Cloning: A Laboratory Manual,* CSHL, New York, 1989), Ausubel et al. (ed.) (In *Current Protocols in Molecular Biology,* John Wiley & Sons, New York, 1998), and Innis et al. (*PCR Protocols, A Guide to Methods and Applications,* Academic Press, Inc., San Diego, Calif., 1990). PCR primer pairs can be derived from a known sequence, for example, by using computer programs intended for that purpose such as Primer (Version 0.5, ©1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of a malignant adrenocortical tumor-related protein encoding nucleotide will anneal to a target sequence, such as another homolog of the designated malignant adrenocortical tumor-related protein, with a higher specificity than a corresponding primer of only 15 nucleotides. Thus, in order to obtain greater specificity, probes and primers can be selected that comprise at least 20, 25, 30, 35, 40, 45, 50 or more consecutive nucleotides of a malignant adrenocortical tumor-related nucleotide sequences (such as KCTD12, KIRREL, SYNGR1, NTNG2, IL13RA2, HTR2B, CCNB2, RARRES2, or SLC16A9).

The disclosure thus includes isolated nucleic acid molecules that comprise specified lengths of the disclosed malignant adrenocortical tumor-related nucleotide sequences (such as a KCTD12, KIRREL, SYNGR1, NTNG2, IL13RA2, HTR2B, CCNB2, RARRES2, or SLC16A9 nucleotide sequence). Such molecules may comprise at least 10, 15, 20, 23, 25, 30, 35, 40, 45 or 50 consecutive nucleotides of these sequences or more, and may be obtained from any region of the disclosed sequences (e.g., a malignant adrenocortical tumor-related nucleic acid may be apportioned into halves or quarters based on sequence length, and isolated nucleic acid molecules may be derived from the first or second halves of the molecules, or any of the four quarters, etc.). A malignant adrenocortical tumor-related cDNA also can be divided into smaller regions, e.g. about eighths, sixteenths, twentieths, fiftieths and so forth, with similar effect.

Another mode of division is to select the 5' (upstream) and/or 3' (downstream) region associated with a disclosed malignant adrenocortical tumor-related gene, such as KCTD 12, KIRREL, SYNGR1, NTNG2, IL13RA2, HTR2B, CCNB2, RARRES2, or SLC16A9.

Nucleic acid molecules may be selected that comprise at least 10, 15, 20, 25, 30, 35, 40, 50 or 100 or more consecutive nucleotides of any of these or other portions of a specified nucleic acid molecule, such as those disclosed herein, and associated flanking regions. Thus, representative nucleic acid molecules might comprise at least 10 consecutive nucleotides of a human coding sequence the expression of which is influenced by adrenocortical tumor progression, such as KCTD12, KIRREL, SYNGR1, NTNG2, IL13RA2, HTR2B, CCNB2, RARRES2, or SLC16A9.

Prognosis: A prediction of the course of a disease, such as an adrenocortical tumor (for example, ACC). The prediction can include determining the likelihood of a subject to develop aggressive, recurrent disease, to develop one or more metastases, to survive a particular amount of time (e.g., determine the likelihood that a subject will survive 1, 2, 3, 4, 5, or more years), to respond to a particular therapy (e.g., chemotherapy), or combinations thereof. The prediction can also include determining whether a subject has a malignant or a benign tumor.

Purified: The term "purified" does not require absolute purity; rather, it is intended as a relative term. Thus, for example, a purified protein preparation is one in which the protein referred to is more pure than the protein in its natural environment within a cell or within a production reaction chamber (as appropriate).

RARRES2: Retinoic acid receptor responder (tazarotene induced) (also known as HP10433, TIG2), GeneID: 5919 (available on-line on the World Wide Web at ncbi.nlm.nih.gov/gene/5919, the entire content of which is incorporated by reference as of Mar. 26, 2012). In one example, a RARRES2 nucleic acid molecule includes a potentially methylated cytosine within a CpG site. In one example, a RARRES2 nucleic acid includes the sequence provided in Table 3 wherein the bracketed CG is a potentially methylated CpG site.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Representational difference analysis: A PCR-based subtractive hybridization technique used to identify differences in the mRNA transcripts present in closely related cell lines.

RUNX2: Runt-related transcription factor 2 (also known as RP1-166H4.1, AML3, CBFA1, CCD, CCD1, OSF-2, OSF2, PEA2aA, PEBP2A1, PEBP2A2, PEBP2aA, PEBP2aA1), GeneID: 860 (available on-line on the World Wide Web at ncbi.nlm.nih.gov/gene/860, the entire content of which is incorporated by reference as of Mar. 26, 2012). In one example, a RUNX2 nucleic acid molecule is hypermethylated and downregulated in a malignant adrenocortical tumor and is a therapeutic target for treating a malignant adrenocortical tumor.

S100A10: S100 calcium binding protein A10 (also known as 42C, ANX2L, ANX2LG, CAL1L, CLP11, GP11, P11, p10), GeneID: 6281 (available on-line on the World Wide Web at ncbi.nlm.nih.gov/gene/6281, the entire content of which is incorporated by reference as of Mar. 26, 2012). In one example, a S100A10 nucleic acid molecule is hypermethylated and downregulated in a malignant adrenocortical tumor and is a therapeutic target for treating a malignant adrenocortical tumor.

Serial analysis of gene expression: The use of short diagnostic sequence tags to allow the quantitative and simultaneous analysis of a large number of transcripts in tissue, as described in Velculescu et al. (*Science* 270:484-487, 1995).

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a malignant adrenocortical tumor-related protein, and the corresponding cDNA or gene sequence, will possess a relatively high degree of sequence identity when aligned using standard methods.

Methods of alignment of sequences for comparison are well known in the art. Various programs and alignment algorithms are described in: Smith & Waterman, *Adv. Appl. Math.* 2: 482, 1981; Needleman & Wunsch, *J. Mol. Biol.* 48: 443, 1970; Pearson & Lipman, *Proc. Natl. Acad. Sci. USA* 85: 2444, 1988; Higgins & Sharp, *Gene,* 73: 237-244, 1988; Higgins & Sharp, *CABIOS* 5: 151-153, 1989; Corpet et al., *Nucl. Acids Res.* 16, 10881-90, 1988; Huang et al., *Computer Appls. in the Biosciences* 8, 155-65, 1992; and Pearson et al., *Meth. Mol. Bio.* 24, 307-31, 1994. Altschul et al. (*J. Mol. Biol.* 215:403-410, 1990) presents a detailed consideration of sequence alignment methods and homology calculations.

The NCBI Basic Local Alignment Search Tool (BLAST) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. By way of example, for comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties).

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point $(T_m)$ for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (In *Molecular Cloning: A Laboratory Manual,* CSHL, New York, 1989) and Tijssen (*Laboratory Techniques in Biochemistry and Molecular Biology—Hybridization with Nucleic Acid Probes* Part I, Chapter 2, Elsevier, New York, 1993). Nucleic acid molecules that hybridize under stringent conditions to a specific human malignant adrenocortical tumor-related protein-encoding sequence will typically hybridize to a probe based on either an entire human malignant adrenocortical tumor-related protein-encoding sequence or selected portions of the encoding sequence under wash conditions of 2× SSC at 50° C.

SLC16A9: Solute carrier family 16, member 9 (monocarboxylic acid transporter 9) (also known as C10orf36 or MCT9), GeneID: 220963 (available on-line on the World Wide Web at ncbi.nlm.nih.gov/gene/220963, the entire content of which is incorporated by reference as of Mar. 26, 2012). In one example, a SLC16A9 nucleic acid molecule includes a potentially methylated cytosine within a CpG site. In one example, a SLC16A9 nucleic acid includes one or more of the sequences provided in Table 3, wherein the bracketed CG is a potentially methylated CpG site.

Subject: Living multi-cellular vertebrate organisms, a category that includes both human and non-human mammals.

SYNGR1: Synaptogyrin 1 (also known as RP3-333H23.3), GeneID: 9145 (available on-line on the World Wide Web at ncbi.nlm.nih.gov/gene/9145, the entire content of which is incorporated by reference as of Mar. 26, 2012). In one example, a SYNGR1 nucleic acid molecule includes a potentially methylated cytosine within a CpG site.

Target sequence: A sequence of nucleotides (such as a sequence of nucleotides located in a particular region in the human genome) that corresponds to one or more specific genetic changes, such as a nucleotide polymorphism, a deletion, an amplification, or methylation. The target can be for instance a coding sequence; it can also be the non-coding strand that corresponds to a coding sequence. The target can also be a non-coding sequence, such as a regulatory region, for example a promoter. In a particular example, a target sequence is a disclosed malignant adrenocortical tumor-related nucleic acid sequence, such as a KCTD12, KIRREL, SYNGR1, NTNG2, IL13RA2, HTR2B, CCNB2, RARRES2, or SLC16A9 nucleic acid sequence.

Tissue: A plurality of functionally related cells. A tissue can be a suspension, a semi-solid, or solid. Tissue includes cells collected from a subject, such as from the adrenal cortex. A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

TP53: Tumor protein p53 (also known as LFS1, P53, TRP53), GeneID: 7157 (available on-line on the World Wide Web at ncbi.nlm.nih.gov/gene/7157, the entire content of which is incorporated by reference as of Mar. 26, 2012). In one example, a TP53 nucleic acid molecule includes a potentially methylated cytosine within a CpG site. In one example, a TP53 nucleic acid includes the sequence provided in Table 3, wherein the bracketed CG is a potentially methylated CpG.

Treating a disease: A phrase referring to a therapeutic intervention that ameliorates a sign or symptom of a disease or pathological condition after it has begun to develop.

Tumor, neoplasia, malignancy or cancer: The result of abnormal and uncontrolled growth of cells. Neoplasia, malignancy, cancer and tumor are often used interchangeably and refer to abnormal growth of a tissue or cells that results from excessive cell division. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." "Malignant cells" are those that have the properties of anaplasia invasion and metastasis. In one example, a tumor is an adrenal tumor. An adrenal tumor can be benign or malignant. Malignant adrenal tumors include neuroblastoma, adrenocortical carcinoma (ACC), and a minority of adrenal pheochromocytomas. Most adrenal pheochromocytomas and all adrenocortical adenomas are benign tumors, which do not metastasize or invade nearby tissues, but which may still cause significant health problems by giving rise to hormonal imbalances. Disclosed herein are particular adrenocortical tumor associated molecules which can be used to diagnosis a subject with a malignant adrenal tumor, such as ACC as these molecules are differentially expressed in malignant adrenal cortex tumors as compared to benign adrenal cortex tumors.

Adrenocortical carcinoma is an aggressive cancer originating in the cortex (steroid hormone-producing tissue) of the adrenal gland. Adrenocortical carcinoma is a rare tumor with an incidence of 1-2 per million population annually. Adenocortical carcinoma is often associated with hormonal syndromes which can occur in patients with steroid hormone-producing ("functional") tumors, including Cushing's syndrome, Conn syndrome, virilization and feminization. Due to their location deep in the retroperitneum, most adrenocortical carcinomas are not diagnosed until they have grown quite large. They frequently invade large vessels, such as the renal vein and inferior vena cava, as well as metastasizing via the lymphatics and through the blood to the lungs and other organs. The most effective treatment currently is surgery, although this is not feasible for many patients, and the overall prognosis of the disease is poor. Chemotherapy, radiation therapy and hormonal therapy may also be employed in the treatment of this disease.

In contrast, adrenocortical adenomas are benign tumors of the adrenal cortex which are extremely common (present in 1-10% of persons at autopsy). The clinical significance of these neoplasms is twofold. First, they have been detected as incidental findings with increasing frequency in recent years, due to the increasing use of CT scans and magnetic resonance imaging in a variety of medical settings. This can result in expensive additional testing and invasive procedures to rule out the slight possibility of an early adrenocortical carcinoma. Second, a minority (about 15%) of adrenocortical adenomas are "functional", meaning that they produce glucocorticoids, mineralcorticoids, and/or sex steroids, resulting in endocrine disorders such as Cushing's syndrome, Conn's syndrome (hyperaldosteronism), virilization of females, or feminization of males. Functional adrenocortical adenomas are surgically curable.

Most of the adrenocortical adenomas are less than 2 cm in greatest dimension and less than 50 g in weight. However, size and weight of the adrenal cortical tumors are no longer considered to be a reliable sign of benignity or malignancy. Grossly, adrenocortical adenomas are encapsulated, well-circumscribed, solitary tumors with solid, homogeneous yellow-cut surface. Necrosis and hemorrhage are rare findings. Pheochromocytoma is a neoplasm composed of cells similar to the chromaffin cells of the mature adrenal medulla. Pheochromocytomas occur in patients of all ages, and may be sporadic, or associated with a hereditary cancer syndrome, such as multiple endocrine neoplasia (MEN) types IIA and IID, neurofibromatosis type I, or von Rippel-Lindau syndrome. Only 10% of adrenal pheochromocytomas are malignant, while the rest are benign tumors. The most clinically important feature of pheochromocytomas is their tendency to produce large amounts of the catecholamine hormones epinephrine (adrenaline) and norepinephrine. This may lead to potentially life-threatening high blood pressure, or cardiac arrythmias, and numerous symptoms such as headache, palpitations, anxiety attacks, sweating, weight loss and tremor. Diagnosis is often confirmed through urinary measurement of catecholamine metabolites. Typically, pheochromocytomas are initially treated with anti-adrenergic drugs to protect against catecholamine overload, with surgery employed to remove the tumor once the patient is medically stable.

Tumor suppressor gene: A gene in the body that can suppress or block the development of cancer. A tumor suppressor gene typically restrains cell growth but, when missing or inactivated by mutation, allow cells to grow uncontrolled. Tumor suppressor gene: Down-regulation of a tumor suppressor gene can contribute to the development of a cancer, such as ACC.

Weiss criteria: A combination of the following nine criteria for distinguishing malignant adrenocortical tumors from benign adrenocortical tumors: nuclear grade III or IV; mitotic rate greater than 5/50 high-power fields; atypical mitoses; clear cells comprising 25% or less of the tumor; a diffuse architecture; microscopic necrosis; and invasion of venous, sinusoidal, and capsular structures. The presence of three or more of these features in a given tumor indicates malignant potential.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In addition, all Gene IDs are herein incorporated by reference as they appear in the database on Mar. 26, 2012. In case of conflict, the present specification, including explanations of terms, will control. In addition, the materials, methods, and examples are illustrative only and not intended to be limiting.

II. Introduction

Changes at the epigenetic level have been implicated in carcinogenesis and found to be diagnostic and prognostic markers. Epigenetics refers to heritable changes in gene expression that are not due to changes in DNA. The most common epigenetic changes (which is essential for normal embryonic development) is DNA methylation of cytosines, by DNA methyltransferase enzymes, DNA methylation is a mechanism for changing the base sequence of DNA without altering its coding function. DNA methylation is a heritable, reversible and epigenetic change. Yet, DNA methylation has the potential to alter gene expression, which has profound developmental and genetic consequences. The methylation reaction involves flipping a target cytosine out of an intact double helix to allow the transfer of a methyl group from S adenosyl-methionine in a cleft of the enzyme DNA (cytosine-5)-methyltransferase to form 5-methylcytosine (5-mCyt).

Cytosines associated with guanines are called CpG dinucleotides, and these are generally found in CpG rich regions called CpG islands. CpG islands are defined as regions of greater than 500 bp that have GC content of greater than 55% and do not show suppression. Up to 60% of CpG islands are in the 5' regulatory (promoter) regions of genes. However, CpG islands that are not in promoter regions can also be found within coding regions and non-coding regions of genes which may be targets for de novo methylation in cancer and aging. DNA methylation affects a number of different cellular processes including apoptosis, cell cycle, DNA damage repair, growth factor response, signal transduction, and tumor architecture, all of which can contribute to the initiation and progression of cancer.

Methylation of cytosine residues contained within CpG islands of certain genes has been inversely correlated with gene activity. Thus, methylation of cytosine residues within CpG islands in somatic tissue is generally associated with decreased gene expression and can affect a variety of mechanisms including, for example, disruption of local chromatin structure, inhibition of transcription factor-DNA binding, or by recruitment of proteins which interact specifically with methylated sequences indirectly preventing transcription factor binding. Despite a generally inverse correlation between methylation of CpG islands and gene expression, most CpG islands on autosomal genes remain unmethylated in the germline and methylation of these islands is usually independent of gene expression. Tissue-specific genes are usually unmethylated at the receptive target organs but are methylated in the germline and in non-expressing adult tissues. CpG islands of constitutively-expressed housekeeping genes are normally unmethylated in the germline and in somatic tissues.

Abnormal methylation of CpG islands associated with tumor suppressor genes can cause decreased gene expression. Increased methylation (hypermethylation) of such regions can lead to progressive reduction of normal gene expression resulting in the selection of a population of cells having a selective growth advantage. Conversely, decreased methylation (hypomethylation) of oncogenes can lead to modulation of normal gene expression resulting in the selection of a population of cells having a selective growth advantage. In some examples, hypermethylation and/or hypomethylation of one or more CpG dinucleotide is considered to be abnormal methylation.

With particular regard to cancer, changes in DNA methylation have been recognized as one of the most common molecular alternations in human neoplasia. Hypermethylation of CpG islands located in the promoter regions of tumor suppressor genes is a well-established and common mechanism for gene inactivation in cancer. In contrast, a global hypomethylation of genomic DNA is observed in tumor cells and a correlation between hypomethylation and increased gene expression has been reported for many oncogenes.

Monitoring global changes in methylation pattern has been applied to molecular classification in breast cancer (Huang, et al., Hum Mol Genet. 8: 459-70, 1999). In addition, studies have identified a few specific methylation patterns in tumor suppressor genes, for example, p16, a cyclin-dependent kinase inhibitor, in certain human cancer types. Some examples include the discoveries of causal relationship between the loss of RUNX3 expression, due to hypermethylation, and gastric cancer (Li, et al., Cell 109: 113-24, 2002); loss of IGF2 imprinting in colorectal cancer (Cui, et al., Science 299: 1753-5, 2003); and reduced Hic gene expression in several types of human cancer.

Although changes in DNA methylation have been recognized as a common molecular alternations in human neoplasia, prior to the present disclosure DNA methylation changes associated with ACC had never been evaluated. The present studies not only characterized DNA methylation changes associated with ACC, but indicate that differential DNA methylation status may serve as diagnostic markers and/or targets for therapy for ACC. In particular, the inventors conducted a genome-wide DNA methylation analysis using a platform with 485, 421 cytosine probe sites. The methylome of 87 adrenocortical tissue samples (19 normal, 48 benign, 8 primary malignant, and 12 metastatic) was characterized and the correlation of gene-methylation status with gene expression levels in benign versus malignant adrenocortical tissues samples was determined. The methylation profiling revealed 1) that methylation patterns were distinctly different and could distinguish normal, benign, primary malignant and metastatic tissue samples, 2) that malignant samples have global hypomethylation, and 3) that the methylation of CpG regions are different in benign adrenocortical tumors by functional status. In addition, the inventors discovered several CpG sites which were differentially methylated for these types of tumors. As such, the present studies demonstrate that the methylation status of these CpG sites can be used to manage patients with adrenocortical tumors instead of or in addition to relying upon histopathological diagnosis of adrenocortical cancer (which is subjective in nature and often incapable of reliably distinguishing benign and malignant tumors accurately).

III. Overview of Several Embodiments

Disclosed herein are methods for detecting, diagnosing and/or prognosing a malignant adrenocortical tumor. In some embodiments, the method of diagnosing and/or prognosing includes obtaining a sample comprising genomic DNA from a subject at risk of acquiring or suspected to have an adrenocortical tumor; isolating genomic DNA from the sample; and measuring the level of one or more methylated genomic CpG dinucleotide sequences in one or more of the genomic targets, such as KCTD12, KIRREL, SYNGR1, NTNG2, GATA6, TP53, β-catenin (CTNNB1), IGF2, H19, IGF1R, AKT1, RARRES2, SLC16A9, IL13RA2, HTR2B, CCNB2, and/or molecules listed in Tables 2-5, in the sample, wherein an increase in the level of methylation of the one or more genomic CpG dinucleotide sequences in the sample compared to a control indicates a malignant adrenocortical tumor.

In some embodiments, measuring includes measuring the level of one or more methylated genomic CpG dinucleotide sequences within any one, any two of KCTD12, KIRREL, SYNGR1 and NTNG2, any three of KCTD12, KIRREL, SYNGR1 and NTNG2 or all four.

In some embodiments, measuring includes measuring the level of one or more methylated genomic CpG dinucleotide sequences within any one, any two of RARRES2, SLC16A9, IL13RA2, HTR2B, CCNB2, any three of RARRES2, SLC16A9, IL13RA2, HTR2B, CCNB2, any four of RARRES2, SLC16A9, IL13RA2, HTR2B, CCNB2 or all five.

In some embodiments, measuring includes measuring the level of one or more methylated genomic CpG dinucleotide sequences within any one, any two of KCTD12, KIRREL, SYNGR1, NTNG2, RARRES2, SLC16A9, IL13RA2, HTR2B, and CCNB2, any three of KCTD12, KIRREL, SYNGR1, NTNG2, RARRES2, SLC16A9, IL13RA2, HTR2B, and CCNB2, any four of KCTD12, KIRREL, SYNGR1, NTNG2, RARRES2, SLC16A9, IL13RA2, HTR2B, and CCNB2, any five of KCTD12, KIRREL, SYNGR1, NTNG2, RARRES2, SLC16A9, IL13RA2, HTR2B, and CCNB2, any six of KCTD12, KIRREL, SYNGR1, NTNG2, RARRES2, SLC16A9, IL13RA2, HTR2B, and CCNB2, any seven of KCTD12, KIRREL, SYNGR1, NTNG2, RARRES2, SLC16A9, IL13RA2, HTR2B, and CCNB2, any eight of KCTD12, KIRREL, SYNGR1, NTNG2, RARRES2, SLC16A9, IL13RA2, HTR2B, and CCNB2, or all nine.

In some embodiments, the method further comprises providing the diagnoses to the subject in a perceivable output that provides information about the diagnosis.

In some embodiments, the method further comprises providing a therapeutic regimen based on the diagnosis.

In some embodiments, the sample is an adrenocortical tissue biopsy sample.

In some embodiments, the method is used for diagnosing or prognosing a subject with adrenocortical carcinoma.

In some embodiments, the method is used to distinguish a primary malignant adrenocortical tumor from a benign adrenocortical tumor.

In some embodiments, the control is a benign adrenocortical tumor.

In some embodiments, the method further comprises contacting the isolated genomic DNA with sodium bisulfite prior to measuring the level of one or more methylated genomic CpG dinucleotide sequences thereby converting an unmethylated cytosine to a uracil in the genomic DNA while a methylated cytosine in the genomic DNA is resistant to the sodium bisulfite and remains unchanged prior to measuring the level of one or more methylated genomic CpG dinucleotide sequences.

In some embodiments, the method further comprises amplifying the sodium bisulfite treated genomic DNA.

In some embodiments, a method for detecting a malignant adrenocortical cell proliferative disorder in a subject includes contacting at least one malignant adrenocortical tumor-related nucleic acid in a sample from the subject with a reagent that detects methylation, wherein the one or more malignant adrenocortical tumor-related nucleic acid comprises KCTD12, KIRREL, SYNGR1, NTNG2, GATA6, TP53, β-catenin (CTNNB1), IGF2, H19, IGF1R, AKT1, RARRES2, SLC16A9, IL13RA2, HTR2B, CCNB2 and/or nucleic acids listed in Tables 2-5; and detecting methylation of the target nucleic acid, wherein an increase in methylation of the at least one malignant adrenocortical tumor-related nucleic acid as compared with the level of methylation of the corresponding nucleic acid in a control sample, is indicative of a malignant adrenocortical cell proliferative disorder.

In some embodiments, the method includes detecting methylation within any two of KCTD12, KIRREL, SYNGR1 and NTNG2, any three of KCTD12, KIRREL, SYNGR1 and NTNG2 or all four.

In some embodiments, the method includes detecting methylation within any two of RARRES2, SLC16A9, IL13RA2, HTR2B, CCNB2, any three of RARRES2, SLC16A9, IL13RA2, HTR2B, CCNB2, any four of RARRES2, SLC16A9, IL13RA2, HTR2B, CCNB2 or all five.

In some embodiments, the method includes detecting methylation within any two of KCTD12, KIRREL, SYNGR1, NTNG2, RARRES2, SLC16A9, IL13RA2, HTR2B, and CCNB2, any three of KCTD12, KIRREL, SYNGR1, NTNG2, RARRES2, SLC16A9, IL13RA2, HTR2B, and CCNB2, any four of KCTD12, KIRREL, SYNGR1, NTNG2, RARRES2, SLC16A9, IL13RA2, HTR2B, and CCNB2, any five of KCTD12, KIRREL, SYNGR1, NTNG2, RARRES2, SLC16A9, IL13RA2, HTR2B, and CCNB2, any six of KCTD12, KIRREL, SYNGR1, NTNG2, RARRES2, SLC16A9, IL13RA2, HTR2B, and CCNB2, any seven of KCTD12, KIRREL, SYNGR1, NTNG2, RARRES2, SLC16A9, IL13RA2, HTR2B, and CCNB2, any eight of KCTD12, KIRREL, SYNGR1, NTNG2, RARRES2, SLC16A9, IL13RA2, HTR2B, and CCNB2, or all nine.

In some embodiments, the reagent is a nucleic acid probe.

In some embodiments, the method is used to distinguish a primary malignant adrenocortical cell proliferative disorder from a benign adrenocortical cell proliferative.

In some embodiments, the control sample is a benign adrenocortical tumor. In some embodiments, the sample comprises adrenocortical tissue.

Also disclosed are methods of treating a malignant adrenocortical tumor. In some embodiments, the method includes administering to a subject with a malignant adrenocortical tumor an effective amount of a demethylating agent that alters the activity and/or expression of one or more malignant adrenocortical tumor molecules listed in Tables 2-4, thereby treating the malignant adrenocortical tumor.

In some embodiments, the method further includes selecting a subject with a malignant adrenocortical tumor prior to administering the treatment.

In some embodiments, selecting a subject with a malignant adrenocortical tumor comprises detecting methylation and mRNA expression of one or more malignant adrenocortical tumor molecules listed in Tables 2-5, whereby an increase in methylation and a decrease in mRNA expression of the one or more malignant adrenocortical tumor molecules indicate the subject has a malignant adrenocortical tumor.

In some embodiments, the one or more malignant adrenocortical tumor molecules comprise H19, S100A10, HOPX, ERBB3, RUNX2, or any combination thereof.

In some embodiments, the one or more malignant adrenocortical tumor molecules comprise RARRES2, SLC16A9, IL13RA2, HTR2B, CCNB2, or any combination thereof.

In some embodiments, the method of treatment is a method of treating ACC.

In some embodiments, the method further comprises administering one or more additional anti-cancer agents or therapeutic treatments (such as surgical resection of a tumor or radiation therapy).

IV. Detecting, Diagnosing and Prognosing Adrenocortical Tumors in a Subject

The present disclosure relates to diagnosis and prognosis of a malignant adrenocortical tumor assessing DNA methylation of malignant adrenocortical-tumor associated molecules, such as assessing one or more molecules provided in Tables 1-4 (such as KCTD12, KIRREL, SYNGR1, NTNG2, RARRES2, SLC16A9, IL13RA2, HTR2B, CCNB2, or any combination thereof). Having identified multiple genes as highly sensitive and specific for a malignant adrenocortical tumor, methods of detecting, diagnosing or prognosing an adrenocortical tumor, (e.g., ACC) or a predilection to adrenocortical cancer, in a subject are disclosed.

In one example, a method of diagnosing and/or prognosing an adrenocortical tumor includes measuring the level of one or more methylated genomic CpG dinucleotide sequences in one or more of the genomic targets (such as one or more molecules provided in Tables 1-5, including, but not necessarily limited to KCTD12, KIRREL, SYNGR1, NTNG2, RARRES2, SLC16A9, IL13RA2, HTR2B and/or CCNB2) in the sample obtained from a subject at risk of acquiring or suspected of having an adrenocortical tumor, wherein an increase in the level of methylation of the one or more genomic CpG dinucleotide sequences in the one or more genomic targets in the sample compared to a control indicates a malignant adrenocortical tumor. In one example, the method further includes obtaining a sample comprising genomic DNA from a subject at risk of acquiring or suspected of having an adrenocortical tumor prior to measuring the level of one or more methylated genomic CpG dinucleotide sequences in one or more of the genomic targets (such as one or more molecules provided in Tables 1-5, including, but not necessarily limited to KCTD12, KIRREL, SYNGR1, NTNG2, RARRES2, SLC16A9, IL13RA2, HTR2B and/or CCNB2) in the sample.

In some examples, the method further includes isolating genomic DNA from the sample and/or treating the sample with bisulfite prior to measuring the level of one or more methylated genomic CpG dinucleotide sequences in one or more of the genomic targets (such as KCTD12, KIRREL, SYNGR1 NTNG2, RARRES2, SLC16A9, IL13RA2, HTR2B and/or CCNB2) in the sample.

In one example, a method for detecting a malignant adrenocortical cell proliferative disorder in a subject includes contacting a target nucleic acid such as one or more molecules listed in Tables 1-5 (such as a target nucleic acid selected from the group consisting of KCTD12, KIRREL, SYNGR1, NTNG2, RARRES2, SLC16A9, IL13RA2, HTR2B and CCNB2 sequences) in a sample from the subject with a reagent that detects methylation; and detecting methylation of the target nucleic acid, wherein an increase in methylation of the target nucleic acid as compared with the level of methylation of the corresponding nucleic acid in a control sample, is indicative of a malignant adrenocortical cell proliferative disorder.

i. Obtaining Biological Sample

Detecting, diagnosing and/or prognosing a malignant adrenocortical tumor in a subject can include obtaining a biological sample from the subject. The sample can be any sample that includes genomic DNA. Such samples include, but are not limited to, tissue from biopsies (including formalin-fixed paraffin-embedded tissue), autopsies, and pathology specimens; sections of tissues (such as frozen sections or paraffin-embedded sections taken for histological purposes); body fluids, such as blood, sputum, serum, or urine, or fractions of any of these; and so forth. In one particular example, the sample from the subject is a tissue biopsy sample. In another specific example, the sample from the subject is serum.

Tissue samples can be obtained from a subject using any method known in the art. For example, tissue samples can be obtained from ACC patients who have undergone tumor resection as a form of treatment. From these patients, both tumor tissue and surrounding non-cancerous tissue can be obtained. In some embodiments, the non-cancerous tissue sample used as a control is obtained from a cadaver.

In some embodiments, tissue samples are obtained by biopsy. Biopsy samples can be fresh, frozen or fixed, such as formalin-fixed and paraffin embedded. Samples can be removed from a patient surgically, by extraction (for example by hypodermic or other types of needles), by microdis section, by laser capture, or by any other means known in the art.

ii. Isolating Genomic DNA

Detecting, diagnosing and/or prognosing a malignant adrenocortical tumor in a subject can include isolating genomic DNA. In one example, genomic DNA is isolated from a sample, such as a biological tissue sample, by the methods disclosed in Example 1. For example, genomic total DNA is extracted using a commercially available kit such as DNA STAT-60™ (Tel-Test Inc, Friendswood, Tex.) or DNeasy Blood & Tissue kit (Qiagen, Valencia, Calif.). It is contemplated that additional methods can be used to isolate genomic DNA such as those known to one of ordinary skill in the art. In some examples, the disclosed method also includes assessing the quality of DNA, such as by the method provided in Example 1.

iii. Measuring Methylation of One or More Target Nucleic Acids

Detecting, diagnosing and/or prognosing a malignant adrenocortical tumor in a subject can include measuring the level of one or more methylated genomic CpG dinucleotide sequences in one or more of the genomic targets (such as one or more disclosed malignant adrenocortical tumor-related molecules, such as KCTD12, KIRREL, SYNGR1, NTNG2, GATA6, TP53, β-catenin (CTNNB1), IGF2, H19, IGF1R, AKT1, RARRES2, SLC16A9, IL13RA2, HTR2B, CCNB2 and/or molecules listed in Tables 2-5) in the sample, wherein an increase in the level of methylation of the one or more genomic CpG dinucleotide sequences in the sample compared to a control indicates a malignant adrenocortical tumor.

The presence or absence and/or absolute or relative amount of methylation of one or more target nucleic acids is determined in the sample. Exemplary DNA methylation detection methods include those disclosed in Example 1 as well as, but not limited to, methylation-specific enzyme digestion (Singer-Sam, et al., *Nucleic Acids Res.* 18(3): 687, 1990; Taylor, et al., *Leukemia* 15(4): 583-9, 2001), bisulfite DNA sequencing (Frommer, et al., *Proc Natl Acad Sci USA* 89(5): 1827-31, 1992; Feil, et al., *Nucleic Acids Res.* 22(4): 695-6, 1994), methylation-specific PCR (MSP or MSPCR) (Herman, et al., *Proc Natl Acad Sci USA* 93(18): 9821-6, 1996), methylation-sensitive single nucleotide primer extension (MS-SnuPE) (Gonzalgo, et al., *Nucleic Acids Res.* 25(12): 2529-31, 1997), restriction landmark genomic scanning (RLGS) (Kawai, *Mol Cell Biol.* 14(11): 7421-7, 1994; Akama, et al., *Cancer Res.* 57(15): 3294-9, 1997), and differential methylation hybridization (DMH) (Huang, et al., *Hum Mol Genet.* 8(3): 459-70, 1999). See also the following issued U.S. Pat. Nos. 7,229,759; 7,144,701; 7,125,857; 7,118,868; 6,960,436; 6,905,669; 6,605,432; 6,265,171; 5,786,146; 6,017,704; and 6,200,756; each of which is incorporated herein by reference.

In one particular embodiment, the method includes bi-sulfite converting isolated genomic DNA such as by using the commercially available EZ DNA Methylation Gold Kit (Zymo Research Corporation, Irvine, Calif.) according to the manufacturer's protocol with a modified thermocycling procedure as suggested by Illumina (San Diego, Calif.) (16 cycles of 95° C. 30 sec, 50° C. 60 min). The method further includes measuring the methylation levels by use of BeadArray technology, such as Infinium HumanMethylation450 BeadChips, with the Illumina Infinium HD Methylation Assay Kit (Illumina, Inc, San Diego, Calif.).

In some embodiments, the disclosed methods include detecting methylation of one or more target nucleic acids such as one or more molecules provided in Tables 1-5 (e.g., KCTD12, KIRREL, SYNGR1, NTNG2, RARRES2, SLC16A9, IL13RA2, HTR2B and/or CCNB2 DNA) such as the presence of methylation or an increase in methylation compared to a control in a sample from a subject. In some examples, hypermethylation of one or more molecules provided in Tables 1-5, such as KCTD12, KIRREL, SYNGR1, NTNG2, RARRES2, SLC16A9, IL13RA2, HTR2B and/or CCNB2 in the sample (for example as compared to a control) detects adrenocortical cell proliferative disorder in the subject or diagnoses the subject with a malignant adrenocortical tumor. In particular examples, hypermethylation of one or more target nucleic acids such as one or more molecules provided in Tables 1-4 (e.g., KCTD12, KIRREL, SYNGR1, NTNG2, RARRES2, SLC16A9, IL13RA2, HTR2B and/or CCNB2) includes an increase in methylation of the target sequence by at least 10% (such as at least about 25%, 50%, 75%, 2-fold, 3-fold, 5-fold, 10-fold, or more) as compared to a control, such as a non-tumor sample or a benign tumor sample. In other examples, presence of one or more target nucleic acids methylated in the sample, such as methylation of one or more molecules provided in Tables 2-4 (such as KCTD12, KIRREL, SYNGR1, NTNG2, RARRES2, SLC16A9, IL13RA2, HTR2B and/or CCNB2) detects a adrenocortical cell proliferative disorder in the subject or diagnoses the subject with ACC.

In some examples, methylation of a target nucleic acid, such as methylation of one or more molecules provided in Tables 2-5 (e.g., methylation of KCTD12, KIRREL, SYNGR1, NTNG, RARRES2, SLC16A9, IL13RA2, HTR2B and/or CCNB2 nucleic acid) is detected by hybridization (for example using a microarray, such as disclosed in Example 1), such as hybridization of a methylation-specific probe. In a specific example, DNA is isolated from a sample from a subject and is hybridized with a nucleic acid probe specific for a potentially methylated cytosine residue within the target.

In some examples, methylation of one or more target nucleic acids such as methylation of one or more molecules provided in Tables 2-5 (e.g., KCTD12, KIRREL, SYNGR1, NTNG2, RARRES2, SLC16A9, IL13RA2, HTR2B and/or CCNB2) DNA is detected by methylation-specific polymerase chain reaction (MSPCR). In a specific example, DNA is isolated from a sample from a subject, bisulfite treated, converting all unmethylated, but not methylated, cytosines to uracil, and a region of the KCTD12, KIRREL, SYNGR1, NTNG2, RARRES2, SLC16A9, IL13RA2, HTR2B and/or CCNB2 DNA is amplified with primers that specifically amplify methylated DNA and/or a region of the KCTD12, KIRREL, SYNGR1, NTNG2, RARRES2, SLC16A9, IL13RA2, HTR2B and/or CCNB2 DNA is amplified with primers that specifically amplify unmethylated DNA, thereby detecting methylation (or methylation status) of the KCTD 12, KIRREL, SYNGR1, NTNG2, RARRES2, SLC16A9, IL13RA2, HTR2B and/or CCNB2 gene.

In further examples, methylation of one or more targeted nucleic acids (such as KCTD12, KIRREL, SYNGR1, NTNG, RARRES2, SLC16A9, IL13RA2, HTR2B and/or CCNB2 nucleic acids) is detected using one or more methylation specific restriction endonucleases (such as MspI, HpaII or BssHII). In a particular example, DNA is isolated from a sample from a subject and treated with a restriction endonuclease that recognizes a restriction site within a targeted nucleic acid molecule (such as a KCTD12, KIRREL, SYNGR1, NTNG, RARRES2, SLC16A9, IL13RA2, HTR2B or CCNB2 nucleic acid molecule) and which does not cleave at the restriction site when a cytosine in the restriction site is methylated. In some examples, the method also includes carrying out an amplification reaction (for instance, a PCR amplification reaction) of at least a portion of the target nucleic acid molecule using the resulting treated DNA as a template, wherein the portion of the target nucleic acid contains the restriction site and is amplified only when the restriction site has not been cleaved by the restriction endonuclease.

In some examples, the level of one or more methylated genomic CpG dinucleotide sequences is measured in at least one of, at least two of, at least three of or all four of KCTD12, KIRREL, SYNGR1 and NTNG2.

In some examples, the level of one or more methylated genomic CpG dinucleotide sequences is measured in at least one of, at least two of, at least three of, at least four of or all five of RARRES2, SLC16A9, IL13RA2, HTR2B and CCNB2.

In some examples, the method includes measuring methylation of at least one of, at least two of, at least three of or all four of KCTD12, KIRREL, SYNGR1 and NTNG2 as well as one or more, such as two or more, three or more, four or more, five or more, six or more, seven or more, eight or more other malignant adrenocortical tumor-related molecules, such as GATA6, TP53, β-catenin (CTNNB1), a hypermethylated CpG sites associated with imprinted genes of the chromosome 11p15 locus (such as IGF2 and H19), one or more genes associated with the IGF2 signaling pathway (such as IGF1R and/or AKT1), RARRES2, SLC16A9 or a molecule listed in Table 2. In some examples, the method includes measuring the methylation levels one or more molecules listed in Table 2, including one more molecules associated with (1) Drug Metabolism, Endocrine System Development and Function, Lipid Metabolism (such as ABCA1, CD55, CD74, COL4A3, GOS2, GATA6, HSD3B2, KCNQ1, MAP3K5, NCOA7, RAPGEF4, RARRES2, S100A6, SPTBN1, TNFSF13, and/or TNS1); (2) Lipid Metabolism, Small Molecule Biochemistry, Cell Cycle (such as ADCK3, ALDH3B1, CSDC2, CYP7B1, GIPC2, HOOK1, MEIS1, MLH3, MRPL33, NME5, RGNEF, and/or TCIRG1); (3) Lipid Metabolism, Small Molecule Biochemistry, Energy Production (such as ADCK3, ALDH3B1, CSDC2, CYP7B1, GIPC2, HOOK1, MEIS1, MLH3, MRPL33, NME5, RGNEF, and/or TCIRG1); (4) Lipid Metabolism, Small Molecule Biochemistry, Energy Production (AMPD3, B4GALT6, CAB39L, CD55, GYPC, NDRG4, RAB34, RBPMS, SEMA6A, TNFS1F2 and/or TNFSF13); (5) Cell-To-Cell Signaling and Interaction, Cellular Assembly and Organization, Nervous System Development and Function (SLC16A9); and (6) Hematological Disease, Immunological Disease, Infectious Disease (PHF11).

In some examples, the method includes measuring methylation of at least one of, at least two of, at least three of, at least four of or all five of RARRES2, SLC16A9, IL13RA2, HTR2B and CCNB2 as well as one or more, such as two or more, three or more, four or more, five or more, six or more, seven or more, eight or more other malignant adrenocortical tumor-related molecules, such as GATA6, TP53, β-catenin (CTNNB1), a hypermethylated CpG sites associated with imprinted genes of the chromosome 11p15 locus (such as IGF2 and H19), one or more genes associated with the IGF2 signaling pathway (such as IGF1R and/or AKT1), or a molecule listed in Table 2.

In some examples, the method includes measuring the methylation levels of at least one of, at least two of, at least three of or all four of KCTD12, KIRREL, SYNGR1 and NTNG2 and measuring the methylation levels one or more molecules listed in Table 2, including one more molecules associated with (1) Drug Metabolism, Endocrine System Development and Function, Lipid Metabolism (such as ABCA1, CD55, CD74, COL4A3, GOS2, GATA6, HSD3B2, KCNQ1, MAP3K5, NCOA7, RAPGEF4, RARRES2, S100A6, SPTBN1, TNFSF13, and/or TNS1); (2) Lipid Metabolism, Small Molecule Biochemistry, Cell Cycle (such as ADCK3, ALDH3B1, CSDC2, CYP7B1, GIPC2, HOOK1, MEIS1, MLH3, MRPL33, NME5, RGNEF, and/or TCIRG1); (3) Lipid Metabolism, Small Molecule Biochemistry, Energy Production (such as ADCK3, ALDH3B1, CSDC2, CYP7B1, GIPC2, HOOK1, MEIS1, MLH3, MRPL33, NME5, RGNEF, and/or TCIRG1); (4) Lipid Metabolism, Small Molecule Biochemistry, Energy Production (AMPD3, B4GALT6, CAB39L, CD55, GYPC, NDRG4, RAB34, RBPMS, SEMA6A, TNFS1F2 and/or TNFSF13); (5) Cell-To-Cell Signaling and Interaction, Cellular Assembly and Organization, Nervous System Development and Function (SLC16A9); and (6) Hematological Disease, Immunological Disease, Infectious Disease (PHF11).

In some examples, the method includes measuring methylation of at least one of, at least two of, at least three of, at least four of or all five of RARRES2, SLC16A9, IL13RA2, HTR2B and CCNB2 and measuring the methylation levels one or more molecules listed in Table 2, including one more molecules associated with (1) Drug Metabolism, Endocrine System Development and Function, Lipid Metabolism (such as ABCA1, CD55, CD74, COL4A3, GOS2, GATA6, HSD3B2, KCNQ1, MAP3K5, NCOA7, RAPGEF4, S100A6, SPTBN1, TNFSF13, and/or TNS1); (2) Lipid Metabolism, Small Molecule Biochemistry, Cell Cycle (such as ADCK3, ALDH3B1, CSDC2, CYP7B1, GIPC2, HOOK1, MEIS1, MLH3, MRPL33, NME5, RGNEF, and/or TCIRG1); (3) Lipid Metabolism, Small Molecule Biochemistry, Energy Production (such as ADCK3, ALDII3B1, CSDC2, CYP7B1, GIPC2, HOOK1, MEIS1, MLH3, MRPL33, NME5, RGNEF, and/or TCIRG1); (4) Lipid Metabolism, Small Molecule Biochemistry, Energy Production (AMPD3, B4GALT6, CAB39L, CD55, GYPC, NDRG4, RAB34, RBPMS, SEMA6A, TNFS1F2 and/or TNFSF13); (5) Cell-To-Cell Signaling and Interaction, Cellular Assembly and Organization, Nervous System Development and Function (SLC16A9); and (6) Hematological Disease, Immunological Disease, Infectious Disease (PHF11).

The disclosed methods also include determining the prognosis of a subject with ACC, such as predicting the outcome (for example, likelihood of aggressive disease, recurrence, metastasis, or chance of survival) of the subject. The method includes determining the presence or absence and/or absolute or relative amount of methylation of one or more target nucleic acids (e.g., a KCTD12, KIRREL, SYNGR1, NTNG GATA6, TP53, β-catenin (CTNNB1), IGF2, H19, IGF1R, AKT1, RARRES2, SLC16A9, IL13RA2, HTR2B, CCNB2 nucleic acid and/or nucleic acid listed in Tables 2-5) in the sample, for example, utilizing the methods described above. In some examples, presence of methylation of a target sequence indicates a good prognosis (for example, lower stage cancer or increased likelihood of survival). In an example, an increased chance of survival includes a survival time of at least 60 months from time of diagnosis, such as 60 months, 80 months, 100 months, or more from time of diagnosis or first treatment. In other examples, a good prognosis includes a lower Stage of Cancer (stage 1 and 2 versus 3 and 4) and mitotic count (<9/50 high power field). In some examples, the disclosed method is used as an adjunct to histopathology for localized primary ACC.

a. Methylation Profiling Arrays

The detection of the presence of a particular base can be performed using nucleic acid arrays, such as methylation profiling arrays. For example, an unmethylated allele of a given DNA sequence is expected to have thymine in place of unmethylated cytosine after treatment with a modifying agent and amplification. Similarly, adenine would be in place of guanine in the complementary strand. Conversely, these sequences remain unchanged in a methylated allele. Converted amplified DNA can be hybridized to arrayed oligonucleotide probes specifically designed to discriminate between converted and unconverted nucleotides (or their complement) at sites of interest.

In one embodiment, the presence of particular base is determined with the use of a microarray, such as a methylation profiling array. By way of example, sample DNA is bisulfite treated and amplified (for instance by PCR) for a specific region of interest. The amplified product is labeled with Cy5 fluorescent or another dye and hybridized to one or more oligonucleotide probes attached to a substrate. In some examples, an oligonucleotide probe is designed to form a perfect match with a target DNA containing the unmethylated allele. Likewise, in some examples a probe is designed to form a perfect match with the methylated DNA target. Thus, a microarray, such as a methylation profiling array, can be used to determine the methylation status of a particular cytosine, such as a cytosine in the genomic sequence of a disclosed malignant adrenocortical tumor molecule (such as KCTD12, KIRREL, SYNGR1, NTNG, RARRES2, SLC16A9, IL13RA2, HTR2B and/or CCNB2).

Arrays are arrangements of addressable locations on a substrate, with each address containing a nucleic acid molecule, such as a probe. In some embodiments, each address corresponds to a single type or class of nucleic acid, such as a single probe, though a particular nucleic acid molecule may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, a methylation profiling array is a collection of separate probes at the array addresses. The methylation profiling array is then contacted with a sample of bisulfite treated and amplified nucleic acid molecules for which information about the methylation status of the untreated and unamplified DNA is desired under conditions allowing hybridization between the probe and nucleic acid molecules in the sample to occur. A hybridization signal from an individual address on the array indicates that the probe hybridizes to a nucleotide within the sample. This system permits the simultaneous analysis of a sample by plural probes and yields information about the methylation status of nucleic acid molecules contained within the sample. In alternative embodiments, the array contains bisulfite treated and amplified nucleic acid molecule and the array is contacted with a sample containing a probe. In any such embodiment, either the probe or bisulfite treated and amplified nucleic acid molecule may be labeled to facilitate detection of hybridization.

The nucleic acid molecules may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times to provide an added feature to the array, such as redundant activity or to provide internal controls.

Within an array, each arrayed nucleic acid molecule is addressable, such that its location may be reliably and consistently determined within the at least the two dimensions of the array surface. Thus, ordered arrays allow assignment of the location of each nucleic acid molecule at the time it is placed within the array. Usually, an array map or key is provided to correlate each address with the appropriate nucleic acid molecule. Ordered arrays are often arranged in a symmetrical grid pattern, but nucleic acid molecules could be arranged in other patterns, for example, in radially distributed lines, a "spokes and wheel" pattern, or ordered clusters. Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly, for example, in a Cartesian grid pattern, which can be correlated to address information by a computer.

An address within the array may be of any suitable shape and size. In some embodiments, the nucleic acid molecules are suspended in a liquid medium and contained within square or rectangular wells on the array substrate. However, the nucleic acid molecules may be contained in regions that are essentially triangular, oval, circular, or irregular. The overall shape of the array itself also may vary, though in some embodiments it is substantially flat and rectangular or square in shape.

Methylation profiling arrays may vary in structure, composition, and intended functionality, and may be based on either a macroarray or a microarray format, or a combination thereof. Such arrays can include, for example, at least two, at least three, at least four, at least 10, at least 25, at least 50, at least 100, or more addresses, usually with a single type of nucleic acid molecule at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medical research laboratories, universities, or other institutions without the need for investment in specialized and expensive reading equipment.

Examples of substrates for the arrays disclosed herein include glass, Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible, such as glass or a supported membrane, or flexible, such as a polymer membrane. One commercially available product line suitable for probe arrays described herein is the Microlite line of MICROTITER® plates available from Dynex Technologies UK (Middlesex, United Kingdom), such as the Microlite 1+ 96-well plate, or the 384 Microlite+ 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses, for example, larger addresses will usually be found on larger arrays, while smaller addresses may be found on smaller arrays. Such a correlation is not necessary, however.

The arrays herein may be described by their densities which is the number of addresses in a certain specified surface area. For macroarrays, array density may be about one address per square decimeter, such as one address in a 10 cm by 10 cm region of the array substrate to about 50 addresses per square centimeter. For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the BeadChip products commercially available from Illumina (San Diego, Calif.) or GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid molecule within the sample may be labeled, such as with a fluorescent label and, after hybridization, the hybridization signals may be detected and analyzed.

b. Synthesis of Oligonucleotides

In vitro methods for the synthesis of oligonucleotides are well known to those of ordinary skill in the art; such methods can be used to produce primers and probes for use in the disclosed methods. Such methods can range from standard enzymatic digestion followed by nucleotide fragment isolation (see for example, Sambrook et al., *Molecular Cloning: A Laboratory Manual*, 2nd Edition (Cold Spring Harbor Laboratory Press, Cold Spring Harbor, N.Y., 1989) Chapters 5, 6) to purely synthetic methods, for example, by the cyanoethyl phosphoramidite method. The most common method for in vitro oligonucleotide synthesis is the phosphoramidite method, formulated by Letsinger and further developed by Caruthers (Caruthers et al., *Chemical synthesis of deoxyoligonucleotides,* in *Methods Enzymol.* 154:287-313, 1987). This is a non-aqueous, solid phase reaction carried out in a stepwise manner, wherein a single nucleotide (or modified nucleotide) is added to a growing oligonucleotide. The individual nucleotides are added in the form of reactive 3'-phosphoramidite derivatives. See also, Gait (Ed.), *Oligonucleotide Synthesis. A practical approach,* IRL Press, 1984.

In general, the synthesis reactions proceed as follows: A dimethoxytrityl or equivalent protecting group at the 5' end of the growing oligonucleotide chain is removed by acid treatment. The growing chain is anchored by its 3' end to a solid support such as a silicon bead. The newly liberated 5' end of the oligonucleotide chain is coupled to the 3'-phosphoramidite derivative of the next deoxynucleotide to be added to the chain, using the coupling agent tetrazole. The coupling reaction usually proceeds at an efficiency of approximately 99%; any remaining unreacted 5' ends are capped by acetylation so as to block extension in subsequent couplings. Finally, the phosphite triester group produced by the coupling step is oxidized to the phosphotriester, yielding a chain that has been lengthened by one nucleotide residue. This process is repeated, adding one residue per cycle. See, for example, U.S. Pat. Nos. 4,415,732, 4,458,066, 4,500, 707, 4,973,679, and 5,132,418. Oligonucleotide synthesizers that employ this or similar methods are available commercially (for example, the PolyPlex® oligonucleotide synthesizer from Gene Machines, San Carlos, Calif.). In addition, many companies will perform such synthesis (for example, Sigma-Genosys, The Woodlands, Tex.; QIA-GEN® Operon, Alameda, Calif.; Integrated DNA Technologies, Coralville, Iowa; and TriLink BioTechnologies, San Diego, Calif.).

The nucleotide sequence of an oligonucleotide is generally determined by the sequential order in which subunits or subunit blocks are added to the oligonucleotide chain during synthesis. Each round of addition can involve a different, specific nucleotide precursor or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction. Random hexamer oligonucleotides can be synthesized using standard β-cyanoethyl phosphoramidite coupling chemistry on mixed dA+dC+dG+dT synthesis columns such as those available from Glen Research, Sterling, Va. The four phosphoramidites typically are mixed in equal proportions to randomize the bases at each position in the oligonucleotide.

iv. Providing Diagnosis and/or a Therapeutic Regimen

Following the measurement of the methylation levels of one or more of the molecules identified herein, the results, findings, diagnoses, predictions and/or treatment recommendations can be provided to the subject. For example, the results, findings, diagnoses, predictions and/or treatment recommendations can be recorded and communicated to technicians, physicians and/or patients. In certain embodiments, computers will be used to communicate such information to interested parties, such as, patients and/or the attending physicians. Based on the measurement, the therapy administered to a subject can be started, modified or re-started (in the case of monitoring for a relapse).

In some examples, the output can provide a recommended therapeutic regimen. In some examples, the test may include determination of other clinical information (such as determining the amount of one or more additional adrenocortical cancer biomarkers in the sample).

In some embodiments, the disclosed methods of diagnosis include one or more of the following depending on the patient's diagnosis: a) prescribing a treatment regimen for the patient if the patient's determined diagnosis is considered to be positive for a malignant adrenocortical tumor; b) not prescribing a treatment regimen for the patient if the patient's determined diagnosis is considered to be negative for a malignant adrenocortical tumor; c) administering a treatment to the patient if the patient's determined diagnosis is considered to be positive for a malignant adrenocortical tumor; and d) not administering a treatment regimen to the patient if the patient's determined diagnosis is considered to be negative for a malignant adrenocortical tumor. In an alternative embodiment, the method can include recommending one or more of a)-d).

In one embodiment, a diagnosis, prediction and/or treatment recommendation based on the methylation level of one or more malignant adrenocortical tumor-related molecules disclosed herein is communicated to the subject as soon as possible after the assay is completed and the diagnosis and/or prediction is generated. The results and/or related information may be communicated to the subject by the subject's treating physician. Alternatively, the results may be communicated directly to a test subject by any means of communication, including writing, such as by providing a written report, electronic forms of communication, such as email, or telephone. Communication may be facilitated by use of a computer, such as in case of email communications. In certain embodiments, the communication containing results of a diagnostic test and/or conclusions drawn from and/or treatment recommendations based on the test, may be generated and delivered automatically to the subject using a combination of computer hardware and software which will be familiar to artisans skilled in telecommunications. One example of a healthcare-oriented communications system is described in U.S. Pat. No. 6,283,761; however, the present disclosure is not limited to methods which utilize this particular communications system. In certain embodiments of the methods of the disclosure, all or some of the method steps, including the assaying of samples, diagnosing of diseases, and communicating of assay results or diagnoses, may be carried out in diverse (e.g., foreign) jurisdictions.

In several embodiments, identification of a subject as having a malignant adrenocortical proliferative disorder, such as a malignant adrenocortical tumor results in the physician treating the subject, such as prescribing one or more therapeutic agents for inhibiting or delaying one or more signs and symptoms associated with the disorder/condition and/or surgery. In additional embodiments, the dose or dosing regimen is modified based on the information obtained using the methods disclosed herein.

The subject can be monitored while undergoing treatment using the methods described herein in order to assess the efficacy of the treatment protocol. In this manner, the length of time or the amount given to the subject can be modified based on the results obtained using the methods disclosed herein. The subject can also be monitored after the treatment using the methods described herein to monitor for relapse and thus, the effectiveness of the given treatment. In this manner, whether to resume treatment can be decided based on the results obtained using the methods disclosed herein. In some examples, this monitoring is performed by a clinical healthcare provider.

In some embodiments, the method further includes providing an appropriate therapy for the subject diagnosed with a malignant adrenocortical tumor. In some examples, the therapy includes administering an agent that alters one or more of the malignant adrenocortical tumor-related molecules. For example, the method includes administering a demethylating agent which inhibits or reduces methylation of one or more the disclosed malignant adrenocortical tumor-related molecules that are provided in Table 2.

In some embodiments, a patient with an adrenocortical tumor or suspected of having such can be pre-selected for the treatment and screening methods herein.

In some embodiments, once a patient's diagnosis is determined, an indication of that diagnosis can be displayed and/or conveyed to a clinician or other caregiver. For example, the results of the test are provided to a user (such as a clinician or other health care worker, laboratory personnel, or patient) in a perceivable output that provides information about the results of the test. In some examples, the output is a paper output (for example, a written or printed output), a display on a screen, a graphical output (for example, a graph, chart, voltammetric trace, or other diagram), or an audible output.

In other examples, the output is a numerical value, such as an amount of methylation of one or more disclosed malignant adrenocortical tumor-related molecules in the sample as compared to a control. In additional examples, the output is a graphical representation, for example, a graph that indicates the value (such as amount or relative amount) of methylation of the one or more malignant adrenocortical tumor-related molecules in the sample from the subject on a standard curve. In a particular example, the output (such as a graphical output) shows or provides a cut-off value or level that indicates the presence of a malignant adrenocortical tumor. In some examples, the output is communicated to the user, for example by providing an output via physical, audible, or electronic means (for example by mail, telephone, facsimile transmission, email, or communication to an electronic medical record).

The output can provide quantitative information (for example, an amount of a malignant adrenocortical tumor-related molecule relative to a control sample or value) or can provide qualitative information (for example, a diagnosis of ACC). In additional examples, the output can provide qualitative information regarding the relative amount of methylation of a malignant adrenocortical tumor-related molecule in the sample, such as identifying presence of an increase in methylation relative to a control, a decrease in methylation relative to a control, or no change relative to a control.

In some examples, the output is accompanied by guidelines for interpreting the data, for example, numerical or other limits that indicate the presence or absence of metastasis. The guidelines need not specify whether metastasis is present or absent, although it may include such a diagnosis. The indicia in the output can, for example, include normal or abnormal ranges or a cutoff, which the recipient of the output may then use to interpret the results, for example, to arrive at a diagnosis, prognosis, or treatment plan.

IV. Methods of Treating a Malignant Adrenocortical Tumor

Also provided herein is a method of treating a patient with a malignant adrenocortical tumor, including ACC, by administering to the subject with a malignant adrenocortical tumor an effective amount of an agent, such as a demethylating agent, that alters the activity and/or expression of one or more disclosed malignant adrenocortical tumor molecules, such as one or more molecules listed in any one of Tables 2-4, thereby treating the malignant adrenocortical tumor.

In some embodiments, the method further includes selecting a subject with a malignant adrenocortical tumor prior to administering the treatment.

In some embodiments, selecting a subject with a malignant adrenocortical tumor comprises detecting methylation and mRNA expression of one or more malignant adrenocortical tumor molecules listed in any one of Tables 2-5, whereby an increase in methylation and a decrease in mRNA expression of the one or more malignant adrenocortical tumor molecules indicate the subject has a malignant adrenocortical tumor.

In some embodiments, the one or more malignant adrenocortical tumor molecules includes H19, S100A10, HOPX, ERBB3, and/or RUNX2.

In some embodiments, the method of treatment is a method of treating ACC. In some embodiments, the method of treatment further includes administering one or more additional anti-cancer agents or therapeutic treatments (such as surgical resection of a tumor or radiation therapy).

i. Selecting a Subject

The disclosed methods for treating a malignant adrenocortical tumor can include selecting a subject with a malignant adrenocortical tumor. In some examples, a subject is selected by screening the subject for a malignant adrenocortical tumor prior to administering a disclosed treatment. In some examples, identification of subjects with the same medical condition, such as a malignant adrenocortical tumor, including ACC, can be accomplished by selecting all patients with the same diagnosis within electronic health records (EHR). EHRs are simply individual health records in a digitized format that can be accessed via a computer or computer-based system over a network. EHRs are designed to keep information about each encounter with the patient. For example, EHRs may include a person's health characteristics, medical history, past and current diagnoses, lab reports and results, x-rays, photographs, prescribed medication, billing and insurance information, contact information, demographics, and the like.

In particular examples, the subject is screened to determine if the adrenocortical tumor is malignant, indicating ACC, or benign. Examples of methods that can be used to screening for ACC include those described herein for diagnosing a subject with a malignant adrenocortical tumor as well as histological, ultrasound or serum blood levels analyses. If blood or a fraction thereof (such as serum) is used, 1-100 µl of blood is collected. Serum can either be used directly or fractionated using filter cut-offs to remove high molecular weight proteins. If desired, the serum can be frozen and thawed before use. If a tissue biopsy sample is used, 1-100 µg of tissue is obtained, for example using a fine needle aspirate. The biological sample (e.g., tissue biopsy or serum) is analyzed to determine both the methylation state and expression level of one or more malignant adrenocortical tumor-molecules, wherein the presence of an increased/hypermethylated and downregulated molecule listed in Table 2 indicates that the tumor is malignant and further that it can be treated with the disclosed therapies.

The disclosed method of treating a malignant adrenocortical tumor can include selecting a subject for treatment by determining methylation levels and expression levels of one or more malignant adrenocortical tumor-related molecules, such as one or more molecules listed in Table 2. In some embodiments of the methods provided herein, mRNA expression profiles in combination with methylation profiles are used to diagnose malignant adrenocortical tumors and to identify the subject as a candidate to receive a disclosed therapy.

As described below, expression of one or more mRNAs associated with a malignant adrenocortical tumor can be detected using any one of a number of methods. The disclosed methods can include measuring methylation of one or more of the disclosed malignant adrenocortical tumor-related genes, such as one or more genes listed in Table 2 by methods described previously herein as well as in the Example Section.

In some embodiments, the methods provided herein further include evaluating expression of mRNA, such as the expression of one or more of the mRNA molecules associated a malignant adrenocortical tumor-related gene (such as those mRNAs of the genes listed in Table 2), In some examples, the mRNAs are quantified. Detection and quantification of mRNA expression can be achieved by any one of a number of methods including those described herein (such as Example 1). General methods for mRNA extraction are disclosed in textbooks of molecular biology, including Ausubel et al., Current Protocols of Molecular Biology, John Wiley and Sons (1997). Using the known sequences for mRNA of interest, specific probes and primers can be designed for use in the detection methods described herein as appropriate.

In some cases, the mRNA detection method requires isolation of nucleic acid from a sample, such as a cell, biological fluid sample or tissue sample (for example, a tissue biopsy from the adrenal cortex). Nucleic acids, including RNA and specifically mRNA, can be isolated using any suitable technique known in the art. For example, phenol-based extraction is a common method for isolation of RNA. Phenol-based reagents contain a combination of denaturants and RNase inhibitors for cell and tissue disruption and subsequent separation of RNA from contaminants. Phenol-based isolation procedures can recover RNA species in the 10-200-nucleotide range (e.g., precursor and mature miRNAs, 5S and 5.8S ribosomal RNA (rRNA), and U1 small nuclear RNA (snRNA)). In addition, extraction procedures such as those using TRIZOL™ or TRI REAGENT™, will purify all RNAs, large and small, and are efficient methods for isolating total RNA from biological samples that contain mRNA, miRNAs and siRNAs.

Microarray analysis of mRNAs can be accomplished according to method disclosed in Example 1 as well PCT Publication No. WO 2008/054828; Ye et al., Nat. Med. 9(4):416-423, 2003; Calin et al., N. Engl. J. Med. 353(17): 1793-1801, 2005). Methods for detecting expression of a gene of interest (including mRNAs) include qRT-PCR, array, microarray, in situ hybridization, in situ PCR, and SAGE which are described in further detail below.

a. RT-PCR

In some embodiments, methods for quantitating mRNA include RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). However, any suitable reverse transcriptase known in the art can be used for RT-PCR. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA), following the manufacturer's instructions. The derived cDNA can then be used as a template in the subsequent PCR reaction.

Although the PCR step can use a variety of thermostable DNA-dependent DNA polymerases, it often employs the Taq DNA polymerase, which has a 5'-3' nuclease activity but lacks a 3'-5' proofreading endonuclease activity. TaqMan® PCR typically utilizes the 5'-nuclease activity of Taq or Tth DNA polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

To minimize errors and the effect of sample-to-sample variation, RT-PCR can be performed using an internal standard. The ideal internal standard is expressed at a constant level among different tissues, and is unaffected by the experimental treatment. RNAs commonly used to normalize patterns of gene expression are mRNAs for the housekeeping genes glyceraldehyde-3-phosphate-dehydrogenase (GAPDH), beta-actin, and 18S ribosomal RNA.

The steps of a representative protocol for quantitating gene expression using fixed, paraffin-embedded tissues as the RNA source, including RNA isolation, purification, primer extension and amplification are given in various published journal articles (see Godfrey et al., *J. Mol. Diag.* 2:84 91, 2000; Specht et al., *Am. J. Pathol.* 158:419-29, 2001). Briefly, a representative process starts with cutting about 10 µm thick sections of paraffin-embedded tissue samples. The RNA is then extracted, and protein and DNA are removed. Alternatively, RNA is located directly from a tissue, cell or fluid sample. After analysis of the RNA concentration, RNA repair and/or amplification steps can be included, if necessary, and RNA is reverse transcribed using gene specific promoters followed by RT-PCR. The primers used for the amplification are selected so as to amplify a unique segment of the gene of interest, such as a mRNA. Primers that can be used to amplify a particular mRNA are commercially available (in some instance) or can be designed and synthesized using publically available sequences of the mRNA.

b. Serial Analysis of Gene Expression (SAGE)

SAGE is another method that allows the simultaneous and quantitative analysis of a large number of gene transcripts, without the need of providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag (see, for example, Velculescu et al., *Science* 270:484-7, 1995; and Velculescu et al., *Cell* 88:243-51, 1997).

c. In Situ Hybridization (ISH)

ISH is another method for detecting and comparing expression of genes of interest. ISH applies and extrapolates the technology of nucleic acid hybridization to the single cell level, and, in combination with the art of cytochemistry, immunocytochemistry and immunohistochemistry, permits the maintenance of morphology and the identification of cellular markers to be maintained and identified, and allows the localization of sequences to specific cells within populations, such as tissues and blood samples. ISH is a type of hybridization that uses a complementary nucleic acid to localize one or more specific nucleic acid sequences in a portion or section of tissue (in situ), or, if the tissue is small enough, in the entire tissue (whole mount ISH). RNA ISH can be used to assay expression patterns in a tissue, such as the expression of mRNA.

Sample cells or tissues are treated to increase their permeability to allow a probe, such as a mRNA-specific probe, to enter the cells. The probe is added to the treated cells, allowed to hybridize at pertinent temperature, and excess probe is washed away. A complementary probe is labeled with a radioactive, fluorescent or antigenic tag, so that the probe's location and quantity in the tissue can be determined using autoradiography, fluorescence microscopy or immunoassay. The sample may be any sample as herein described, such as a adrenal cortex tissue sample. Since the sequences of the mRNAs of interest are known, probes can be designed accordingly such that the probes specifically bind the gene of interest.

d. In Situ PCR

In situ PCR is the PCR based amplification of the target nucleic acid sequences prior to ISH. For detection of RNA, an intracellular reverse transcription step is introduced to generate complementary DNA from RNA templates prior to in situ PCR. This enables detection of low copy RNA sequences.

Prior to in situ PCR, cells or tissue samples are fixed and permeabilized to preserve morphology and permit access of the PCR reagents to the intracellular sequences to be amplified. PCR amplification of target sequences is next performed either in intact cells held in suspension or directly in cytocentrifuge preparations or tissue sections on glass slides. In the former approach, fixed cells suspended in the PCR reaction mixture are thermally cycled using conventional thermal cyclers. After PCR, the cells are cytocentrifuged onto glass slides with visualization of intracellular PCR products by ISH or immunohistochemistry. In situ PCR on glass slides is performed by overlaying the samples with the PCR mixture under a coverslip which is then sealed to prevent evaporation of the reaction mixture. Thermal cycling is achieved by placing the glass slides either directly on top of the heating block of a conventional or specially designed thermal cycler or by using thermal cycling ovens.

Detection of intracellular PCR products is generally achieved by one of two different techniques, indirect in situ PCR by ISH with PCR-product specific probes, or direct in situ PCR without ISH through direct detection of labeled nucleotides (such as digoxigenin-11-dUTP, fluorescein-dUTP, 3H-CTP or biotin-16-dUTP), which have been incorporated into the PCR products during thermal cycling.

e. Arrays for Profiling mRNA Expression

In particular embodiments provided herein, arrays can be used to evaluate mRNA expression, for example to diagnose or prognose adrenocortical tumors, including ACC. When describing an array that comprises probes or primers specific for a particular set of mRNAs, such an array includes probes or primers specific for the recited mRNAs (such as those provided in Table 2), and can further include control probes (for example to confirm the incubation conditions are sufficient). Exemplary control probes include GAPDH, RNU48, actin, and YWHAZ. In one example, an array is a multi-well plate (e.g., 98 or 364 well plate).

In one example, the array includes, consists essentially of, or consists of probes or primers that can recognize the mRNAs listed in Table 2 and a control probe. In some examples, the array includes, consists essentially of, or consists of probes or primers that can recognize the mRNAs listed in Table 2 The oligonucleotide probes or primers can further include one or more detectable labels, to permit detection of hybridization signals between the probe and target sequence (such as one of the microRNAs disclosed herein).

1. Array Substrates

The solid support of the array can be formed from an organic polymer. Suitable materials for the solid support include, but are not limited to: polypropylene, polyethylene, polybutylene, polyisobutylene, polybutadiene, polyisoprene, polyvinylpyrrolidine, polytetrafluroethylene, polyvinylidene difluroide, polyfluoroethylene-propylene, polyethylenevinyl alcohol, polymethylpentene, polycholorotrifluoroethylene, polysulfornes, hydroxylated biaxially oriented polypropylene, aminated biaxially oriented polypropylene, thiolated biaxially oriented polypropylene, etyleneacrylic acid, thylene methacrylic acid, and blends of copolymers thereof (see U.S. Pat. No. 5,985,567).

In general, suitable characteristics of the material that can be used to form the solid support surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by the oligonucleotides or proteins (such as antibodies) are not amenable to non-specific binding, or when non-specific binding occurs, such materials can be readily removed from the surface without removing the oligonucleotides or proteins (such as antibodies).

In one example, the solid support surface is polypropylene. Polypropylene is chemically inert and hydrophobic. Non-specific binding is generally avoidable, and detection sensitivity is improved. Polypropylene has good chemical resistance to a variety of organic acids (such as formic acid), organic agents (such as acetone or ethanol), bases (such as sodium hydroxide), salts (such as sodium chloride), oxidizing agents (such as peracetic acid), and mineral acids (such as hydrochloric acid). Polypropylene also provides a low fluorescence background, which minimizes background interference and increases the sensitivity of the signal of interest.

In another example, a surface activated organic polymer is used as the solid support surface. One example of a surface activated organic polymer is a polypropylene material aminated via radio frequency plasma discharge. Such materials are easily utilized for the attachment of nucleotide molecules. The amine groups on the activated organic polymers are reactive with nucleotide molecules such that the nucleotide molecules can be bound to the polymers. Other reactive groups can also be used, such as carboxylated, hydroxylated, thiolated, or active ester groups.

2. Array Formats

A wide variety of array formats can be employed in accordance with the present disclosure. One example includes a linear array of oligonucleotide bands, generally referred to in the art as a dipstick. Another suitable format includes a two-dimensional pattern of discrete cells (such as 4096 squares in a 64 by 64 array). As is appreciated by those skilled in the art, other array formats including, but not limited to slot (rectangular) and circular arrays are equally suitable for use (see U.S. Pat. No. 5,981,185). In some examples, the array is a multi-well plate. In one example, the array is formed on a polymer medium, which is a thread, membrane or film. An example of an organic polymer medium is a polypropylene sheet having a thickness on the order of about 1 mil. (0.001 inch) to about 20 mil., although the thickness of the film is not critical and can be varied over a fairly broad range. The array can include biaxially oriented polypropylene (BOPP) films, which in addition to their durability, exhibit a low background fluorescence.

The array formats of the present disclosure can be included in a variety of different types of formats. A "format" includes any format to which the solid support can be affixed, such as microtiter plates (e.g., multi-well plates), test tubes, inorganic sheets, dipsticks, and the like. For example, when the solid support is a polypropylene thread, one or more polypropylene threads can be affixed to a plastic dipstick-type device; polypropylene membranes can be affixed to glass slides. The particular format is, in and of itself, unimportant. All that is necessary is that the solid support can be affixed thereto without affecting the functional behavior of the solid support or any biopolymer absorbed thereon, and that the format (such as the dipstick or slide) is stable to any materials into which the device is introduced (such as clinical samples and hybridization solutions).

The arrays of the present disclosure can be prepared by a variety of approaches. In one example, oligonucleotide sequences are synthesized separately and then attached to a solid support (see U.S. Pat. No. 6,013,789). In another example, sequences are synthesized directly onto the support to provide the desired array (see U.S. Pat. No. 5,554,501). Suitable methods for covalently coupling oligonucleotides to a solid support and for directly synthesizing the oligonucleotides onto the support are known to those working in the field; a summary of suitable methods can be found in Matson et al., *Anal. Biochem.* 217:306-10, 1994. In one example, the oligonucleotides are synthesized onto the support using conventional chemical techniques for preparing oligonucleotides on solid supports (such as see PCT applications WO 85/01051 and WO 89/10977, or U.S. Pat. No. 5,554,501).

A suitable array can be produced using automated means to synthesize oligonucleotides in the wells of the array by laying down the precursors for the four bases in a predetermined pattern. Briefly, a multiple-channel automated chemical delivery system is employed to create oligonucleotide probe populations in parallel rows (corresponding in number to the number of channels in the delivery system) across the substrate. Following completion of oligonucleotide synthesis in a first direction, the substrate can then be rotated by 90° to permit synthesis to proceed within a second (2°) set of rows that are now perpendicular to the first set. This process creates a multiple-channel array whose intersection generates a plurality of discrete cells.

The oligonucleotides can be bound to the polypropylene support by either the 3' end of the oligonucleotide or by the 5' end of the oligonucleotide. In one example, the oligonucleotides are bound to the solid support by the 3' end. However, one of skill in the art can determine whether the use of the 3' end or the 5' end of the oligonucleotide is suitable for bonding to the solid support. In general, the internal complementarity of an oligonucleotide probe in the region of the 3' end and the 5' end determines binding to the support.

In particular examples, the oligonucleotide probes on the array include one or more labels, that permit detection of oligonucleotide probe:target sequence hybridization complexes.

f. Output of mRNA Gene Expression Analysis Results

Gene expression can be evaluated using any technique described above, or any other method known in the art. As described herein, gene expression can be measured, for example, using labeled probes that can be detected using standard equipment. For example, gene expression measurements using microarray or RT-PCR (which typically use labeled probes specific for a gene product) can be quantitated using a microarray scanner or other suitable scanner for detecting the label. In some embodiments, the device used to measure gene expression is a microarray scanner.

Microarray scanners are well known and are commercially available, such as the Model G250GB Microarray Scanner from Agilent Technologies.

The results of gene expression analysis can be transmitted using any one of a number of output devices or formats known in the art. For example, the output device can be a visual output device, such as a computer screen or a printed piece of paper. In other examples, the output device can be an auditory output device, such as a speaker. In other examples, the output device is a printer. In some cases, the data is recorded in a patient's electronic medical record.

ii. Agents

It is contemplated that any agent which modulates the expression level of one or more of the disclosed malignant adrenocortical tumor-related molecules can be administered to a subject to treat a malignant adrenocortical tumor. In some examples, the administered agent is a demethylating agent which inhibits or reduces methylation, resulting in the expression of the previously hypermethylated, but down-regulated (silenced) genes, such as one or more of the genes listed in Tables 2-4. In some examples, the administered demethylating agent is a histone deacetylase inhibitor. In some examples, the administered demethylating agent is a second-generation histone deacetylase inhibitor, such as a hydroxamic acid (e.g., vorinostat, belinostat, panobinostat), or a benzamide (e.g., entinostat, mocetinostat). In some examples, an administered demethylating agent is a cytidine analog such as 5-azacytidine (azacitidine) and 5-azadeoxy-cytidine (decitabine). Cytidine analogs bind to DNA methyltransferases that catalyse the methylation reaction and titrate out these enzymes. Azacitidine and decitabine are marketed as Vidaza and Dacogen, respectively. In some examples, procaine is administered.

In some examples, an administered agent is a methylating agent that specifically modulates one or more disclosed malignant adrenocortical tumor-related molecules hypomethylated in malignant adrenocortical tumors, while not significantly altering the methylation status of other malignant adrenocortical tumor-related molecules (such as those indicated as hypermethylated).

iii. Administration of Agents

Agents can be administered to a subject in need of treatment using any suitable means known in the art. Methods of administration include, but are not limited to, intraductal, intradermal, intramuscular, intraperitoneal, parenteral, intravenous, subcutaneous, vaginal, rectal, intranasal, inhalation, oral or by gene gun. Intranasal administration refers to delivery of the compositions into the nose and nasal passages through one or both of the nares and can comprise delivery by a spraying mechanism or droplet mechanism, or through aerosolization of the nucleic acid or virus. Administration of an agent by inhalant can be through the nose or mouth via delivery by spraying or droplet mechanisms. Delivery can be directly to any area of the respiratory system via intubation. Parenteral administration is generally achieved by injection. Injectables can be prepared in conventional forms, either as liquid solutions or suspensions, solid forms suitable for solution of suspension in liquid prior to injection, or as emulsions. Injection solutions and suspensions can be prepared from sterile powders, granules, and tablets. Administration can be systemic or local.

Agents can be administered in any suitable manner, preferably with pharmaceutically acceptable carriers. Pharmaceutically acceptable carriers are determined in part by the particular composition being administered, as well as by the particular method used to administer the composition. Accordingly, there is a wide variety of suitable formulations of pharmaceutical compositions of the present disclosure.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Administration can be accomplished by single or multiple doses. The dose required will vary from subject to subject depending on the species, age, weight and general condition of the subject, the particular therapeutic agent being used and its mode of administration. For example, an effective amount of an agent to treat a malignant adrenocortical tumor can be based on the approximate body weight of a subject to be treated. Such effective amounts can be administered by any suitable route, such as, for example, parenterally or enterally. In some examples, an effective amount of the agent is administered to a subject can range from about 5 to about 3000 micrograms/kg of body weight, from about 700 to about 1000 micrograms/kg of body weight, or greater than about 1000 micrograms/kg of body weight.

An appropriate dosage regimen for the administration of the agent to a given subject is one in which the agent reduces one or more signs or symptoms of a malignant adrenocortical tumor. In some examples, the can be administered to the subject once (e.g., as a single injection or deposition). Alternatively, the agent can be administered once or twice daily to a subject for a period of from about three to about twenty-eight days, more particularly from about seven to about ten days. In a particular dosage regimen, the agent is administered once a day for seven days. Where a dosage regimen comprises multiple administrations, it is understood that the effective amount of the agent administered to the subject can comprise the total amount of agent administered over the entire dosage regimen.

Appropriate doses of small molecule agents depend upon a number of factors known to those or ordinary skill in the art, e.g., a physician. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

iv. Combination Treatment Methods

The disclosed methods for treating malignant adrenocortical tumors can be used alone or can be accompanied by administration of other agents, such as anti-cancer agents, or therapeutic treatments (such as surgical resection of a tumor or radiation therapy). Any suitable anti-cancer agent can be administered to a patient as part of a treatment regimen that includes inhibiting or treating a malignant adrenocortical tumor. Exemplary anti-cancer agents include, but are not limited to, chemotherapeutic agents, such as, for example, mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones (e.g. anti-androgens) and anti-angiogenesis agents. Other anti-cancer treatments include radiation therapy and antibodies that specifically target cancer cells.

Examples of alkylating agents include nitrogen mustards (such as mechlorethamine, cyclophosphamide, melphalan, uracil mustard or chlorambucil), alkyl sulfonates (such as busulfan), nitrosoureas (such as carmustine, lomustine, semustine, streptozocin, or dacarbazine).

Examples of antimetabolites include folic acid analogs (such as methotrexate), pyrimidine analogs (such as 5-FU or cytarabine), and purine analogs, such as mercaptopurine or thioguanine.

Examples of natural products include vinca alkaloids (such as vinblastine, vincristine, or vindesine), epipodophyllotoxins (such as etoposide or teniposide), antibiotics (such as dactinomycin, daunorubicin, doxorubicin, bleomycin, plicamycin, or mitocycin C), and enzymes (such as L-asparaginase).

Examples of miscellaneous agents include platinum coordination complexes (such as cis-diamine-dichloroplatinum II also known as cisplatin), substituted ureas (such as hydroxyurea), methyl hydrazine derivatives (such as procarbazine), and adrenocrotical suppressants (such as mitotane and aminoglutethimide).

Examples of hormones and antagonists include adrenocorticosteroids (such as prednisone), progestins (such as hydroxyprogesterone caproate, medroxyprogesterone acetate, and magestrol acetate), estrogens (such as diethylstilbestrol and ethinyl estradiol), antiestrogens (such as tamoxifen), and androgens (such as testerone proprionate and fluoxymesterone).

Examples of many of the most commonly used chemotherapy drugs include Adriamycin, Alkeran, Ara-C, BiCNU, Busulfan, CCNU, Carboplatinum, Cisplatinum, Cytoxan, Daunorubicin, DTIC, 5-FU, Fludarabine, Hydrea, Idarubicin, Ifosfamide, Methotrexate, Mithramycin, Mitomycin, Mitoxantrone, Nitrogen Mustard, Taxol (or other taxanes, such as docetaxel), Velban, Vincristine, VP-16, while some more newer drugs include Gemcitabine (Gemzar), Herceptin, Irinotecan (Camptosar, CPT-11), Leustatin, Navelbine, Rituxan STI-571, Taxotere, Topotecan (Hycamtin), Xeloda (Capecitabine), Zevelin and calcitriol.

In some examples, the chemotherapy regimen includes mitotane (an inhibitor of steroid synthesis which is toxic to cells of the adrenal cortex) as well as standard cytotoxic drugs. For example, an exemplary regimen consists of cisplatin, doxorubicin, etoposide, and mitotane. In some examples, the endocrine cell toxin streptozotocin is included with the chemotherapeutic. In further examples, hormonal therapy with steroid synthesis inhibitors such as aminoglutethimide is used in a palliative manner to reduce the symptoms of hormonal syndromes associated with the ACC.

When used in combination with the administration of one of the disclosed therapeutic agents targeting one or more molecules associated with a malignant adrenocortical tumor (e.g., associated with ACC), the additional treatment methods described above can be administered or performed prior to, at the same time, or following the disclosed anti-tumor therapy as appropriate for the particular patient, the additional symptoms associated with the ACC (e.g., hormonal symptoms, conditions and related diseases) and the specific combination of therapies.

The following examples are provided to illustrate certain particular features and/or embodiments. These examples should not be construed to limit the invention to the particular features or embodiments described.

EXAMPLES

Example 1

Materials and Methods

This example provides the Materials and Methods utilized in Examples 2-7.

Tissue Samples

Adrenocortical tissue samples were collected as described previously. Eighty-seven tissue samples were obtained at surgical resection and were immediately snap frozen and stored at −80° C. Normal adrenal glands were obtained at the time of nephrectomy for organ donation and immediately snap frozen and stored at −80° C. Demographic, clinical and pathological information were collected after written informed consent under an Institutional Review Board (IRB) approved protocol. Tumors were classified as adrenocortical carcinoma when there was gross local invasion or distant metastasis was present at diagnosis or developed during follow up. Benign adrenocortical tissue samples were classified if the tumor was localized at presentation and there was no evidence of local or distant recurrent disease after follow up of an average of 2.1 years (range 1-10 years) (Table 1).

TABLE 1

Clinical features of tissue samples used for methylation profiling.

|  | Benign Tumor | Primary Tumor | Metastatic Tumor |
|---|---|---|---|
| Number of Samples | 48 | 8 | 12 |
| Age y, mean ± SEM* | 48.9 ± 1.0 | 42.3 ± 5.3 | 57.2 ± 4.8 |

TABLE 1-continued

Clinical features of tissue samples used for methylation profiling.

|  | Benign Tumor | Primary Tumor | Metastatic Tumor |
| --- | --- | --- | --- |
| Gender women/men | 35/13 | 5/3 | 11/1 |
| Type of Tumor | 48 primary | 8 primary | 7 locoregional recurrence, 2 liver metastases, 2 lung metastases, 1 abdominal wall metastasis |
| Syndrome | | | |
| Hypercortisolism | 16 | 6 | 7 |
| Hyperaldosteronism | 16 | 0 | 0 |
| Nonfunctioning | 16 | 2 | 5 |

*SEM: Standard Error of the Mean

Methylation Profiling of Tissue Samples

Frozen adrenocortical tissue was sectioned for DNA isolation and total DNA was extracted using DNA STAT-60 (Tel-Test Inc, Friendswood, Tex.) or DNeasy Blood & Tissue kit (Qiagen, Valencia, Calif.). DNA quality was determined using a NanoDrop 2000c spectrophotometer (Thermo Fisher Scientific Inc, Wilmington, Del.).

One μg of DNA was bisulfite-converted using the EZ DNA Methylation Gold Kit (Zymo Research Corporation, Irvine, Calif.) according to the manufacturer's protocol with a modified thermocycling procedure as suggested by Illumina (San Diego, Calif.) (16 cycles of 95° C. 30 sec, 50° C. 60 min). Four μl (~600 ng) of the bisulfite converted DNA was assayed on Infinium HumanMethylation450 BeadChips using the Illumina Infinium HD Methylation Assay Kit (Illumina, Inc, San Diego, Calif.). These chips assess the methylation status at >485,000 individual CpG sites encompassing 99% of RefSeq genes and 96% of CpG islands. Each DNA sample first underwent an overnight isothermal whole genome amplification step. Amplified DNA was fragmented, precipitated, and resuspended. Samples were hybridized to BeadChips overnight at 48° C. in an Illumina Hybridization Oven. Using an automated protocol on the Tecan Evo robot (Tecan Group Ltd, Mannedorf, Switzerland), hybridized arrays were processed through a single-base extension reaction on the probe sequence using DNP- or biotin-labeled nucleotides, with subsequent immunostaining. The BeadChips were then coated, dried, and imaged on an Illumina HiScanSQ (Illumina Inc, San Diego, Calif.). Image data was extracted using the Genome Studio v2010.3 Methylation module. Beta-values were calculated at each locus (β=Intensity of methylated allele/intensity of unmethylated allele+intensity of methylated allele+100) followed by analysis with R package to normalize the data. The X and Y chromosomes' methylation data were excluded from the results. QC inclusion valuation depended on hybridization detection p-values of less than 0.05. One benign sample failed to meet quality control (QC) standards and was thus excluded from subsequent data analysis.

mRNA Microarray of Tissue Samples

Frozen adrenocortical tissue was sectioned for RNA isolation, and a serial section was stained using hematoxylin-eosin to confirm diagnosis and tumor content of greater than 80%, Total RNA was extracted from homogenized frozen tissue using Trizol reagent (Invitrogen, Carlsbad, Calif.) and was purified using an RNeasy Mini Kit (Qiagen, Valencia, Calif.). One μg of total RNA was used for amplification and labeling with the MessageAmp aRNA kit (Ambion Inc, Foster City, Calif.). Fragmented and labeled complementary RNA (12 μg) was hybridized to a gene chip (Affymetrix Human Genome U133 plus 2.0 GeneChip; Affymetrix Inc, Santa Clara, Calif.) for16 hours at 45° C. The gene chip arrays were stained and washed (Affymetrix Fluidics Station 400; Affymetrix Inc) according to the manufacturer's protocol. The probe intensities were measured using an argon laser confocal scanner (GeneArray scanner; Hewlitt-Packard, Palo Alto, Calif.).

Data and Statistical Analyses

Data analysis for the mRNA microarrays was carried out using the Affymetrix GeneChip Operating Software (Affymetrix Inc, Santa Clara, Calif.) to process the raw microarray data. To generate intensity values in the log2 scale, R/Bioconductor statistics were used for each probe set using the robust multiarray average method with default variables. For the class comparison (benign vs. malignant), the limina package in R/Bioconductor was used to calculate the moderated t statistics and the associated P values and the log posterior odds ratio (B statistic) that a gene is differentially expressed compared to not differentially expressed. The P values were adjusted for multiple testing by controlling for the false discovery rate using the Benjamini-Hochberg method.

Data analysis for the methylation BeadChip arrays was carried out by extracting image data using the Genome Studio v2010.3 Methylation module. Beta-values were calculated at each locus followed by analysis with R package and Partek software (Partek Inc, St. Louis, Mo.). For the comparison of the different tissue type groups, ANOVA was used based on the M-values converted from corresponding beta values from each locus and p values were adjusted for multiple testing by controlling for false discovery rate using the Benjamini-Hochberg method. Pathway and biological function analysis was conducted using Ingenuity Pathway Analysis software (Ingenuity Systems Inc, Redwood City, Calif.).

Example 2

Methylation Profile of Human Adrenocortical Tissue Samples

This example demonstrates the methylation profile of human adrenocortical tissue samples.

Unsupervised hierarchical cluster analysis was performed on 19 normal, 47 benign, 8 primary malignant and 12 metastatic tissue samples. Primary malignant ACC and metastatic tissue samples were globally hypomethylated compared to normal and benign tissue samples (adjusted p-value of p≤0.01).

Figure 1B:
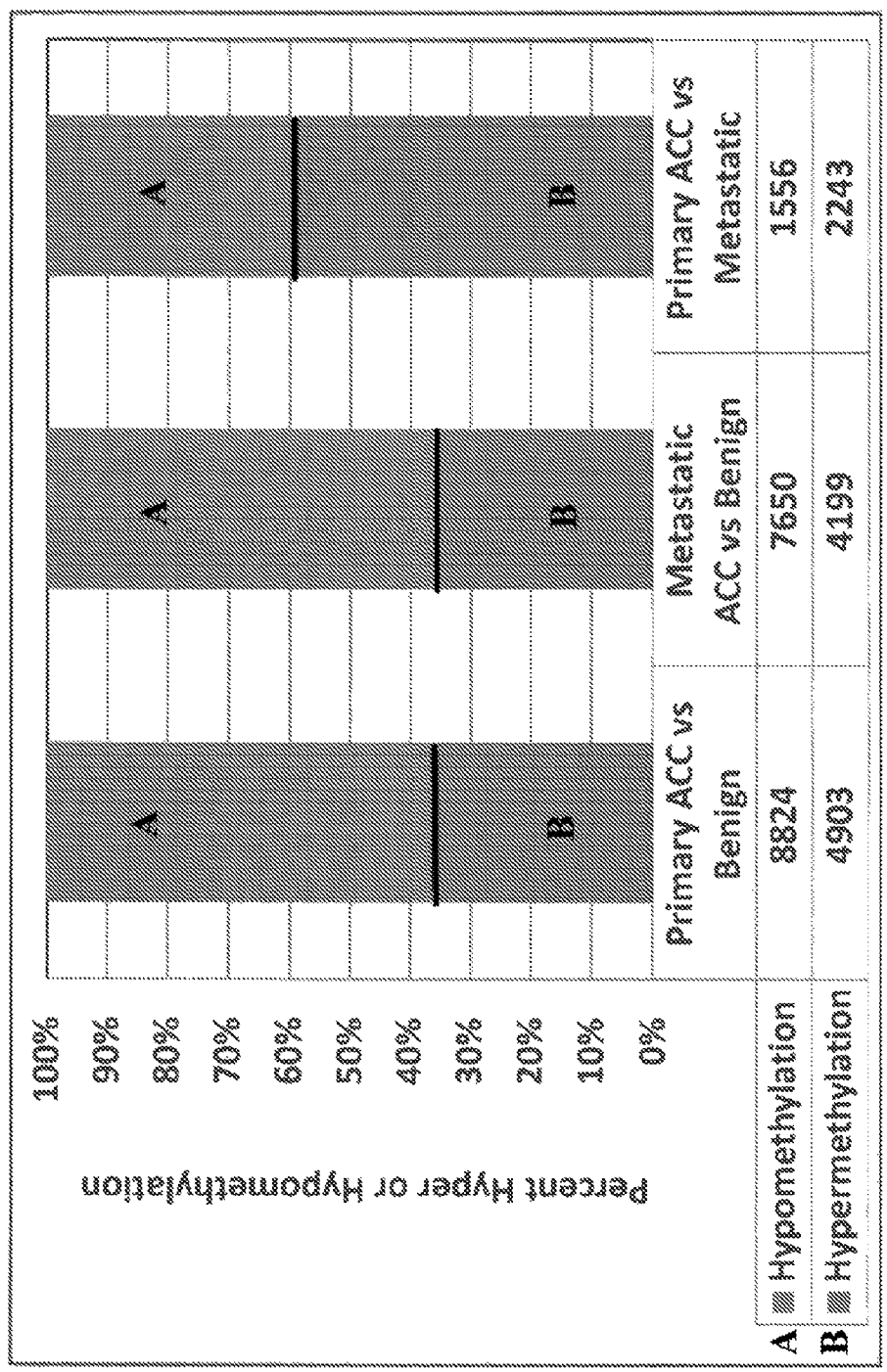

Differentially methylated sites were found in both coding and noncoding regions of DNA. Using an adjusted p≤0.01 and beta value differences of $\Delta\beta \leq -0.20$ or $\Delta\beta \geq 0.20$, the smallest methylation differences were found between normal and benign tissue samples (104 total differentially methylated sites), 67.3% of which were hypermethylated in benign tissue samples. The largest differences were between primary and metastatic ACC samples compared to normal tissue samples (24,229 and 21,736 differentially methylated sites, respectively), and these were 81.3% and 80.8% hypomethylated in the malignant tissue samples (FIG. 1A). The next largest differences in methylation patterns were between primary and metastatic ACC samples compared to benign tissue samples (13,727 sites and 11,849 differentially methylated sites respectively), and these sites were 64.3% and 64.6% hypomethylated in the malignant tissue samples. In contrast, primary ACC samples compared to metastatic samples had only 3,799 differentially methylated sites and these were 59.0% hypermethylated in primary ACC samples (FIG. 1B).

Figure 2:
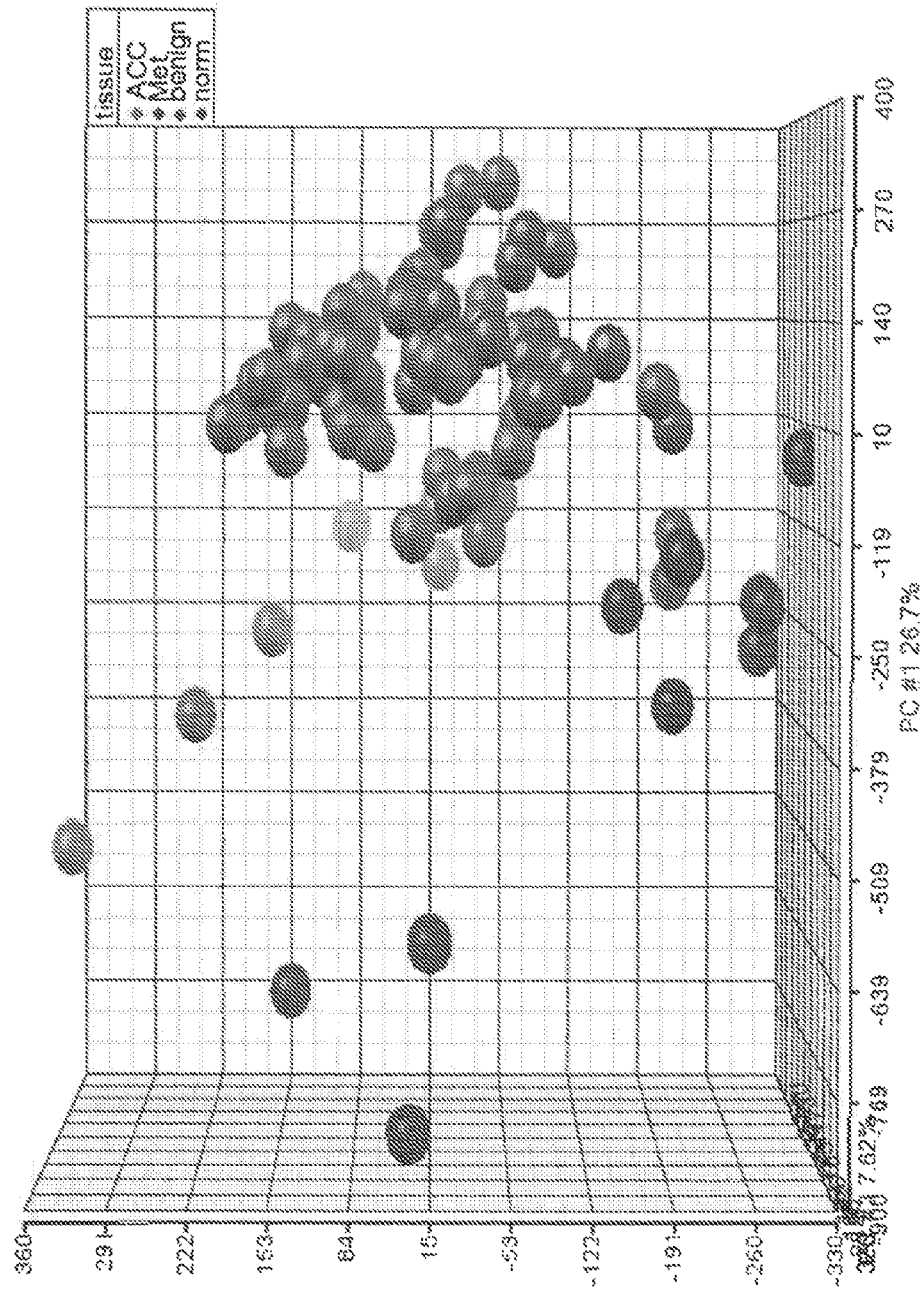
FIG. 2 is a principal component analysis of Normal, Benign, Primary Malignant and Metastatic Tissue Samples. Using ANOVA and an adjusted p-value of ≤0.01, 44.5% of differentially methylated genes can separate the 4 tissue categories. Normal and benign tissue samples cluster more closely and have less variation across the individual samples. Primary malignant and metastatic tissue samples cluster separately from the normal and benign samples and each other and have more variability across each sample.

Using principal component analysis to determine the global methylation patterns of 19 normal, 47 benign, 8 primary malignant and 12 metastatic tissue samples and ANOVA with an adjusted p-value of ≤0.01, normal and benign adrenocortical tissue samples clustered more closely with less variation. Primary malignant and metastatic tissue samples cluster separately from the normal and benign samples and each other and had greater variability between each sample (FIG. 2).

Analysis of the methylation pattern of benign adrenocortical tumor samples by functional status (cortisol secreting, aldosterone secreting, and nonfunctioning) showed different methylation patterns. Aldosterone secreting tumor samples as compared to nonfunctioning samples had 397 differentially methylated CpG sites (98 hypermethylated, 299 hypomethylated sites). Only eighteen differentially methylated CpG sites were found between cortisol secreting tumor samples as compared to aldosterone secreting tumor samples and all of these sites were hypermethylated. No significant differences in the methylation pattern between cortisol secreting tumors and nonfunctioning tumor samples.

In sum, a greater number of differential methylation was observed from normal-to-benign-to-primary ACC-to metastatic ACC. On the other hand, although benign samples had the lowest number of methylation CpG probe site differences compared to normal tissue samples, these differences showed the highest percentage of both total and hypermethylated and hypomethylated probe sites in other/open sea regions and the lowest in the island, shore or shelf regions in contrast to primary ACC and metastatic ACC samples where the highest percentage of both total and hypermethylated and hypomethylated probe sites in the island, shore or shelf regions and the lowest in the other/open sea regions.

Example 3

Methylation Distribution and Classification Analysis of Human Adrenocortical Tissue Samples This example describes methylation distribution and classification analysis of human adrenocortical tissue samples.

Figure 3A:
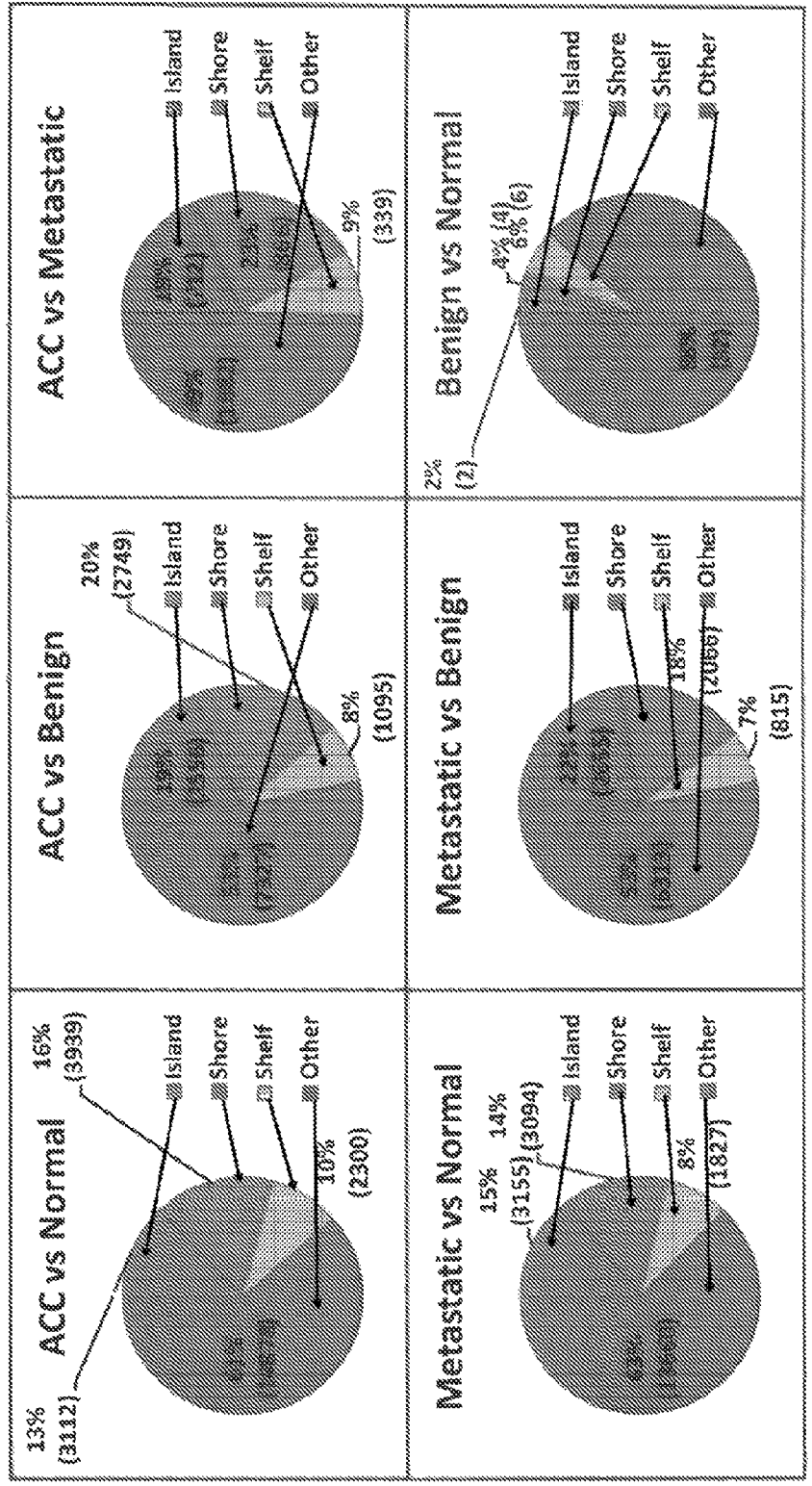
FIGS. 3A-3C include a series of pie charts illustrating the percentage differences of CpG methylation probe location and functional genomic differences between normal, benign, primary and metastatic malignant tissue samples. CpG locations in island, shore, shelf and other are shown in FIG. 3A. Methylation differences by functional genomics (promoter, body, 3'UTR and intergenic regions) are shown in FIG. 3B. Methylation differences by RNA coding and noncoding regions are shown in FIG. 3C. Normal and benign tissue samples had the least number of differentially methylated sites but these sites are predominantly in the other/open sea and promoter regions of the genome, as well as, RNA coding regions.

Methylated cytosines can be in CpG islands, shores, shelves, open sea, and sites surrounding transcription sites (−200 to −1500 bp, 5'UTRs and exons 1) for coding genes, as well as, gene bodies and 3'UTRs and other/open sea regions derived from GWAS studies. Shores are considered regions 0-2 kb from CpG islands, shelves are regions 2-4 kb from CpG islands and other/open sea regions are isolated CpG sites in the genome that do not have a specific designation. When comparing the different tissue groups, the benign samples compared to normal tissue samples had the lowest number of methylation CpG probe site differences, but these differences showed the highest percentage of probe sites in other/open sea regions (88%), and the lowest in the island (2%), shore (4%) or shelf (6%) regions. Primary ACC compared to normal, benign and metastatic tissue samples had a range of 49% to 61% CpG methylation differences in the other/open sea regions, 13-19% of probes in the island regions, 16-23% in the shores, and 8-10% in the shelves. Similarly, metastatic tissue samples compared to normal and benign samples had a 53-63% number of differentially methylated CpG sites in the intergenic regions, 15-22% within CpG islands, 14-18% in the shores, and 7-8% in the shelves (FIG. 3A).

Figure 4A:
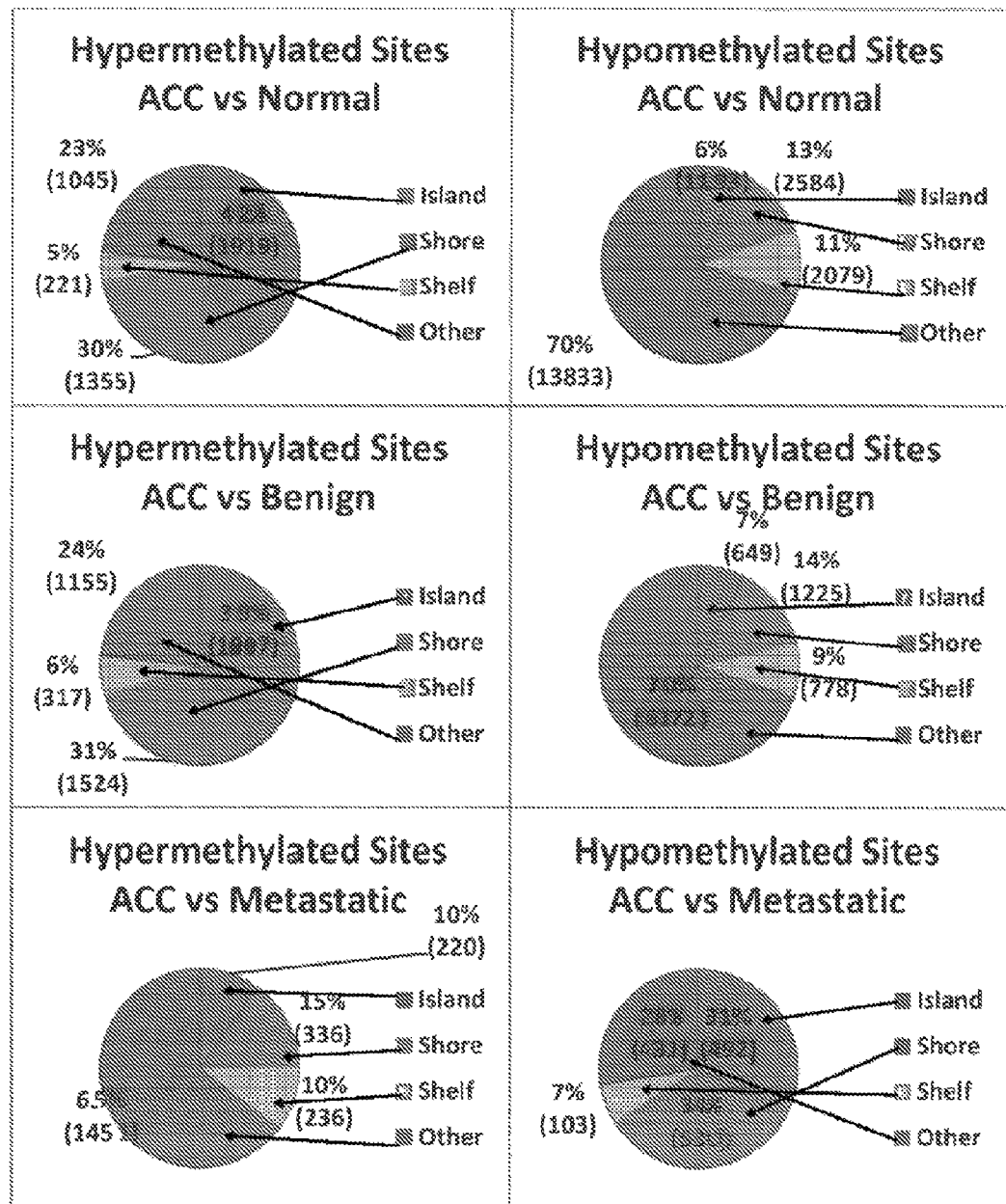
FIGS. 4A and 4B include a series of pie charts illustrating CpG locations in island, shore, shelf and other stratified by hypermethylation or hypomethylation.
Figure 4B:
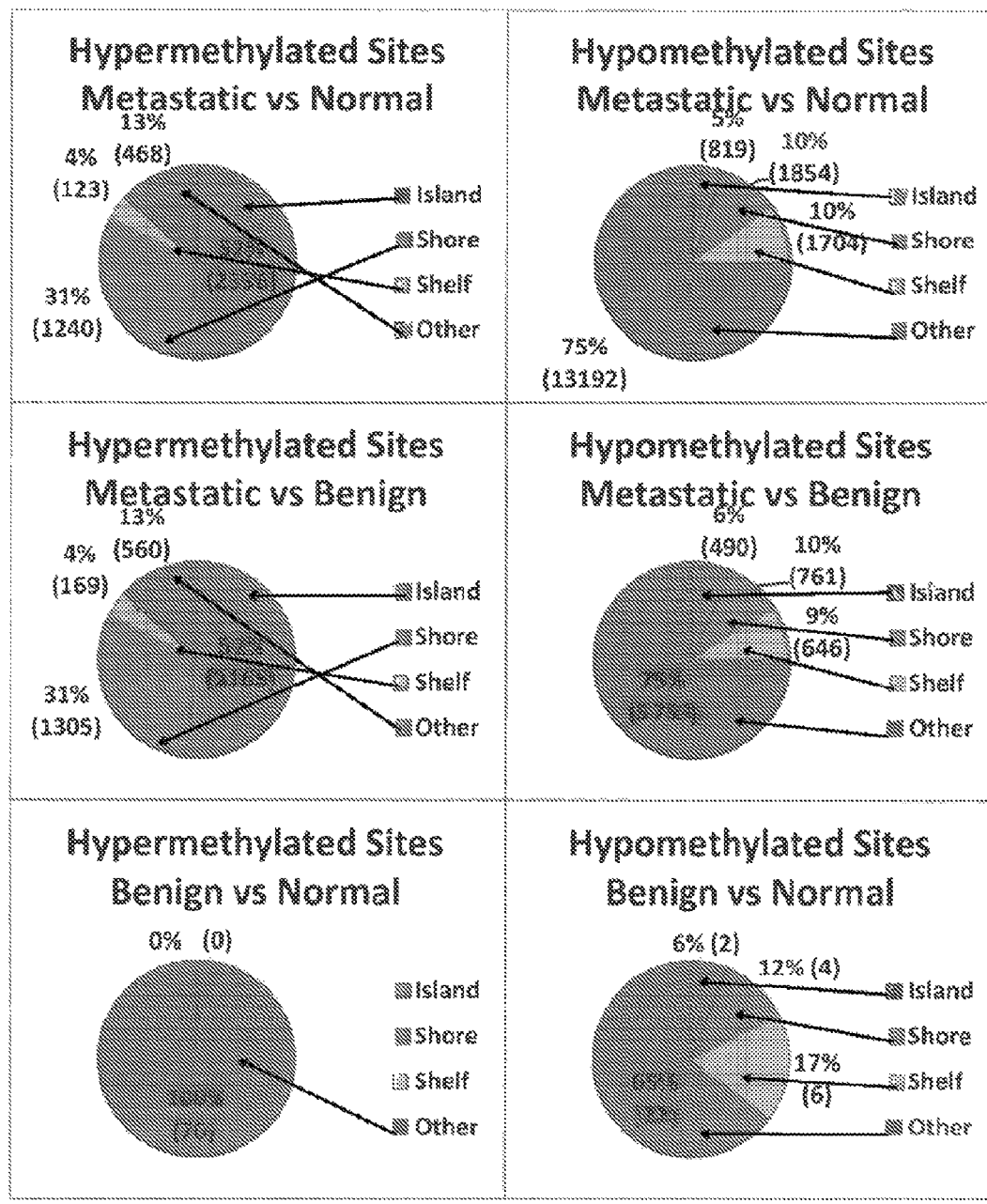
Figure 4D:
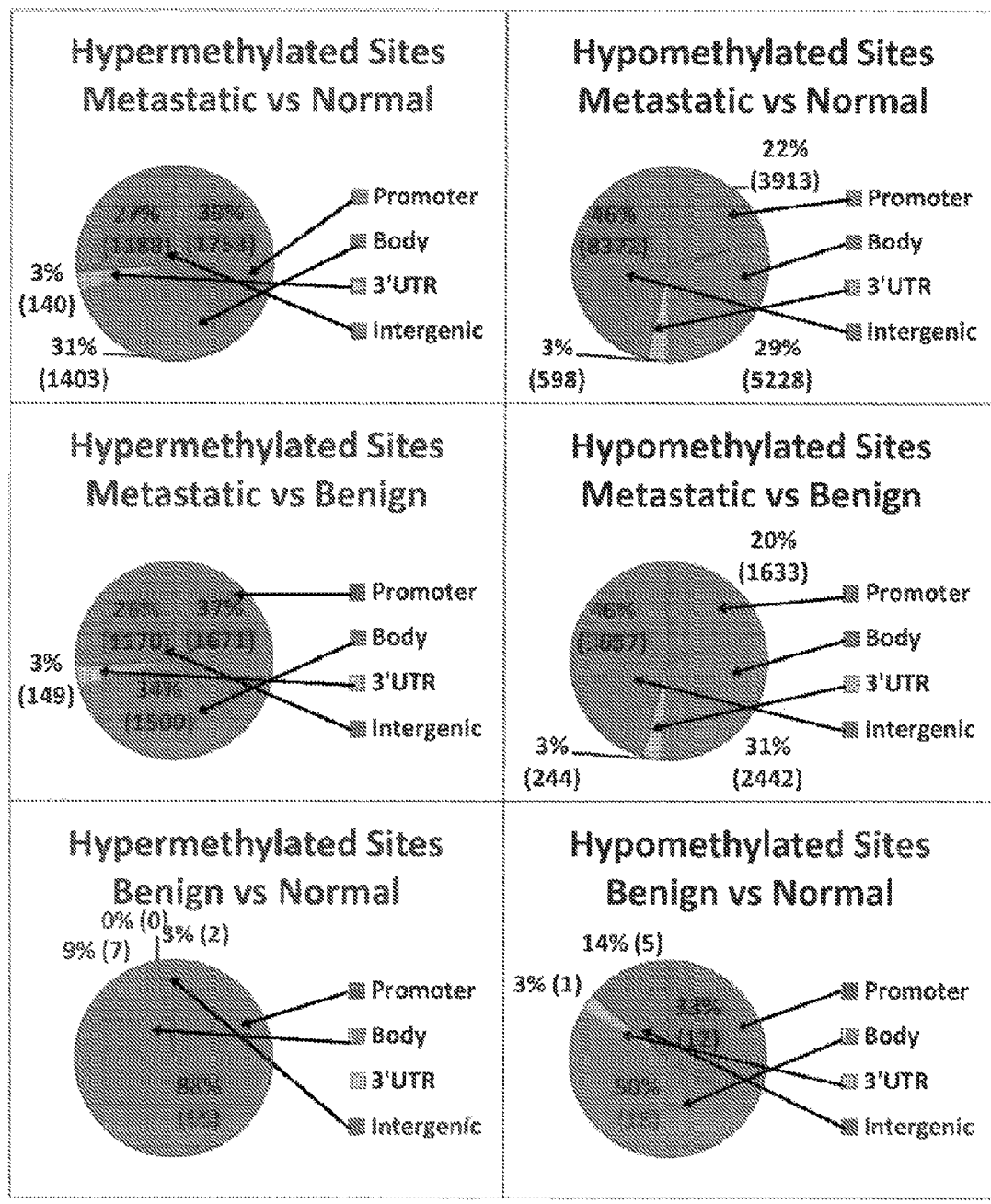
Figure 4E:
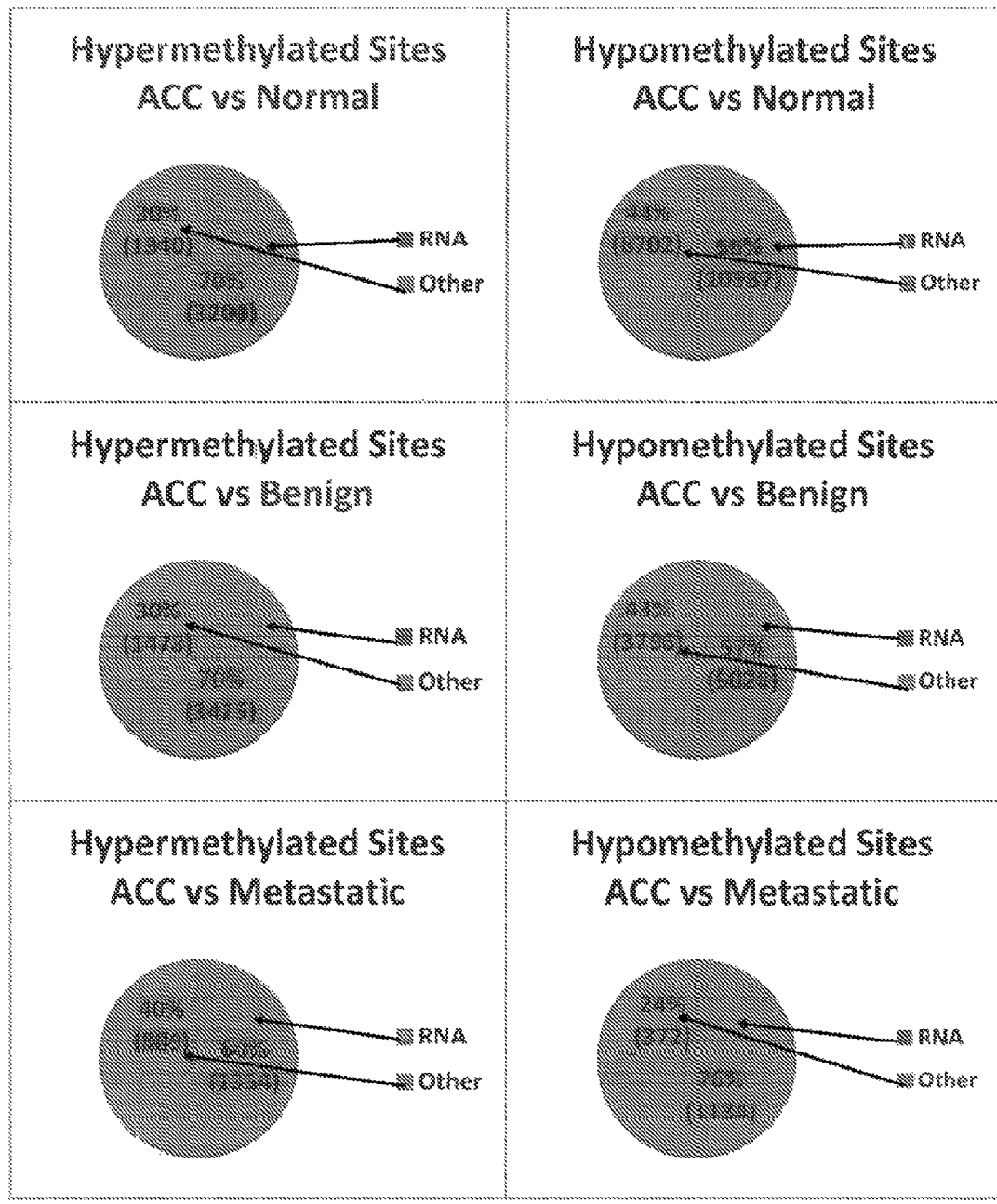
FIGS. 4E and 4F include a series of pie charts illustrating methylation differences by coding and noncoding regions stratified by hypermethylation or hypomethylation status. Benign tissue samples have the highest percentage of hypermethylated CpG sites located outside of islands, shores or shelves, in promoter regions, and in RNA coding regions of DNA.
Figure 4F:
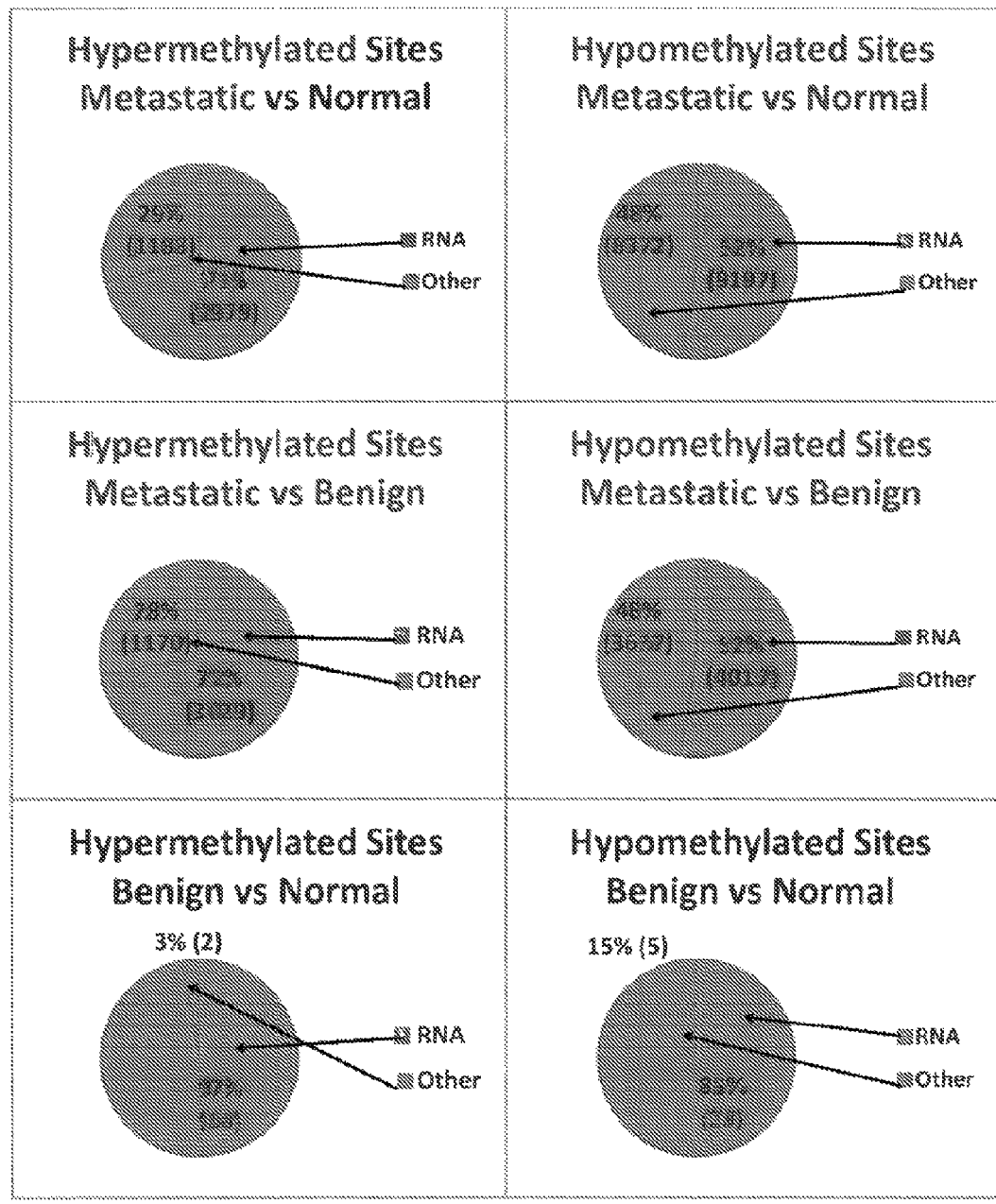

The CpG sites were then separated based on hypermethylated or hypomethylated status. While benign tissue samples compared to normal tissue have the lowest total number of methylation differences, 100% of hypermethylated sites and 65% of hypomethylated sites in other/open sea regions. Hypermethylated CpG sites in primary and metastatic ACC samples compared to both normal and benign tissue were predominantly in islands (42-39% for primary and 52% for metastatic ACC tissues) but the hypomethylated sites in these two comparisons were predominately in other/open sea regions (70% for primary 75% for metastatic ACC tissues). In addition, primary ACC compared to metastatic samples had hypermethylated sites predominantly in the other/open sea region (65%) but the hypomethylated sites were predominantly in shores (34%), islands (31%) and shelves (28%) (FIGS. 4A and 4B).

Figure 3B:
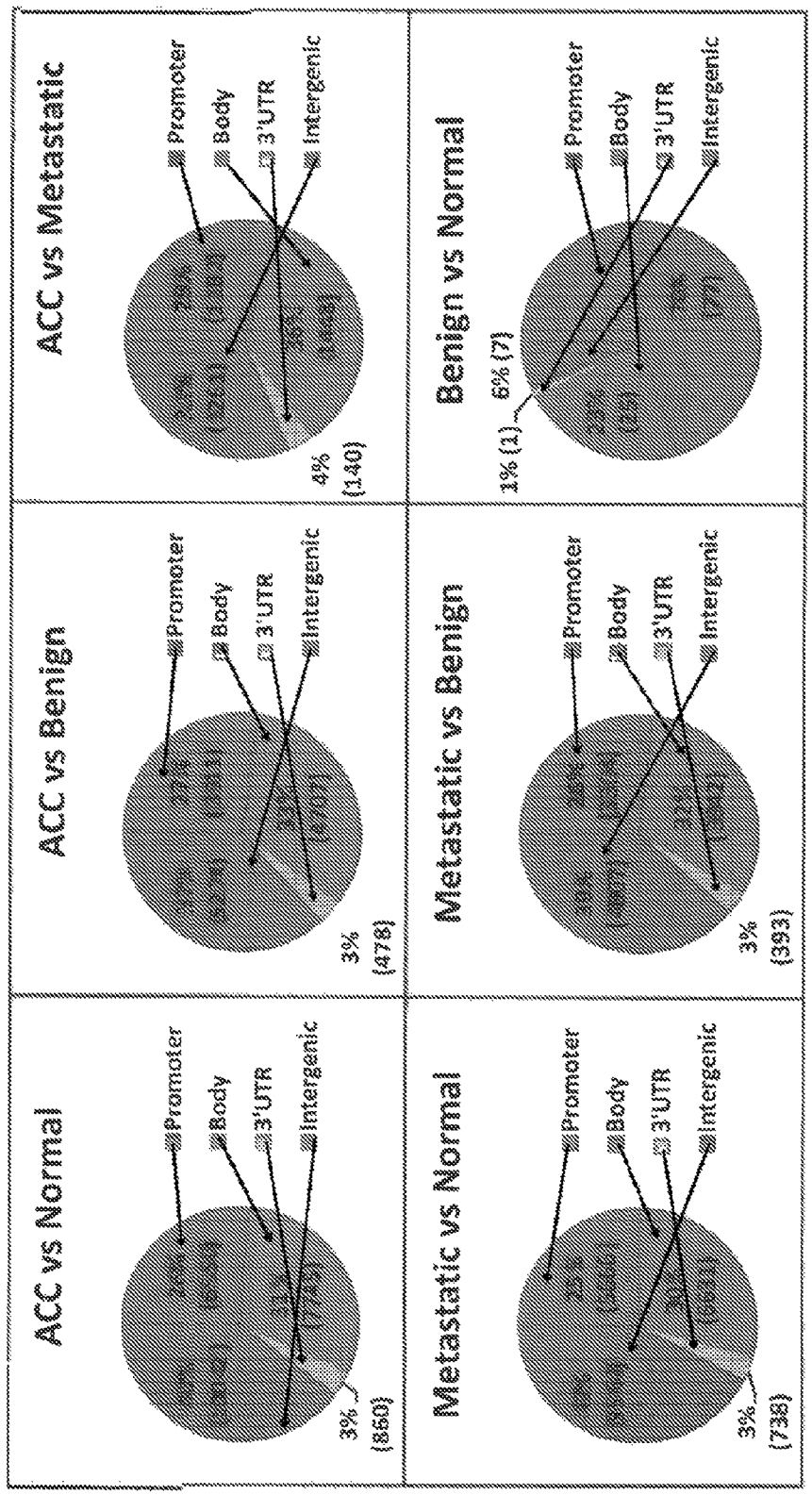

Functional genomic distribution also varied across the tissue comparisons. Although benign and normal tissue samples had the lowest number of methylation probe site differences, the difference in distribution of the CpG sites was the greatest. The differential methylation of probes that distinguished benign from normal tissue samples was highest in the promoter regions of genes (70%) and lowest in the body (23%), 3'UTR (1%) and intergenic regions (7%) compared to other tissue group comparisons. Primary ACC compared to normal, benign, and metastatic tissue samples had a range of 26-29% of differentially methylated probes in promoter regions, 31-36% in the body, 3-4% in 3'UTR regions, and 31-47% in intergenic regions. Metastatic compared to normal and benign tissue samples had 25-26% of differentially methylated probes in promoter regions, 30-32% in the body, 3% in 3'UTR region, and 39-42% in intergenic regions (FIG. 3B).

When the CpG sites were then separated based on hypermethylated or hypomethylated status, benign compared to normal samples had 88% of hypermethylated sites localized in promoter regions and 50% of hypomethylated sites in body regions. Primary and metastatic ACC samples compared to normal and benign tissues had most of the hypermethylated sites in promoter (36-35% primary and 39-37% metastatic respectively), body (33% primary, 31-34% metastatic respectively) and intergenic regions (28% primary, 27-26% metastatic respectively) however the hypomethylated sites were predominantly in intergenic regions (43-42% primary, 46% metastatic respectively). Primary compared to metastatic ACC samples however had hypermethylated sites that were 38% in intergenic regions and 41% of hypomethylated sites in gene bodies (FIG. 4B).

Figure 3C:
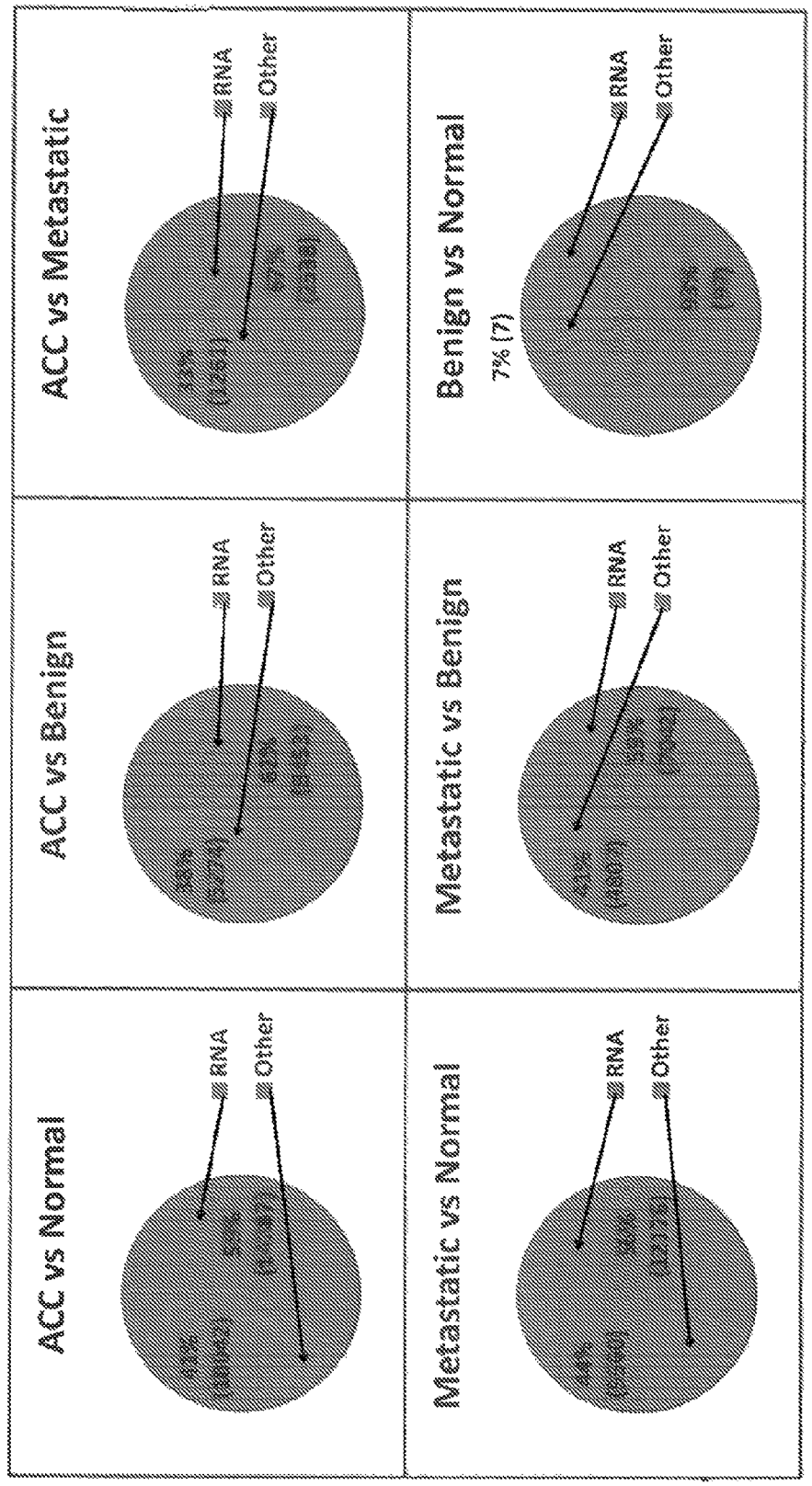

RNA coding content compared to other genome content of the differentially methylated probe sites in the comparisons again showed that although the total number of differentially methylated sites is lowest in benign compared to normal samples, these show the highest percentage distribution in the RNA category (93%), compared to other genomic content (7%). Primary ACC tissue samples compared to normal, benign, and metastatic tissue samples had 59-67% of the differentially methylated sites in RNA coding regions of the genome and 33-41% in other regions. Metastatic compared to normal and benign tissue samples had 56-59% (respectively) differentially methylated probes in RNA coding regions and 41-44% (respectively) in other regions of the genome (FIG. 3C).

Separating the methylation differences in the tissue comparisons based on hypermethylation or hypomethylation revealed that in all tissue comparisons, regardless of methylation status, the predominance of CpG methylation differences were in RNA coding regions. The greatest number of both hyper and hypomethylated sites in RNA coding regions were in the benign compared to normal tissue comparison (hypermethylated 97%, hypomethylated 85%). The next largest number of hypermethylated sites in RNA coding regions was in the primary and metastatic ACC compared to normal and benign tissue comparisons (70% primary, 71-72% metastatic respectively). The hypomethylated sites in primary and metastatic ACC compared to normal and benign tissue samples were (56-57% primary and 52% metastatic respectively). Primary ACC compared to metastatic tissues had hypermethylated sites (60%) and hypomethylated (76%) in RNA coding regions (FIG. 4C). This indicates that although the methylation differences may be small, they may be in more biologically relevant regions of the genome.

Example 4

Unsupervised Cluster Analysis of Primary Malignant and Benign Tissue Samples

This example describes unsupervised cluster analysis of primary malignant and benign tissue samples.

Because it is sometimes difficult to distinguish between primary malignant and benign adrenocortical neoplasms, an unsupervised hierarchical cluster analysis was performed between these two groups, using data from ANOVA analysis and cutoff values of p≤0.01 and $\Delta\beta \leq -0.20$ or $\Delta\beta \geq 0.20$. The primary ACC and benign tissue samples almost completely clustered separately based on their methylation differences with the exception of one ACC sample, that consistently clustered with benign tissue samples, and one benign tissue sample which had extensive necrosis. These studies indicate that methylation differences can be used to distinguish a primary malignant ACC from a benign adrenocortical tumor.

Example 5

Differential Methylated Regions of Chromosomes in Primary ACC and Benign Adrenocortical Tumors This example illustrates differential methylated regions of chromosomes in primary ACC and benign adrenocortical tumors.

Figure 5:
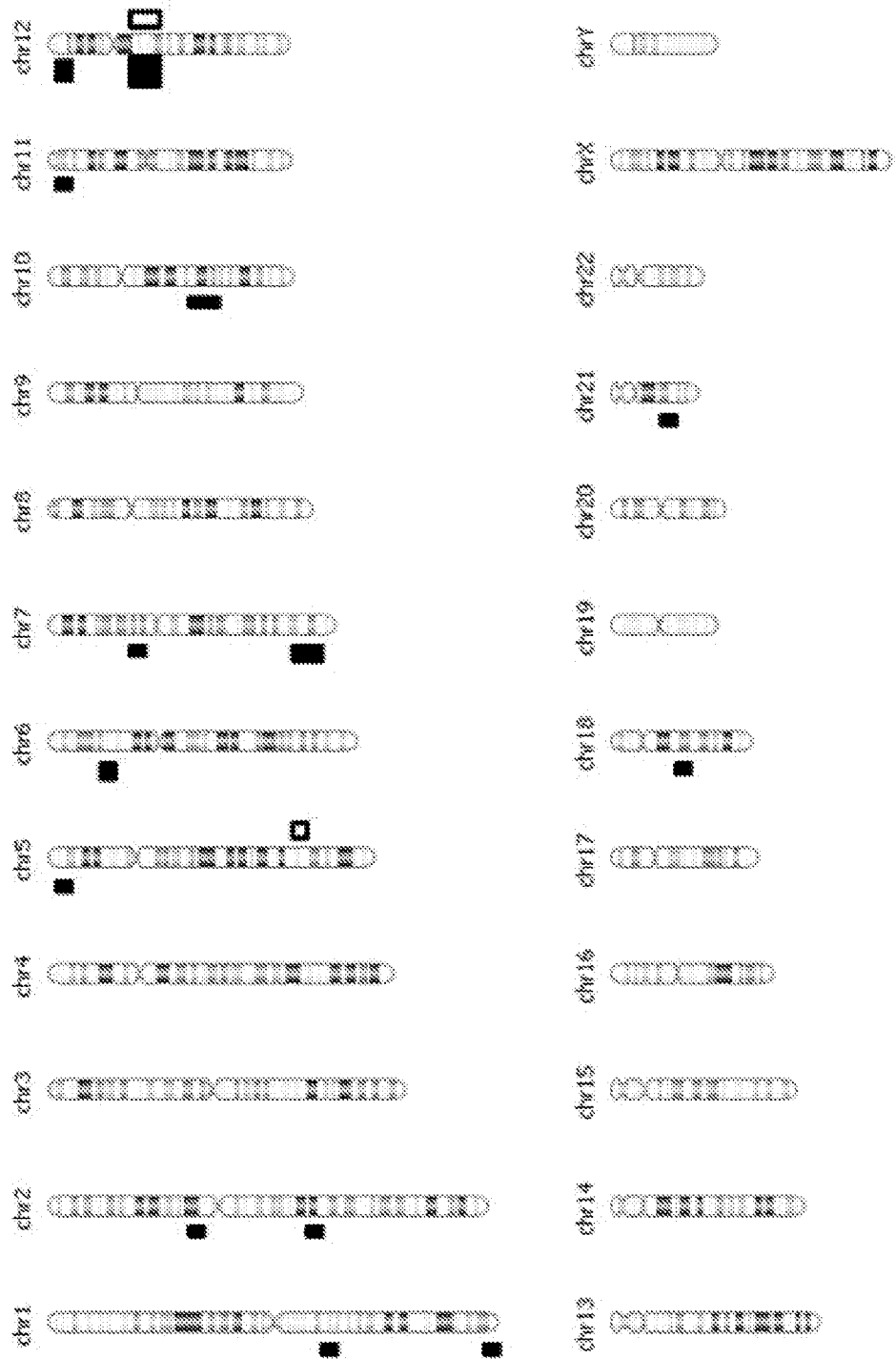
FIG. 5 is a schematic illustrating methylation cluster differences in chromosome regions in primary ACC compared to benign tissue samples using ANOVA an adjusted $p \leq 0.01$ and a $\Delta\beta \leq -0.20$ or $\Delta\beta \geq 0.20$ cutoff. Chromosomes 1, 2, 5, 6, 7, 10, 11, 12, 18, and 21 all had regions of methylation clusters. Hypermethylated regions were found in primary ACC samples in chromosomes 1q, 2p, 2q, 5p, 6p, 7p, 7q, 10q, 11p, 12p, 12q, 18q, and 21q (denoted by a filled box) whereas hypomethylated regions were found in chromosome 5q and 12q (denoted by an unfilled box).

Comparative genomic hybridization studies of adrenocortical tumors have shown frequent chromosomal gains and losses comparing ACC and benign tumors. Thus, the chromosomal regions which showed differentially methylation between benign and primary ACC tumor samples were analyzed using cutoff values of p≤0.01 and $\Delta\beta \leq -0.20$ or $\Delta\beta \geq 0.20$. Clusters of differentially methylated sites were located in select chromosomal regions; hypermethylated regions in primary ACC samples in chromosomes 1q, 2p, 2q, 5p, 6p, 7p, 7q, 10q, 11p, 12p, 12q, 18q, and 21q, and hypomethylated regions in chromosome 5q and 12q (FIG. 5). These studies also indicate that methylation differences can be used to distinguish a primary malignant ACC from a benign adrenocortical tumor.

Example 6

Genes Differentially Methylated Between Primary Malignant and Benign Adrenocortical Samples This example demonstrates differently methylated genes in primary malignant and benign adrenocortical samples.

Given the difficulty using histopathology in distinguishing benign and malignant samples, at the epigenetic level there were several differentially methylated probe sites that separated these two categories. With the exception of one ACC sample, that clustered with benign tissue samples, all ACC samples had robust differential hypermethylation of probe sites for KCTD12 (mean difference across three sites of 2.65, $\Delta\beta=0.35$), KIRREL (mean difference 2.14, $\Delta\beta=0.34$), SYNGR1 (mean difference, 1.65, $\Delta\beta=0.27$), and NTNG2 (mean difference 2.50, $\Delta\beta=0.38$). Furthermore, other genes implicated in the pathogenesis of ACC such as GATA6 had probe sites that were significantly hypermethylated (mean difference across three sites of 1.99, $\Delta\beta=0.32$). And TP53, and β-catenin (CTNNB1), each had one site that was hypomethylated (mean difference −1.44, $\Delta\beta=0.22$ and −1.49, $\Delta\beta=0.21$ respectively).

In addition, several hypermethylated CpG sites include those associated with imprinted genes of the chromosome 11p15 locus, including IGF2 and H19 (mean ACC-mean benign difference of 1.54, $\Delta\beta=0.24$ and 1.24, $\Delta\beta=0.20$ respectively). In addition, other genes associated with the IGF2 signaling pathway also had some probe sites that were hypermethylated such as CpG sites associated with IGF1R (mean difference across five probes 1.88, $\Delta\beta=0.28$) and AKT1 (mean difference across four probes, 1.80, $\Delta\beta=0.25$). RARRES2 and SLC16A9, two genes which are diagnostic markers for ACC and underexpressed in ACC, were also found to have probe sites that were differentially methylated. RARRES2 had hypermethylated CpG sites (mean difference across five probes, 1.75, $\Delta\beta=0.27$), and SLC16A9 had hypermethylated sites (mean difference across two sites, 1.70, $\Delta\beta=0.26$).

When comparing the methylome of primary malignant and benign adrenocortical tissue samples, a clear signature of differentially methylated probe sites emerged that could classify these two categories. Therefore, determination of the methylation difference in certain probe sites in adrenocortical tumors is a useful diagnostic for localized primary ACC, such as an adjunct to histopathology for localized primary ACC.

Example 7

Integrated Analysis of Genome-Wide MRNA Expression and Methylation Profile in Primary Malignant and Benign Adrenocortical Tissue Samples This example demonstrates an integrated analysis of genome-wide mRNA expression and methylation profile in primary malignant and benign adrenocortical tissue samples.

In addition to methylation profiling of primary ACC and benign samples, genome-wide mRNA gene expression profiling was performed in a subset of samples (5 ACC and 74 benign samples). Seven hundred seventy-three (773) probes were differentially expressed (2-fold expression change and adjusted p≤0.05). Of these, 215 were downregulated genes and 558 were upregulated. Of the downregulated genes, 52 were also hypermethylated (ANOVA adjusted p≤0.01 and $\Delta\beta \leq -0.20$ or $\Delta\beta \geq 0.20$). Two of these genes, RARRES2 and SLC16A9, were not only both significantly hypermethylated, but also downregulated in primary ACC samples (−11.98, adj p<0.001; and −12.32, p<0.001 respectively). GATA6 also had several hypermethylated sites and was downregulated in gene expression (−3.64, adj p<0.001).

When the 52 hypermethylated and downregulated genes were analyzed using Ingenuity pathway analysis software, these genes were present in five biological function networks (Table 2). The network that had the greatest number of genes was the drug metabolism, endocrine system development and function, lipid metabolism biological function pathway and it contained 16 genes that were both hypermethylated and downregulated including RARRES2 and GATA6. The next largest biological function pathway was the lipid metabolism, small molecule biochemistry, cell cycle network which had 12 hypermethylated and downregulated genes. Table 3 provides sequences, Gene IDs, probes, primers and array addresses for some of the identified adrenocortical tumor-related molecules (all of the referenced IDs, accession numbers and addresses are incorporated by reference in their entirety as of Mar. 26, 2012).

Figure 6:
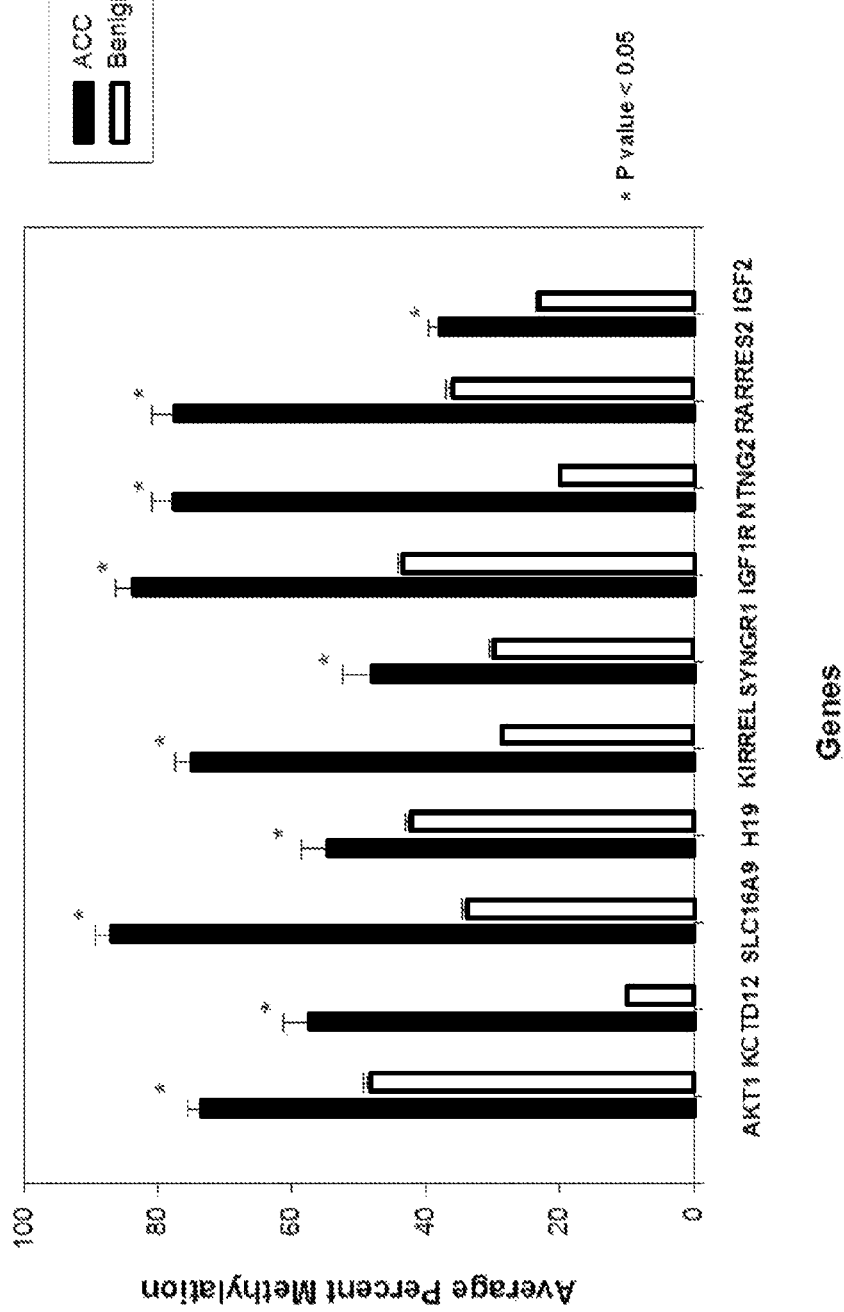
FIG. 6 is a bar graph illustrating pyrosequencing methylation validation for 10 of the disclosed malignant adrenocortical tumor-related genes.

Ten genes were selected for validation for distinguishing between benign and malignant tumors by a more quantitative method of assessing CpG methylation. By pyrosequencing, the inventors were able to validate all 10 genes to be differentially methylated (See FIG. 6).

TABLE 2

| Biological Function Pathway Analysis Networks of Hypermethylated and Downregulated Genes | | |
|---|---|---|
| Biological Function Pathway | Score (Number of Other Genes/Hypermethylated and Downregulated Genes from datasets) | Hypermethylated and Downregulated Genes (adj p < 0.01, β = 0.2; ≥ 2-fold, adj p < 0.05) |
| Drug Metabolism, Endocrine System Development and Function, Lipid Metabolism | 38/16 | ABCA1, CD55, CD74, COL4A3, GOS2, GATA6, HSD3B2, KCNQ1, MAP3K5, NCOA7, RAPGEF4, RARRES2, S100A6, SPTBN1, TNFSF13, TNS1 |
| Lipid Metabolism, Small Molecule Biochemistry, Cell Cycle | 27/12 | ADCK3, ALDH3B1, CSDC2, CYP7B1, GIPC2, HOOK1, MEIS1, MLH3, MRPL33, NME5, RGNEF, TCIRG1 |
| Lipid Metabolism, Small Molecule Biochemistry, Energy Production | 21/10 | AMPD3, B4GALT6, CAB39L, CD55, GYPC, NDRG4, RAB34, RBPMS, SEMA6A, TNFS1F2-TNFSF13 |
| Cell-To-Cell Signaling and Interaction, Cellular Assembly and Organization, Nervous System Development and Function | 3/1 | SLC16A9 |
| Hematological Disease, Immunological Disease, Infectious Disease | 2/1 | PHF11 |

TABLE 3

| UCSC_RefGene_Name | IlmnID | Name | AddressA_ID |
|---|---|---|---|
| IL13RA2 | cg18139692 | cg18139692 | 44807356 |
| CTNNB1; CTNNB1; CTNNB1 | cg05726118 | cg05726118 | 51617321 |
| RARRES2 | cg11327659 | cg11327659 | 48680443 |
| RARRES2 | cg13722127 | cg13722127 | 59610502 |
| RARRES2 | cg19310340 | cg19310340 | 51721372 |
| RARRES2 | cg21521758 | cg21521758 | 12708419 |
| EGFR; EGFR; EGFR; EGFR | cg26277197 | cg26277197 | 38760405 |
| RARRES2 | cg27455017 | cg27455017 | 46752321 |
| SLC16A9 | cg22544571 | cg22544571 | 34541394 |
| SLC16A9 | cg24603972 | cg24603972 | 67796320 |
| IGF2; INS-IGF2; INS-IGF2 | cg27263998 | cg27263998 | 19633313 |
| AKT1; AKT1; AKT1 | cg15912732 | cg15912732 | 73780366 |
| AKT1; AKT1; AKT1 | cg19831386 | cg19831386 | 47602487 |
| AKT1; AKT1; AKT1 | cg22991936 | cg22991936 | 41717479 |
| AKT1; AKT1; AKTI | cg26099837 | cg26099837 | 60563354 |
| IGF1R | cg02350767 | cg02350767 | 14730364 |
| IGF1R | cg21245492 | cg21245492 | 12563443 |
| IGF1R | cg26329756 | cg26329756 | 16532508 |

TABLE 3-continued

| | | | |
|---|---|---|---|
| IGF1R | cg27139419 | cg27139419 | 14791309 |
| IGF1R | cg27534520 | cg27534520 | 61522400 |
| TP53; WRAP53; TP53; TP53; TP53 | cg07760161 | cg07760161 | 60775326 |
| GATA6 | cg14880184 | cg14880184 | 14784355 |
| GATA6 | cg15424989 | cg15424989 | 26667348 |
| GATA6 | cg26987699 | cg26987699 | 22785438 |

| UCSC_RefGene_Name | AlleleA_ProbeSeq |
|---|---|
| IL13RA2 | TCTTACTAATTCACAATAAAATTATAATATCATCCATCTCCATAACAACC<br>SEQ. ID. NO. 1 |
| CTNNB1; CTNNB1; CTNNB1 | ATTACACCCACAAAAAAAACCCATATCCTCTTTTACCAAATTAATAAAAC<br>SEQ. ID. NO. 2 |
| RARRES2 | CATAAATTAAAAAATCCATTAAAAAACCCTAAAATTAAAAACCCCACTAC<br>SEQ. ID. NO. 3 |
| RARRES2 | AAATAAAAAAACCTAAAAATAACCCTTTCTCCAAATTAACCTTAAAATCC<br>SEQ. ID. NO. 4 |
| RARRES2 | ACTACAACTTAAATTCCAACCTCACAAATATTCCAACTAAAAAAACTAC<br>SEQ. ID. NO. 5 |
| RARRES2 | TAACTATACCTAAAACCTACTAACCTACATAACCTCTTACTCCTAAACTC<br>SEQ. ID. NO. 6 |
| EGFR; EGFR; EGFR; EGFR | ACCAACCCAACAAAATCCCAACTTACAACAAACAAACAATTCACTCTACC<br>SEQ. ID. NO. 7 |
| RARRES2 | ACCTACAATTTTAACAAAATTCCCTACCCACRCTAAAAATCAATCAATTC<br>SEQ. ID. NO. 8 |
| SLC16A9 | TAAATCRATATACCCTAACAATTTCTTATATTTAAATTAACTTCAACTTC<br>SEQ. ID. NO. 9 |
| SLC16A9 | AAAATATTTCCCTCTATTTATCATACAAATATATCAATCTCCTCTTCTAC<br>SEQ. ID. NO. 10 |
| IGF2; INS-IGF2; INS-IGF2 | ACTTAAAATAACACTTAACAATTACTTAACACCCTAAAATATTAATAAAC<br>SEQ. ID. NO. 11 |
| AKT1; AKT1; AKT1 | TATATAAACAACATATCCAAACCACAAATCTAAATACCTAACCAAACCCA<br>SEQ. ID. NO. 12 |
| AKT1; AKT1; AKT1 | CCCCACAAAAAATCAAAAAAAACCTAAAACAACAACAAAAAAATTAAACA<br>SEQ. ID. NO. 13 |
| AKT1; AKT1; AKT1 | AAATAAATACCAACCACAAAAACACCACCTAAACTCCCTCAAACTAATCA<br>SEQ. ID. NO. 14 |
| AKT1; AKT1; AKT1 | ACAAACCAAAACCAAATAAACAAAAATCAAAAAAAACTACCTAAAACACA<br>SEQ. ID. NO. 15 |
| IGF1R | CTTTCRCCTCTACCTCTATATACCTCTAAACTATAAACTTTAATTTACAC<br>SEQ. ID. NO. 16 |
| IGF1R | CATTCAAACCTTAACAACTAACACTCTACAAAACAAACCAAAAATATACA<br>SEQ. ID. NO. 17 |
| IGFIR | TAACCRTACAAACTAAAACTTACAACCCAAAAACACACAAAAACAAAAAC<br>SEQ. ID. NO. 18 |
| IGF1R | TATAAACAATTTAAAAACAAATAAAACAAACTTATAATTTCCACTAACTC<br>SEQ. ID. NO. 19 |
| IGF1R | AAAAAAAAACAATTAAAACAAACAATCRCTCAAATACCAACACCAAATTC<br>SEQ. ID. NO. 20 |
| TP53; WRAP53; TP53; TP53; TP53 | ACAACCACAAAAATATACCACATTAAAAAAACTAACAATACCTAATATCC<br>SEQ. ID. NO. 21 |
| GATA6 | CRAAATTAATCCCTAAAATCAAAATTCCCTTACTTTAAAACATAATAACC<br>SEQ. ID. NO. 22 |

TABLE 3-continued

| | |
|---|---|
| GATA6 | TCCTCRAATTACCATCACCAATTTCTTACCTATCTTACCAAAATTATTAC SEQ. ID. NO. 23 |
| GATA6 | AAATAAAAATATAATTTATATATTCTTAAATTAAACATTTTCCCCAATTC SEQ. ID. NO. 24 |

| UCSC_RefGene_Name | AddressB_ID |
|---|---|
| IL13RA2 | |
| CTNNB1; CTNNB1; CTNNB1 | |
| RARRES2 | |
| RARRES2 | |
| RARRES2 | |
| RARRES2 | |
| EGFR; EGFR; EGFR; EGFR | |
| RARRES2 | |
| SLC16A9 | |
| SLC16A9 | |
| IGF2; INS-IGF2; INS-IGF2 | |
| AKT1; AKT1; AKT1 | 65617308 |
| AKT1; AKT1; AKT1 | 13757359 |
| AKT1; AKT1; AKT1 | 63678355 |
| AKT1; AKT1; AKT1 | 60697379 |
| IGF1R | |
| IGF1R | 66647369 |
| IGF1R | |
| IGF1R | |
| IGF1R | |
| TP53; WRAP53; TP53; TP53; TP53 | |
| GATA6 | |
| GATA6 | |
| GATA6 | |

| UCSG_RefGene_Name | AlleleB_ProbeSeq |
|---|---|
| IL13RA2 | |
| CTNNB1; CTNNB1; CTNNB1 | |
| RARRES2 | |
| RARRES2 | |
| RARRES2 | |
| RARRES2 | |
| EGFR; EGFR; EGFR; EGFR | |
| RARRES2 | |
| SLC16A9 | |

TABLE 3-continued

| | |
|---|---|
| SLC16A9 | |
| IGF2; INS-IGF2; INS-IGF2 | |
| AKT1; AKT1; AKT1 | TATATAAACAACGTATCCAAACCACGAATCTAAATACCTAACCGAACCCG SEQ. ID. NO. 25 |
| AKT1; AKT1; AKT1 | CCCCACAAAAAATCAAAAAAAACCTAAAACGACAACGAAAAAATTAAACG SEQ. ID. NO. 26 |
| AKT1; AKT1; AKT1 | AAATAAATACCGACCGCAAAAACACCACCTAAACTCCCTCAAACTAATCG SEQ. ID. NO. 27 |
| AKT1; AKT1; AKT1 | ACAAACCAAAACCGAATAAACGAAAATCGAAAAAAACTACCTAAAACGCG SEQ. ID. NO. 28 |
| IGF1R | |
| IGF1R | CGTTCAAACCTTAACAACTAACGCTCTACAAAACGAACCAAAAATATACG SEQ. ID. NO. 29 |
| IGF1R | |
| IGF1R | |
| IGF1R | |
| TP53; WRAP53; TP53; TP53 | |
| GATA6 | |
| GATA6 | |
| GATA6 | |

| UCSC_RefGene_Name | Infinium_Design_Type | Next_Base | Color_Channel |
|---|---|---|---|
| IL13RA2 | II | | |
| CTNNB1; CTNNB1; CTNNB1 | II | | |
| RARRES2 | II | | |
| RARRES2 | II | | |
| RARRES2 | II | | |
| RARRES2 | II | | |
| EGFR; EGFR; EGFR; EGFR | II | | |
| RARRES2 | II | | |
| SLC16A9 | II | | |
| SLC16A9 | II | | |
| IGF2; INS-IGF2; INS-IGF2 | II | | |
| AKT1; AKT1; AKT1 | I | A | Red |
| AKT1; AKT1; AKT1 | I | T | Red |
| AKT1; AKT1; AKT1 | I | C | Grn |
| AKT1; AKT1; AKT1 | I | T | Red |
| IGF1R | II | | |
| IGF1R | I | A | Red |
| IGF1R | II | | |
| IGF1R | II | | |
| IGF1R | II | | |
| TP53; WRAP53; TP53; TP53 | II | | |

TABLE 3-continued

| UCSC_RefGene_Name | |
|---|---|
| GATA6 | II |
| GATA6 | II |
| GATA6 | II |

| UCSC_RefGene_Name | Forward_Sequence |
|---|---|
| ILI3RA2 | CACGAGAGTGTTCTTACTGGTTCACAATGGAGTTATGATATCATCCATCTCCATAGCAAC[CG]TCTCCCCAGCAACACATAAAACACAGTCAAATACTCTTTTCTGAGGGAAAAAAAGAAA SEQ. ID. NO. 30 |
| CTNNB1; CTNNB1; CTNNB1 | ACTGAAGTTCAGCAGTGATGGAGCTGTGGTTGAGGTGTCTGGAGGAGACCATGAGGTCTG[CG]TTTCACTAACCTGGTAAAAGAGGATATGGGTTTTTTTTGTGGGTGTAATAGTGACATTTA SEQ. ID. NO. 31 |
| RARRES2 | ACCAGCCACTCTCACAACCTTGGGTCAGGCTGAGCCACTCCACCTCTAAGGAGGCTCTT[CG]CAGTGGGGTCTCTAACCTCAGGGCTTCTTAATGGACCTCCCAATTCATGCATGCACACCC SEQ. ID. NO. 32 |
| RARRES2 | ACGCTGGGCACAGGTGAAGGAGCCTGGAAATGGCCCTTTCTCCAAATTGACCTTAGGGTC[CG]CCTGGCCCTCTCCGTCCCTCCCACCCTGCCCGCGCTGTTCCCTGGGGCCTGCAGTTTTA SEQ. ID. NO. 33 |
| RARRES2 | GCAGCTTGTCTGCTGCAGCTTAAATTCCAGCCTCACAAATATCCAGCTGGGAAGGGCTG[CG]GACAGACAGGCAGGCAGAGGATGGCCGTAGCCAGCTGGAGGGTGCAGAGCAAGCCCTGGT SEQ. ID. NO. 34 |
| RARRES2 | GCATCATGAGGGTGGGAGCCAGGGCTGCCCATCATGGGACCAGATCCCCAACTAGGCCCT[CG]AGCCCAGGAGCAAGAGGTCATGCAGGCCAGCAGGTTCAGGCACAGCCACCCTAGAATGT SEQ. ID. NO. 35 |
| EGFR; EGFR; EGFR; EGFR | AAGGCATTACGGTTAGAAACTGGCCAGGTGTCATTTTTGAGAGATTAGATAACTGTTTTC[CG]GTAGAGTGAATTGCCTGTTTGTTGCAAGTTGGGACTTTGCTGGGCTGGTTTACAGGGCCA SEQ. ID. NO. 36 |
| RARRES2 | TGTTCCCTGGGGCCTGCAGTTTTAGCAAAGTTCCCTGCCCACGCTAGGAATCAGTCAGTT[CG]CACTCCCACCCTACACCCCTAATCTTGCCCATTGTGTCTCTCCCTGGGTCTCCGGCACGA SEQ. ID. NO. 37 |
| SLC16A9 | CTCTTCGGAATCTTCTCTAGCTTCCTCAGCCCTCTGCCTAAACCTGCCTGAAGAATTTCT[CG]AAGCTGAAGCCAACTCAAATATAAGAAACTGTTAGGGCATACCGATTTACAGAATTTGAT SEQ. ID. NO. 38 |
| SLC16A9 | ACATTCCTTCCTGGCCATAAATTGGACCCTCCCATTTTCAGGCCCTCTTGTGTGAGTCAG[CG]CAGAAGAGGAGACTGATACATTTGCATGACAAATAGAGGGAAATATTCTGTGCCAGTATT SEQ. ID. NO. 39 |
| IGF2; INS-IGF2; INS-IGF2 | GGTGTAGCTTTACTTAGAGTGACACTTGGCAGTTACTTGACACCCTGGAATGTTGGTGGA[CG]TGGCACTGGTAAAATGGCGGGGGGGGGGGAATAAGGGGGACAAAGCAGGGTTCAAGAAT SEQ. ID. NO. 40 |
| AKT1; AKT1; AKT1 | CTCAGATGTCCGGAGACTGGACCCTCCGTGAGCCGCATGGACACACGGTCCCGTGTCACC[CG]GGCCCGGCCAGGCACCCAGATCCGTGGCTTGGACACGCTGCCCACACACTCAGGAGCGTC SEQ. ID. NO. 41 |
| AKT1; AKT1; AKT1 | AGGGATGGCCACCCCCACAGGGAGTCAGGGAGGGCCTGGGGCGACAGCGGAAAGGTTAAG[CG]TCGAAAAGGTCAAGTGCTACCGTGGAGAGATCATCTGAGGGGGAGGCTCCCGGTGGGACA SEQ. ID. NO. 42 |
| AKT1; AKT1; AKT1 | GGGTCACAGCCTGCCGAAGGCAGCCAGGCCTGCAGCTCTTCCCCGGCCCCTCTCGGACAG[CG]ACCAGCCTGAGGGAGTCCAGGTGGTGCCCCTGCGGCCGGCACCCACTCCTGGCCTAGGCC SEQ. ID. NO. 43 |
| AKT1; AKT1; AKT1 | CCCAGATCCGTGGCTTGGACACGCTGCCACACACTCAGGAGCGTCTGCCGCGTAACCCA[CG]CGCCCCAGGCAGCTTCCCTCGACCCCCGCCACTCGGCCTTGGCCTGCTGGGTCACAGCC SEQ. ID. NO. 44 |
| IGF1R | TGCAGATTTAACTTTCGCCTCTGCCTCTGTGTGCCTCTGGGCTGTAAGCTTTAGTTTGCA[CG]GTTAACGGGGATGGCCTCTCCCATGGTCGGTTGGAGTGTGTTGCACAGCGTCTGGTCCAG SEQ. ID. NO. 45 |
| IGF1R | CTGCTGAGCTGTCGTTCAGGCCTTGGCAACTGACGCTCTGCAGAACGGACCAGGAGTGTG[CG]GTGGTGGAGTCCGGCTGGCCTGGGTTGCAGATTTAACTTTCGCCTCTGCCTCTGTGTGCC SEQ. ID. NO. 46 |
| IGF1R | GAACGGACCAGGAGTGTGCGGTGGTGGAGTCCGGCTGGCCTGGGTTGCAGATTTAACTTT[CG]CCTCTGCCTCTGTGTGCCTCTGGGCTGTAAGCTTTAGTTTGCACGGTTAACGGGGATGGC SEQ. ID. NO. 47 |

TABLE 3-continued

| | |
|---|---|
| IGF1R | CCTGTTCATCCTGTGAGCAGTTTAGAGACAGATGACACAGGCTTATGGTTTCCACTGGCT[CG]GCTCCGTGCGTGTGCGGATTGGGCTTCCTGAGAGCCTGGTTAGCCCCTTTTATCTGCTCT SEQ. ID. NO. 48 |
| IGF1R | GCCCTCCCTCCACCTATTTGGATTAGACCAGGAGACTGCAGCAAACTTCTCAAGGGGAGG[CG]AACTTGGTGTTGGTATCTGAGCGATTGTCGTTTCAATTGTTTCCCTCTGTCTTGGAAAA SEQ. ID. NO. 49 |
| TP53; WRAP53; TP53; TP53; TP53 | AACTGTAAATTACAACCACAAGGATATACCACATTAGAAAGACTGACAATACCTAATGTC[CG]GAAGGCTGTGGCACAACCATAATAACTCCCATACCTTGCTAGTTGGAGTGTAAAATGGTA SEQ. ID. NO. 50 |
| GATA6 | GTGATCCCGCCCGCCTCGGCCTCCCGAAGTGCTAGGATTACAGGCGTGAGCCACCGCGC[CG]GCCACCATGTTTTAAAGTAAGGGAATCCTGATTTCAGGGATTAATCTCGTATTGTCATTG SEQ. ID. NO. 51 |
| GATA6 | TGTTTTAAGCAAAAAAGAAAAAATAATCTATATATCTCTAGGTGTACTTGCCAAAAGCAC[CG]TAATAATTCTGGTAAGATAGGCAAGAAATTGGTGATGGTAACCCGAGGAGAAAAACAGTA SEQ. ID. NO. 52 |
| GATA6 | TTGTAGAACTTGAGTAAAAGTGTGGTTTGTATGTTCTTAAGTTGAGCATTTTCCCCAATT[CG]CACACGTTTTACTGTTTTTTTGTTTTTTTTTTTTTTTTTTTTTRRGAGACGGAGTTT SEQ. ID. NO. 53 |

| UCSC_RefGene_Name | Genome_Build | CHR | MAPINFO |
|---|---|---|---|
| ILI3RA2 | 37 | X | 114252251 |
| CTNNB1; CTNNB1; CTNNB1 | 37 | 3 | 41265374 |
| RARRES2 | 37 | 7 | 150037044 |
| RARRES2 | 37 | 7 | 150037890 |
| RARRES2 | 37 | 7 | 150037297 |
| RARRES2 | 37 | 7 | 150036287 |
| EGFR; EGFR; EGFR; EGFR | 37 | 7 | 55188632 |
| RARRES2 | 37 | 7 | 150037988 |
| SLC16A9 | 37 | 10 | 61468158 |
| SLC1649 | 37 | 10 | 61434211 |
| IGF2; INS-IGF2; INS-IGF2 | 37 | 11 | 2171007 |
| AKT1; AKT1; AKT1 | 37 | 14 | 105255285 |
| AKT1; AKT1; AKT1 | 37 | 14 | 105235891 |
| AKT1; AKT1; AKT1 | 37 | 14 | 105255472 |
| AKT1; AKT1; AKT1 | 37 | 14 | 105255361 |
| IGF1R | 37 | 15 | 99250527 |
| IGF1R | 37 | 15 | 99250440 |
| IGF1R | 17 | 15 | 99250482 |
| IGF1R | 37 | 15 | 99212404 |
| IGF1R | 37 | 15 | 99343918 |
| TP53; WRAP53; TP53; TP53; TP53 | 37 | 17 | 7588378 |
| GATA6 | 37 | 18 | 19758221 |
| GATA6 | 37 | 18 | 19757468 |
| GATA6 | 37 | 18 | 19757890 |

TABLE 3-continued

| UCSC_RefGene_Name | SourceSeq | Chromosome_36 |
|---|---|---|
| IL13RA2 | CGGTTGCTATGGAGATGGATGATATCATAACTCCATTGTGAACCAGTAAG SEQ. ID. NO. 54 | X |
| CTNNB1; CTNNB1; CTNNB1 | TTACACCCACAAAAAAAACCCATATCCTCTTTTACCAGGTTAGTCAAACG SEQ. ID. NO. 55 | 3 |
| RARRES2 | CGCAGTGGGGTCTCTAACCTCAGGGCTTCTTAATGGACCTCCCAATTCAT SEQ. ID. NO. 56 | 7 |
| RARRES2 | GGTGAAGGAGCCTGGAAATGGCCCTTTCTCCAAATTGACCTTAGGGTCCG SEQ. ID. NO. 57 | 7 |
| RARRES2 | CGCAGCCCTTCCCAGCTGGAATATTTGTGAGGCTGGAATTTAAGCTGCAG SEQ. ID. NO. 58 | 7 |
| RARRES2 | GGCTGTGCCTGAAACCTGCTGGCCTGCATGACCTCCTGCTCCTGGGCTCG SEQ. ID. NO. 59 | 7 |
| EGFR; EGFR; EGFR; EGFR | CGGTAGAGTGAATTGCCTGTTTGTTGCAAGTTGGGACTTTGCTGGGCTGG SEQ. ID. NO. 60 | 7 |
| RARRES2 | CCTGCAGTTTTAGCAAAGTTCCCTGCCCACGCTAGGAATCAGTCAGTTCG SEQ. ID. NO. 61 | 7 |
| SLC16A9 | AAATCGGTATGCCCTAACAGTTTCTTATATTTGAGTTGGCTTCAGCTTCG SEQ. ID. NO. 62 | 10 |
| SLC16A9 | GAATATTTCCCTCTATTTGTCATGCAAATGTATCAGTCTCCTCTTCTGCG SEQ. ID. NO. 63 | 10 |
| IGF2; INS-IGF2; INS-IGF2 | CTTAGAGTGACACTTGGCAGTTACTTGACACCCTGGAATGTTGGTGGACG SEQ. ID. NO. 64 | 11 |
| AKT1; AKT1; AKT1 | CGGGCCCGGCCAGGCACCCAGATCCGTGGCTTGGACACGCTGCCCACACA SEQ. ID. NO. 65 | 14 |
| AKT1; AKT1; AKT1 | CGCTTAACCTTTCCGCTGTCGCCCCAGGCCCTCCCTGACTCCCTGTGGGG SEQ. ID. NO. 66 | 14 |
| AKT1; AKT1; AKT1 | GAGTGGGTGCCGGCCGCAGGGGCACCACCTGGACTCCCTCAGGCTGGTCG SEQ. ID. NO. 67 | 14 |
| AKT1; AKT1; AKT1 | CGCGCCCCAGGCAGCTTCCCTCGACCCCCGCCCACTCGGCCTTGGCCTGC SEQ. ID. NO. 68 | 14 |
| IGF1R | TTTCGCCTCTGCCTCTGTGTGCCTCTGGGCTGTAAGCTTTAGTTTGCACG SEQ. ID. NO. 69 | 15 |
| IGF1R | CGTTCAGGCCTTGGCAACTGACGCTCTGCAGAACGGACCAGGAGTGTGCG SEQ. ID. NO. 70 | 15 |
| IGF1R | CGCCTCTGCCTCTGTGTGCCTCTGGGCTGTAAGCTTTAGTTTGCACGGTT SEQ. ID. NO. 71 | 15 |
| IGF1R | GTGAGCAGTTTAGAGACAGATGAGACAGGCTTATGGTTTCCACTGGCTCG SEQ. ID. NO. 72 | 15 |
| IGF1R | GAGGGAAACAATTGAAACAGACAATCGCTCAGATACCAACACCAAGTTCG SEQ. ID. NO. 73 | 15 |
| TP53; WRAP53; TP53; TP53; TP53 | CGGACATTAGGTATTGTCAGTCTTTCTAATGTGGTATATCCTTGTGGTTG SEQ. ID. NO. 74 | 17 |
| GATA6 | GAGATTAATCCCTGAAATCAGGATTCCCTTACTTTAAAACATGGTGGCCG SEQ. ID. NO. 75 | 18 |
| GATA6 | CCTCGGGTTACCATCACCAATTTCTTGCCTATCTTACCAGAATTATTACG SEQ. ID. NO. 76 | 18 |
| GATA6 | AGTAAAAGTGTGGTTTGTATGTTCTTAAGTTGAGCATTTTCCCCAATTCG SEQ. ID. NO. 77 | 18 |

TABLE 3-continued

| UCSC_RefGene_Name | Coordinate_36 | Strand | Probe_SNPs | Probe_SNPs_10 |
|---|---|---|---|---|
| IL13RA2 | 114158507 | R | | |
| CTNNB1; CTNNB1; CTNNB1 | 41240378 | F | rs5743389 | |
| RARRES2 | 149667977 | F | | |
| RARRES2 | 149668823 | R | | |
| RARRES2 | 149668230 | R | | |
| RARRE52 | 149657220 | F | | rs80070869 |
| EGFR; EGFR; EGFR; EGFR | 55156126 | F | | |
| RARRES2 | 149658921 | R | | |
| SLC16A9 | 61138164 | R | | |
| SLC16A9 | 61104217 | F | | |
| IGF2; INS-IGF2; INS-IGF2 | 2127583 | R | | |
| AKT1; AKT1; AKT1 | 104326330 | F | | rs61759769 |
| AKT1; AKT1; AKT1 | 104306936 | R | | rs3840005 |
| AKT1; AKT1; AKT1 | 104326517 | F | rs61759766 | |
| AKT1; AKT1; AKT1 | 104326406 | F | rs11848695 | rs61759768 |
| IGF1R | 97068050 | R | | rs45453898 |
| IGF1R | 97067963 | R | | |
| IGF1R | 97068005 | F | rs45453898 | |
| IGF1R | 97029927 | R | | |
| IGF1R | 97161441 | F | | |
| TP53; WRAP53; TP53; TP53; TP53 | 7529103 | R | | |
| GATA6 | 18012219 | F | | |
| GATA6 | 8011466 | F | | |
| GATA6 | 18011888 | R | | |

| UCSC_RefGene_Name | UCSC_RefGene_Accession |
|---|---|
| IL13RA2 | NM_000640 |
| CTNNB1; CTNNB1; CTNNB1 | NM_001904; NM_001098209; NM_001098210 |
| RARRES2 | NM_002889 |
| RARRES2 | NM_002889 |
| RARRES2 | NM_002889 |
| RARRES2 | NM_002889 |
| EGFR; EGFR; EGFR; EGFR | NM_201283; NM_201284; NM_201282; NM_005228 |
| RARRES2 | NM_002889 |
| SLC16A9 | NM_194298 |
| SLC16A9 | NM_194298 |
| IGF2; INS-IGF2; INS-IGF2 | NM_001007139; NR_003512; NM_001042376 |
| AKT1; AKT1; AKT1 | NM_001014431; NM_005163; NM_001014432 |
| AKT1; AKT1; AKT1 | NM_005163; NM_001014431; NM_001014432 |
| AKT1; AKT1; AKT1 | NM_001014431; NM_005163; NM_001014432 |

TABLE 3-continued

| | |
|---|---|
| AKT1; AKT1; AKT1 | NM_001014431; NM_005163; NM_001014432 |
| IGF1R | NM_000875 |
| IGF1R | NM_000875 |
| IGF1R | NM_000875 |
| IGF1R | NM_000875 |
| IGF1R | NM_000875 |
| TP53; WRAP53; TP53; TP53; TP53 | NM_000546; NM_00114390; NM_001126113; NM_001126112; NM_001126114 |
| GATA6 | NM_005257 |
| GATA6 | NM_005257 |
| GATA6 | NM_005257 |

| UCSC_RefGene_Name | UCSC_RefGene_Group | UCSC_CpG_Islands_Name |
|---|---|---|
| IL13RA2 | TSS200 | |
| CTNNB1; CTNNB1; CTNNB1 | 5'UTR; 5'UTR; 5'UTR | |
| RARRES2 | Body | chr7:150037459-150039031 |
| RARRES2 | 5'UTR | chr7:150037459-150039031 |
| RARRES2 | Body | chr7:150037459-150039031 |
| RARRES2 | Body | chr7:150037459-150039031 |
| EGFR; EGFR; EGFR; EGFR | Body; Body; Bod Body | |
| RARRES2 | 5'UTR | chr7:150037459-150039031 |
| SLC16A9 | 5'UTR | chr10:61468610-61469999 |
| SLC1BA9 | Body | |
| IGF2; INS-IGF2; INS-IGF2 | TSS200; Body; Body | |
| AKT1; AKT1; AKT1 | Body; Body; Body | chr14:105251401-105251617 |
| AKT1; AKT1; AKT1 | 3'UTR; 3'UTR; 3'UTR | chr14:105239263-405239591 |
| AKT1; AKT1; AKT1 | Body; Body; Body | chr14:105251401-105251617 |
| AKT1; AKT1; AKT1 | Body; Body; Body | chr14:105251401-105251617 |
| IGF1R | Body | chr15:99250794-99251018 |
| IGF1R | Body | chr15:99250794-99251018 |
| IGF1R | Body | chr15:99250794-99251018 |
| IGF1R | Body | |
| IGF1R | Body | |
| TP53; WRAP53; TP53; TP53; TP53 | 5'UTR; TSS1500; 5'UTR; 5'UTR; 5'UTR | chr17:7589290-7589503 |
| GATA6 | Body | chr18:19756794-19757080 |
| GATA6 | Body | chr18:19756794-49757080 |
| GATA6 | Body | chr18:19756794-19757080 |

TABLE 3-continued

| UCSC_RefGene_Name | Relation_to_UCSC_CpG_Island | DMR | Enhancer | HMM_Island |
|---|---|---|---|---|
| IL13RA2 | | | | |
| CTNNB1; CTNNB1; CTNNB1 | | | TRUE | |
| RARRES2 | N_Shore | CDMR | | |
| RARRES2 | Island | | TRUE | 7:149668458-149669951 |
| RARRES2 | N_Shore | CDMR | | |
| RARRES2 | N_Shore | CDMR | | |
| EGFR; EGFR; EGFR; EGFR | | | TRUE | |
| RARRES2 | Island | | TRUE | 7:14966845-8449669951 |
| SLC1649 | N_Shore | RDMR | | |
| SLC16A9 | | | TRUE | |
| IGF2; INS-IGF2; INS-IGF2 | | RDMR | | |
| AKT1; AKT1; AKT1 | S_Shelf | | | 14:104326321-404326556 |
| AKT1; AKT1; AKT1 | N_Shelf | | TRUE | |
| AKT1; AKT1; AKT1 | S_Shelf | | | 14:104326321-404326556 |
| AKT1; AKT1; AKT1 | S_Shelf | | | 14:104326321-404326556 |
| IGF1R | N_Shore | | | 15:97067915-97068101 |
| IGF1R | N_Shore | | | 15:97067915-97068101 |
| IGF1R | N_Shore | | | 15:97067915-97068101 |
| IGF1R | | DMR | TRUE | |
| IGF1R | | | TRUE | |
| TP53; WRAP53; TP53; TP53; TP53 | N_Shore | | | |
| GATA6 | S_Shore | RDMR | | |
| GATA6 | S_Shore | RDMR | | |
| GATA6 | S_Shore | RDMR | | |

| UCSC_RefGene_Name | Regulatory_Feature_Name | Regulatory_Feature_Group | DHS |
|---|---|---|---|
| IL13RA2 | | | |
| CTNNB1; CTNNB1; CTNNB1 | | | |
| RARRES2 | | | TRUE |
| RARRES2 | | | TRUE |
| RARRES2 | | | TRUE |
| RARRES2 | | | |
| EGFR; EGFR; EGFR; EGFR | | | |
| RARRES2 | | | TRUE |
| SLC16A9 | | | |

TABLE 3-continued

| | | |
|---|---|---|
| SLC16A9 | | |
| IGF2; INS-IGF2; INS-IGF2 | | |
| AKT1; AKT1; AKT1 | | |
| AKT1; AKT1; AKT1 | | |
| AKT1; AKT1; AKT1 | | |
| AKT1; AKTI; AKT1 | | |
| IGF1R | | |
| IGF1R | | |
| IGF1R | | |
| IGF1R | | TRUE |
| IGF1R | | TRUE |
| TP53; WRAP53; TP53; TP53; TP5314-7588214-7588490 | Promoter_Associated_cell_type_specific | |
| GATA6 | | |
| GATA6 | | |
| GATA6 | | |

Example 8

Malignant Adrenocortical Tumor-Related Molecules are Therapeutic Targets for ACC This example demonstrates that treatment of adrenocortical tissue samples with a demethylating agent significantly alters gene expression of malignant adrenocortical tumor-related molecules and indicate demethylating agents as possible therapeutic agents for treating ACC.

Studies were performed on human adrenocortical cells and the effect of decitabine on gene-expression of HTN3, H19, S100A10, FAM129A, HOPX, TAC1, UCHL1, ERBB3, BEGNT5, RUNX2, GJA3, and BGN was evaluated. The demethylating agent decitabine was found to significantly alter the expression of a number of malignant adrenocortical tumor-related molecules, including H19, S100A10, HOPX, ERBB3, and RUNX2 (see Table 4 below). As such, these studies indicate that demethylating agents are agents capable of regulating malignant adrenocortical tumor-related molecules and can be used to treat ACC.

TABLE 4

NCI-H295R Decitabine Treated Cells Average Upregulated Gene Expression and Mean Hypermethylation Tissue Comparisons.

| Gene Symbol | Decitabine Gene Expression Fold Change (adj p ≤ 0.05) | Benign vs Normal Methylation Difference (adj p ≤ 0.01) | Primary ACC vs Normal Methylation Difference (adj p ≤ 0.01) | Metastatic ACC vs Normal Methylation Difference (adj p ≤ 0.01) | Primary ACC vs Benign Methylation Difference (adj p ≤ 0.01) | Metastatic ACC vs Benign Methylation Difference (adj p ≤ 0.01) | Primary vs Metastatic ACC Methylation Difference (adj p ≤ 0.01) |
|---|---|---|---|---|---|---|---|
| HTN3 | 43.14 | | | | | | 1.62 |
| H19 | 19.17 | | | | 1.24 | | |
| S100A10 | 17.38 | | | | 1.31 | | |
| FAM129A | 13.69 | | | | | | 1.26 |
| HOPX | 12.82 | | 1.81 | | 1.82 | | 1.97 |
| TAC1 | 11.24 | | 0.50 | 1.59 | | 1.47 | |
| UCHL1 | 10.60 | | 1.43 | 1.32 | | 1.25 | |
| ERBB3 | 9.30 | | 1.51 | | 1.74 | | 1.32 |
| B3GNT5 | 8.79 | | | 1.58 | | 2.03 | |
| RUNX2 | 8.74 | | 1.61 | | 1.51 | | |
| GJA3 | 8.22 | | 1.35 | | | | |
| BGN | 8.16 | 1.79 | 1.85 | | | | |

Example 9

Diagnosis of a Malignant Adrenocortical Tumor

This example describes particular methods that can be used to diagnose or prognose a malignant adrenocortical tumor in a subject, such as ACC in a human, by detecting methylation of target nucleic acids (such as hypermethylated CpG sites of KCTD12, KIRREL, SYNGR1, and/or NTNG2 nucleic acids) in a sample from a subject, thereby diagnosing the subject with a malignant adrenocortical tumor. However, one skilled in the art will appreciate that methods that deviate from these specific methods can also be used to successfully methylate nucleic acids in a sample and determine a diagnosis for the subject.

In one example, the diagnosis of a malignant adrenocortical tumor is determined by detecting abnormal methylation (such as presence and/or an increase in methylation of KCTD12, KIRREL, SYNGR1, NTNG2, IL13RA2, HTR2B, CCNB2, RARRES2, and/or SLC16A9 nucleic acids) in the sample obtained from the subject. A tissue biopsy sample is procured from the adrenal cortex of a subject suspected of having a malignant adrenocortical tumor, DNA is extracted from the sample using a DNA isolation kit (for example using a commercial kit such as described in Example 1). DNA is bisulfite-converted (such as by using the EZ DNA Methylation Gold Kit, Zymo Research Corporation, Irvine, California) according to the manufacturer's protocol with a modified thermocycling procedure as suggested by Illumina (San Diego, Calif.) (16 cycles of 95° C. 30 sec, 50° C. 60 min) and assayed to detect methylation status (such as by use of Illumina Infinium HD Methylation Assay Kit (Illumina, Inc, San Diego, Calif.)). Detection of a beta difference of ≥0.2 in methylation of a DNA sample relative to control values (e.g., methylation levels in a benign adrenocortical tumor or a reference value known to be indicative of methylation levels in a benign adrenocortical tumor) is indicative that the subject has a malignant adrenocortical tumor.

The results of the test are provided to a user (such as a clinician or other health care worker, laboratory personnel, or patient) in a perceivable output that provides information about the results of the test. The output is a graphical output showing a cut-off value or level that indicates the presence of a malignant adrenocortical tumor. The output is communicated to the user, for example by providing an output via physical, audible, or electronic means (for example by mail, telephone, facsimile transmission, email, or communication to an electronic medical record). The output is accompanied by guidelines for interpreting the data, for example, numerical or other limits that indicate the presence or absence of metastasis. The guidelines need not specify whether metastasis is present or absent, although it may include such a diagnosis. The indicia in the output can, for example, include normal or abnormal ranges or a cutoff, which the recipient of the output may then use to interpret the results, for example, to arrive at a diagnosis, prognosis, or treatment plan. Based upon the results, a therapeutic regimen is or is not recommended.

Example 10

Clinical Trial Evaluating Diagnostic and Prognostic Molecular Markers in Adrenal Neoplasms This example describes a clinical trial evaluating the accuracy of the disclosed molecular markers of malignant adrenal neoplasms in fine needle aspiration (FNA) biopsy and surgically resected samples.

Adrenal neoplasms are one of the most prevalent of all human tumors. The prevalence of adrenal incidentaloma is approximately 5% on abdominal imaging, but the prevalence can be as high as 10% in the elderly. As the U.S. population ages, the management of adrenal incidentaloma will be an increasingly important issue in health care. As outlined in a NIH State-of-the-Science statement on the "Management of the Clinically Inapparent Adrenal Mass (Incidentaloma)" there are significant limitations in diagnostic evaluation of these tumors because there are no reliable criteria for predicting the risk of malignancy, outside of obvious metastatic or locoregional disease. This results in many patients having adrenalectomy to exclude a cancer diagnosis.

There are no reliable preoperative clinical, imaging or biochemical tests available to distinguish between primary benign and malignant adrenocortical neoplasms in the absence of obvious metastatic disease or locoregional invasion. Imaging features such as tumor heterogeneity, irregular tumor border, hemorrhage, necrosis, rapid tumor growth rate, tumor Hounsfield unit >10-20 on non-contrast CT scan, and intravenous contrast washout of 40% or less after 15 minutes are more common in malignant tumors but are not reliable enough to avoid the need for adrenalectomy to exclude a cancer diagnosis nor to forgo continued follow up. In patients with a history of an extra-adrenal malignancy, an adrenal incidentaloma may indicate metastatic disease in 32% to 73% of cases depending on the primary tumor site and patient age. The tumor size of adrenal neoplasm measured by imaging studies has been used as a preoperative surrogate marker for a malignant tumor and for recommending resection, but this criterion is not precise for tumors that measure >2 cm but <6 cm. Even when the tumor is 6 cm or larger, the reported risk of malignancy ranges from 5% to 98%, depending on the study cohort. In many centers, a size threshold of >6 cm has been used as an absolute indication for adrenalectomy. However, it is unclear whether adrenal tumors between 2 cm and 6 cm should be removed or monitored, whereas most experts recommend monitoring tumors <4 cm in size depending on the patient's age.

Fine needle aspiration biopsy and cytologic examination has not been routinely used to evaluate adrenal neoplasm at most centers because it is not accurate enough for distinguishing between primary benign and malignant adrenocortical tumors. However, in patients with a concurrent malignancy or history of extra-adrenal malignancy, fine needle aspiration biopsy may be useful for detecting metastatic disease to the adrenal gland after biochemical exclusion of a hyperfunctioning tumor, especially a pheochromocytoma. Fine needle aspiration of the adrenal gland is associated with a low risk (<1%) of complications such as bleeding, pneumothorax, pain, and rarely tumor seeding along the needle track.

Postoperative histopathologic examination to distinguish between malignant and benign primary adrenal tumors is also difficult and problematic. For adrenocortical neoplasms, the Weiss histologic criterion is most commonly used, but is imprecise. This means even patients with histologically diagnosed adrenocortical adenoma require continued follow-up because some will develop metastatic disease.

In summary, although adrenocortical carcinomas tend to be larger than benign tumors, tumor size, even when combined with imaging features, is not accurate enough to use for making management decisions for most tumors that are less than 6 cm. Furthermore, imaging studies such as MRI and CT scans underestimate adrenal tumor size by 16% to 47%, and are less accurate in smaller tumors. Therefore, there is a significant need for biomarkers that can distinguish benign from malignant adrenal tumors for determining the need for adrenalectomy, for selecting the appropriate surgical approach, and for determining the appropriate follow up.

The inventors have identified several novel diagnostic markers with excellent accuracy for distinguishing between benign and primary malignant adrenocortical tumors (see, for example, Tables 5 and 6, below).

Figure 7:
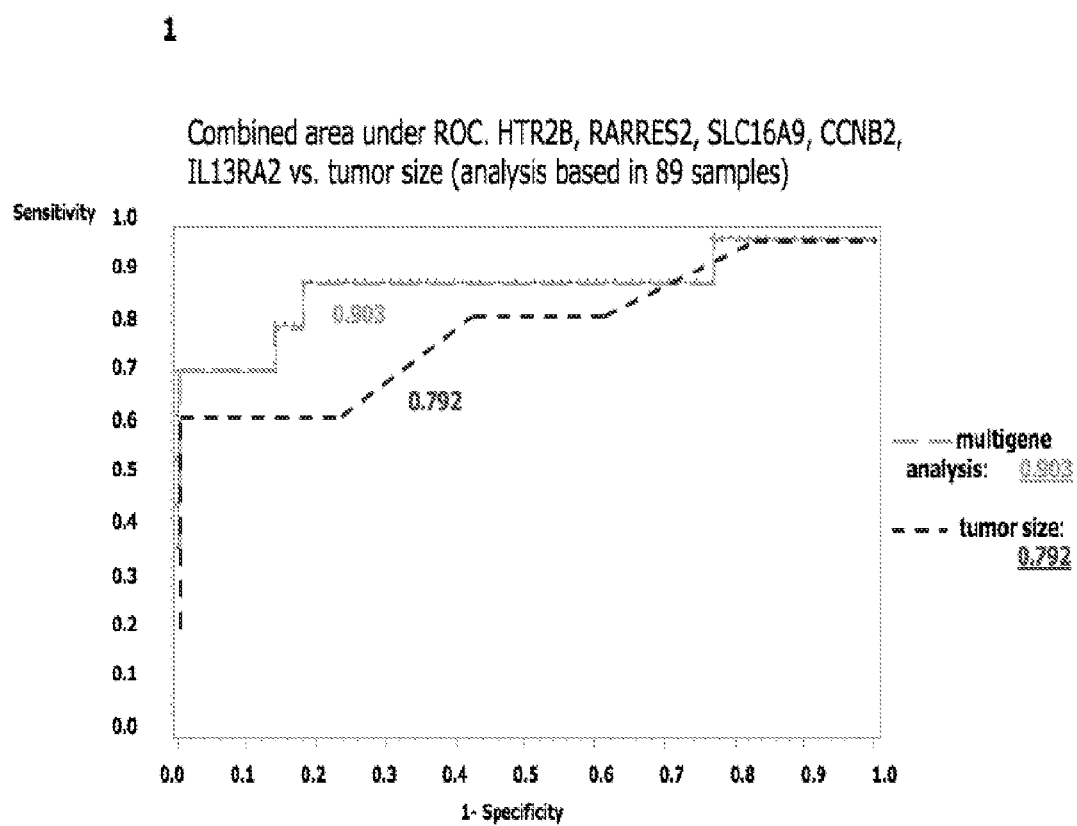
FIG. 7 is an area under receiver operating characteristics curve (AUC) when 5 biomarkers with the highest individual AUC values (IL13RA2, HTR2B, CCNB2, RARRES2, SLC16A9) were combined as compared to tumor size as a clinical parameter for the diagnosis of adrenocortical carcinoma (AUC: 0.79). An AUC of 1 represents the perfect diagnostic biomarker without any false-negative and false-positive results.

The combination of the highest AUC 5 genes did not show improvement in diagnostic accuracy when compared to the highest individual value (AUC: 0.913 for IL13RA2 vs. 0.907 all 5 genes in combination). Comparison of the 5 markers with the highest AUC to tumor size, one of the main current clinical criterions used to assess risk of malignancy, demonstrates that the candidate markers in combination are more accurate than tumor size (FIG. 7).

Figure 8:
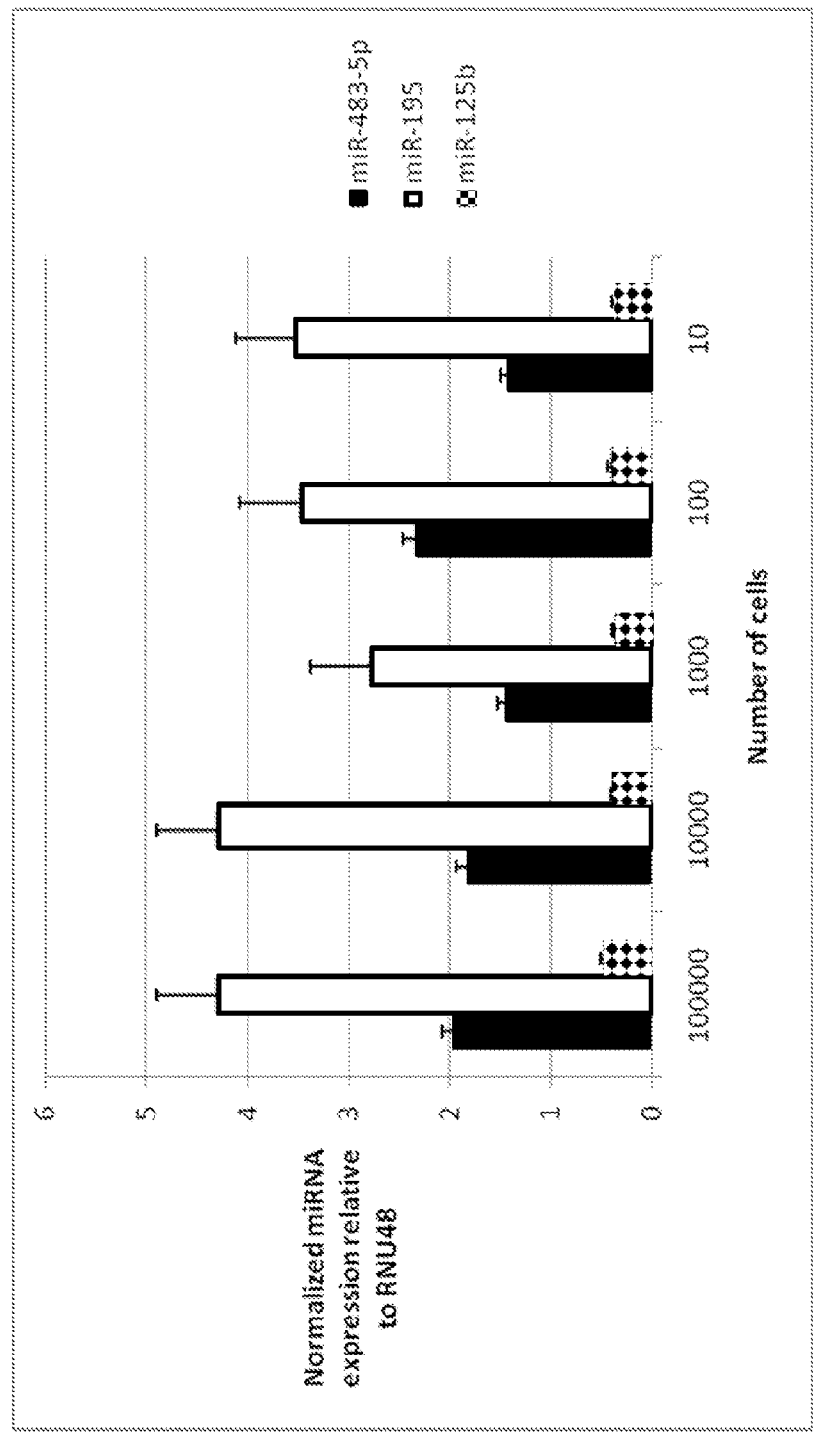
FIG. 8 is a bar graph illustrating microRNA expression level by quantitative PCR.

While these markers can be used in post-surgical resection samples in equivocal cases, one of the most helpful clinical applications of these markers would be preoperatively in clinical fine needle aspiration biopsy samples. Therefore, the present trial is designed to test the feasibility and accuracy of using this panel of markers in fine needle aspiration samples of patients with adrenal neoplasm with the exception of pheochromocytoma that are greater than 2 cm. For cytologic examination, fine needle aspiration biopsy has a 67%-100% adequacy rate. Previous studies in thyroid fine needle aspiration biopsy samples indicate an adequate yield of nucleic acid for multigene expression analysis. Moreover, the inventors have disclosed herein the ability to determine gene expression levels in as little as 10 adrenocortical carcinoma cells by quantitative RT PCR (FIG. 8).

TABLE 5

Messenger RNA candidate diagnostic markers

| Gene Symbol | P value* (1) | P value* (2) | AUC (1) | AUC (2) |
|---|---|---|---|---|
| PRLR | 0.011 | 0.01 | 0.74 | 0.75 |
| HSD3B2 | <0.01 | 0.01 | 0.77 | 0.75 |
| PRG-3 | <0.01 | 0.01 | 0.76 | 0.75 |
| LGR5 | 0.01 | 0.008 | 0.74 | 0.76 |
| FREM2 | 0.006 | <0.01 | 0.70 | 0.80 |
| ALDH1A1 | <0.01 | <0.01 | 0.76 | 0.81 |
| CCNB2 | <0.01 | <0.01 | 0.86 | 0.84 |
| SLC16A9 | <0.01 | <0.01 | 0.80 | 0.87 |
| RARRES2 | <0.01 | <0.01 | 0.86 | 0.88 |
| HTR2B | <0.01 | <0.01 | 0.87 | 0.88 |
| IL13RA2 | <0.01 | <0.01 | 0.90 | 0.91 |

Abbreviations: AUC, area under the receiver operating characteristic curve.
*P values were determined by Mann-Whitney test.
(1) = Analysis based on benign (54 adrenocortical adenoma, 20 adrenocortical hyperplasia, 4 normal adrenocortical tissue) and malignant (11 primary adrenocortical carcinomas) tissue samples.
(2) = Subset analysis of benign vs. malignant adrenocortical tumors excluding Conn's syndrome (n = 30) and normal (n = 4) adrenocortical tissue samples.

TABLE 6

MicroRNA Candidate Diagnostic Markers

| microRNA | p value (Benign v. Malignant) | AUC |
|---|---|---|
| miR-665 | 0.0042 | 0.83 |
| miR-483-5p* | <0.0001 | 0.94 |
| miR-483-3p* | <0.0001 | 0.94 |
| miR-23b | 0.0376 | 0.78 |
| miR-195* | 0.014 | 0.77 |
| miR-125b | 0.0173 | 0.76 |

Abbreviations: AUC, area under the receiver operating characteristic curve.
P values were determined by Mann-Whitney test.
Analysis based on benign (54 adrenocortical adenoma) and malignant (11 primary adrenocortical carcinoma) tissue samples.
*Also identified as a prognostic marker in patients with adrenocortical carcinoma
Only microRNAs with AUC of 0.75 or higher listed and will be analyzed in this study Thus, the present protocol is designed to determine the feasibility and accuracy of using novel molecular markers of malignant adrenal neoplasm in fine needle aspiration (FNA) biopsy and surgically resected samples. Objectives of this trial are the following: (1) to evaluate the feasibility of molecular testing in adrenal neoplasm FNA biopsy samples; to determine the accuracy of novel diagnostic molecular markers in clinical adrenal FNA biopsy and surgically resected samples; and to analyze the gene expression level relative to disease-free survival and overall survival in patients with adrenocortical carcinoma.

I. Eligibility Assessment and Enrollment
  i. Inclusion Criteria
    a. An individual with a primary localized adrenal neoplasm greater than 2 cm in size
    b. Age greater than 18 years
    c. Adults must be able to understand and sign the informed consent document
    d. Patients must have an ECOG performance score of 0-2.
    e. Patients must have laboratory and physical examination parameters within acceptable limits by standard of practice guidelines prior to biopsy or surgery
  Note: Patients with malignancies other than ACC may be eligible
  ii. Exclusion Criteria
    a. Biochemically proven Pheochromocytoma
  iii. Patient Registration
    Patients will be registered on the trial by the principal investigator or his designee using a protocol specific registration form after signing the appropriate informed consent or agreeing by assent.

Figure 9:
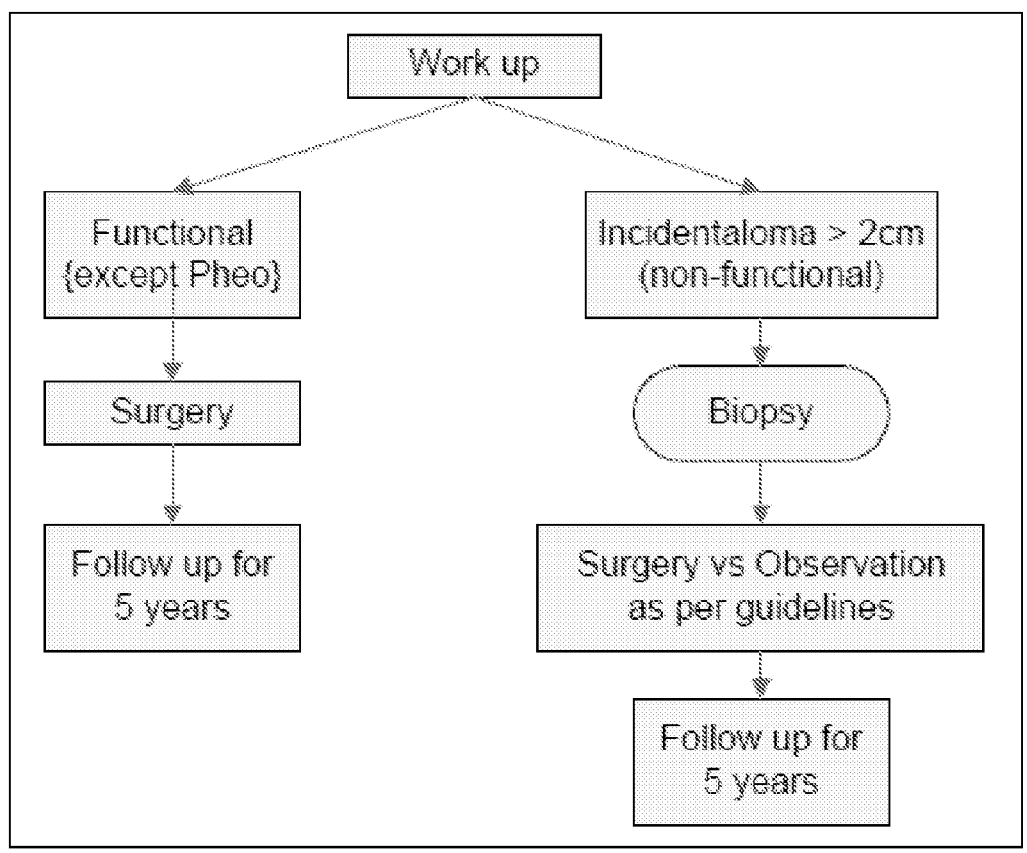
FIG. 9 is a flow chart illustrating the implementation of a clinical trial.

II. Study Implementation
  This is a prospective study of individuals with an adrenal mass. Individuals will have routine clinical work up for an adrenal mass; those with nonfunctioning tumors larger than 2 cm will undergo CT guided fine-needle aspiration biopsy. For patients who require adrenalectomy for a functioning tumor, the surgically resected tissue sample will be used for the molecular analysis (see FIG. 9).

III. Study Evaluation
  Patients will undergo the following evaluations which may be performed within 4 weeks of enrollment:
  Detailed History and Physical Examination including, vital signs, ECOG status, demographic information and family history.
  Imaging studies: Adrenal protocol CT scan with and without intravenous contrast; and/or FDG PET/CT scan.
  Laboratory evaluations: CBC with differential; Chem 20 [Sodium (Na), Potassium (K), Chloride (Cl), Total CO2 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid]; PT/PTT.

Biochemical testing; Serum renin and plasma aldosterone levels; 24-hour urinary cortisol level; low dose (1-2 mg) dexamethasone suppression test; and serum fractionated plasma normetanephrine and metanephrine.

IV. CT Guided Fine Needle Aspiration Biopsy of Adrenal Neoplasm

Patients with confirmed non-functional tumors greater than 2 cm in greatest dimension will undergo CT guided fine needle aspiration. Tissue will be handled as described above.

V. Surgical Intervention

Figure 10:
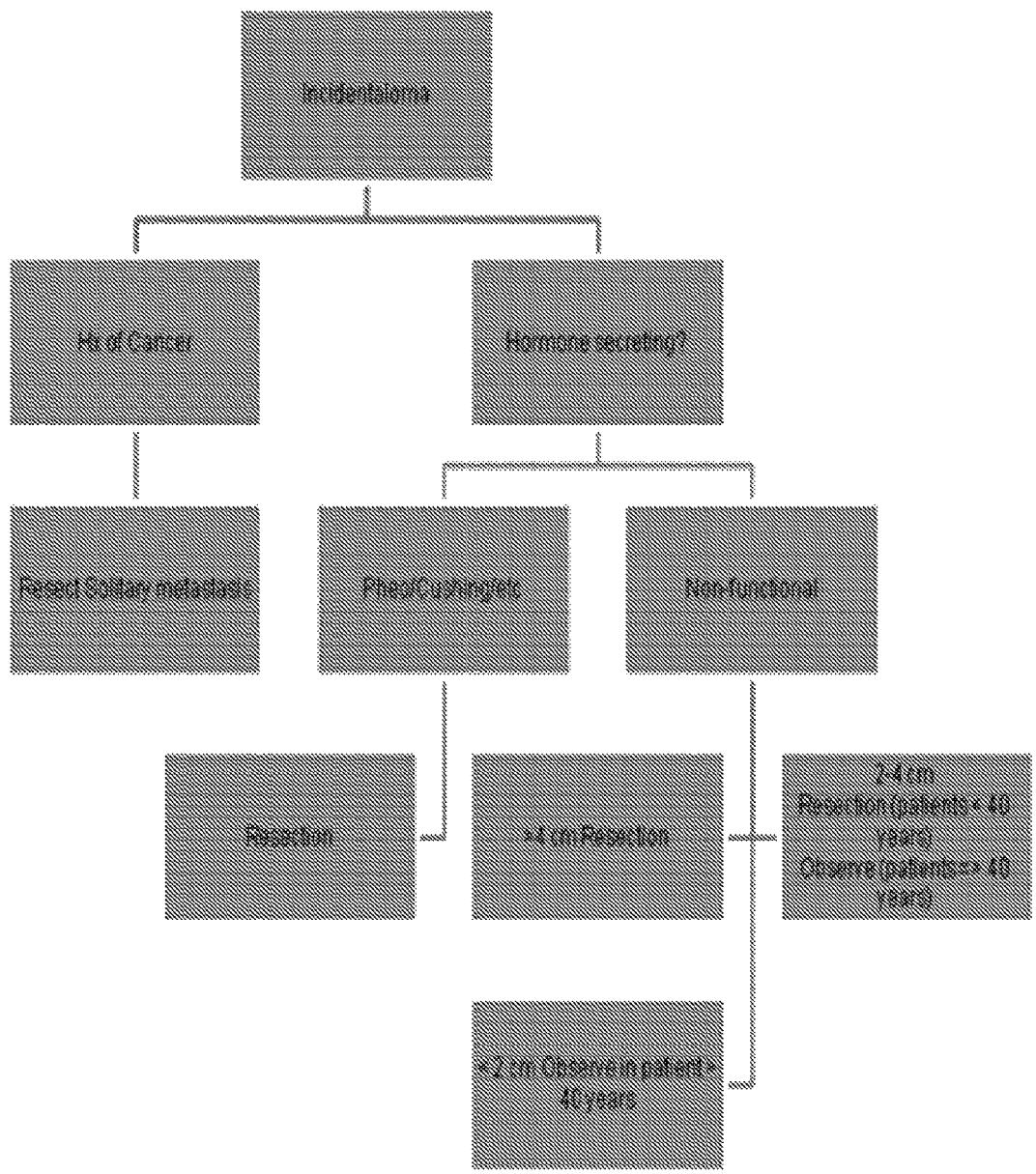
FIG. 10 is a flow chart illustrating a clinical algorithm for adrenal neoplasm work up and indication for adrenalectomy.

Patients with an adrenal neoplasm will have an adrenalectomy based on our standard clinical practice (see FIG. 10).

VI. Follow-up Examinations

Patients who are found to have an adrenal neoplasm which does not require resection will undergo the following evaluations every year for 5 years:
  i. physical exam to include vital signs and ECOG status;
  ii. laboratory evaluations—all tumors; 24-hour urinary cortisol level; low dose (1-2 mg) dexamethasone suppression test; serum fractionated plasma normetanephrine and metanephrine; serum renin and plasma aldosterone levels; and
  iii. Adrenal protocol CT scan with and without intravenous contrast.

Patients who undergo an adrenalectomy will undergo the following evaluations every year for 5 years:
  i. Physical exam to include vital signs and ECOG status;
  ii. Laboratory Evaluations: 24-hour urinary cortisol level; low dose (1 mg) dexamethasone suppression test; and
  iii. CT scan of the chest, abdomen and pelvis to exclude disease recurrence (even if found to be benign on histopathology).

Patients may be evaluated on a more frequent basis if they develop symptoms possibly associated with their adrenal neoplasm. Patients who meet the criteria for adrenalectomy at any time during the follow up period will be offered surgical intervention.

VII. Research Specimen Collection and Analysis
  i. Adrenal biopsy and surgical specimens: Half of the FNA sample will be sent to the department of pathology, and the other half to an endocrine oncology laboratory. The biopsy sample will be immediately placed in RNAlater®, transported on ice, and stored in −80° C. until used for molecular analysis. For the surgical resection specimen, the samples will be immediately snap frozen in liquid nitrogen and stored in −80° C. until molecular analysis. Samples will be immediately transported to evaluation laboratory. The diagnostic accuracy of the candidate gene expression levels will be determined based on the histologic diagnosis and follow up time of over 5 years. Gene expression levels will also be analyzed relative to disease-free survival and overall survival in patients with adrenocortical carcinoma determined. All the candidate gene expression level thresholds/cutoffs will be normalized to an adrenocortical carcinoma cell line and universal RNA to account for interassay variability.
  ii. Handling of Specimens for Research Purposes: Specimens will be collected, stored and analyzed as noted above. Samples will be labeled with the date and time of acquisition, the type of tissue and patient study number in the Labmatrix database.
  iii. Off Study Criteria: Patients will be removed from the study if any of the following criteria are met: the patient requests withdrawal from the study; the patient is consistently non-compliant with follow-up appointments; the patient is consistently non-compliant with imaging studies; or completion of the protocol specified follow up period.

VIII. Supportive Care

Supportive care will be provided to the patients as is indicated by their endocrine neoplasm and procedures performed. The clinical evaluations done as part of this protocol may detect an unsuspected malignancy or other serious medical conditions. When this occurs, referral for treatment is expedited. If a participant requires cancer treatment and meets the eligibility criteria for an active CCR protocol, IX. Data Collection Data prior to and during the course of the patient's participation will be collected in order to monitor patient eligibility, and will include review of medical and family history records, non-invasive imaging, blood work, and urinary studies.
  i. Toxicity Criteria: This study will utilize the Common Terminology Criteria for Adverse Events (CTCAE) version 4 for toxicity and adverse event reporting. CTCAE version 4 is available on the World Wide Web at ctep.info.nih.gov. All appropriate treatment areas should have access to a copy of the CTCAE version 4.
  ii. Statistical Considerations: A primary objective of this study is to determine the ability of a set of markers to distinguish between benign and malignant adrenocortical neoplasms. Patients with adrenal neoplasms greater than 2 cm will be enrolled onto the trial and a set of novel diagnostic and prognostic molecular markers will be evaluated. It is anticipated that approximately 10% of patients enrolled will have a malignant mass and 90% will be benign. Based upon pilot data, it is expected that the classification accuracy of the proposed methods will be 90% or better, but this study is intended to determine if this is correct and to improve the precision of the estimate of these results.

Assuming that 10% of patients have a malignant mass, it would be desirable to estimate the fraction of these correctly identified as being malignant, with a confidence interval width of +/10% or less. Enrolling thirty five (35) patients who are ultimately determined to have malignant masses would permit an associated two-sided 95% confidence interval around 90% to have a width of +/−9.9%. It would also be desirable to estimate the fraction correctly identified as being benign. Enrolling 200 patients who are ultimately determined to have benign masses would permit an associated two-sided 95% confidence interval around 90% to have a width of +/−4.2%. Greater numbers of patients and a higher probability of correct classification will result in greater precision of the estimated classification probability.

Because the estimate is likely to be much less precise for identifying the malignant cases than for identifying those that are benign, it is important to enroll sufficient patients to ensure that at least 35 malignant cases are evaluated. Thus, if 10% is a reasonable estimate of the proportion of all patients expected to have malignant masses, it would be desirable to enroll 350-500 total patients in order to have a reasonably high probability of obtaining at least 35 with malignant masses. Classification will be done using standard logistic regression models and ROC curves as appropriate. The sensitivity and specificity will be reported along with 95% two-sided confidence intervals, and an AUC relative to the ROC curve will be determined. It is assumed that 50 patients per year may enroll onto this study. Thus, an accrual period of 10 years is anticipated in order to enroll up to 500 subjects.

X. Rationale for Subject Selection

Subjects will be selected for this protocol based on a clinical diagnosis of an adrenal neoplasm. Only patients at low risk for a malignant tumor will undergo fine needle aspiration biopsy and those requiring an adrenalectomy will have surgical resected tissue to test the markers. Such a selection criteria for performing the fine needle aspiration biopsy would allow us to select those patients most likely to represent a diagnostic dilemma and to benefit from such an analysis.

XI. Data Reporting i. Routine Data Reporting: All details of patient evaluation, management and treatment will be documented in the patient medical record. Only the following information will be captured on the CRFs: detailed demographic information including family history; laboratory results; and imaging results (CT scan).

ii. Serious Adverse Event Reporting Requirements: The following events will be reported: all deaths with the exception of those due to progressive disease; all grade 3 and 4 (CTCAE) events that are not listed in the consent form and that are possibly, probably or definitely related to the research; all serious adverse events (SAEs) that are not listed in the consent form, but are possibly, probably or definitely related to the research (with the exception of death due to progressive disease). An SAE is defined as an untoward medical occurrence that: resulted in death; was life-threatening; required or prolonged hospitalization; caused persistent or significant disability/incapacity; resulted in congenital anomalies or birth defects; or required intervention to prevent permanent impairment or death.

iii. Adverse Event Reporting in the Continuing Review Report: The following events will be presented to provide the information necessary to clearly identify risks to participants and to make a risk:benefit determination: all Grade 2 events that are not in the consent form, but are possibly, probably or definitely related to the research; all Grade 3 and 4 events that are possibly, probably or definitely related to the research; all Grade 5 events regardless of attribution; and all Serious Events regardless of attribution.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method, consisting of:
obtaining a sample comprising genomic DNA from a subject at risk of acquiring or suspected to have an adrenocortical tumor;
isolating genomic DNA from the sample; and
measuring a level of methylation in one or more genomic CpG dinucleotide sequences within one or more of malignant adrenocortical tumor-related molecules in genomic DNA isolated sample obtained from the subject at risk of acquiring or suspected to have an adrenocortical tumor,
wherein the one or more malignant adrenocortical tumor-related molecules comprise at least one of SLC16A9, IL13RA2, HTR2B, CCNB2, RARRES2, KCTD12, KIRREL, SYNGR1 or NTNG2.

2. The method of claim 1, wherein the measuring comprises measuring the level of methylation in one or more genomic CpG dinucleotide sequences within any two of KCTD12, KIRREL, SYNGR1, NTNG2, RARRES2, SLC16A9, IL13RA2, HTR2B, and CCNB2, any three of KCTD12, KIRREL, SYNGR1, NTNG2, RARRES2, SLC16A9, IL13RA2, HTR2B, and CCNB2, any four of KCTD12, KIRREL, SYNGR1, NTNG2, RARRES2, SLC16A9, IL13RA2, HTR2B, and CCNB2, any five of KCTD12, KIRREL, SYNGR1, NTNG2, RARRES2, SLC16A9, IL13RA2, HTR2B, and CCNB2, any six of KCTD12, KIRREL, SYNGR1, NTNG2, RARRES2, SLC16A9, IL13RA2, HTR2B, and CCNB2, any seven of KCTD12, KIRREL, SYNGR1, NTNG2, RARRES2, SLC16A9, IL13RA2, HTR2B, and CCNB2, any eight of KCTD12, KIRREL, SYNGR1, NTNG2, RARRES2, SLC16A9, IL13RA2, HTR2B, and CCNB2, or all nine.

3. The method of claim 1, wherein the method is used to distinguish a primary malignant adrenocortical tumor from a benign adrenocortical tumor.

4. The method of claim 1, wherein the one or more malignant adrenocortical tumor-related molecules comprise at least four of KCTD12, KIRREL, SYNGR1, NTNG2, RARRES2, SLC16A9, IL13RA2, HTR2B, and CCNB2.

5. The method of claim 1, wherein the one or more malignant adrenocortical tumor-related molecules comprise at least KCTD12, KIRREL, SYNGR1, NTNG2, RARRES2, SLC16A9, IL13RA2, HTR2B, and CCNB2.

6. A method, consisting of:
obtaining a sample comprising genomic DNA from a subject at risk of acquiring or suspected to have an adrenocortical tumor;
isolating genomic DNA from the sample; and
measuring a level of methylation in one or more genomic CpG dinucleotide sequences within one or more of malignant adrenocortical tumor-related molecules in genomic DNA isolated sample obtained from the subject at risk of acquiring or suspected to have an adrenocortical tumor,
wherein the one or more malignant adrenocortical tumor-related molecules comprise at least one of SLC16A9, IL13RA2, HTR2B, CCNB2, RARRES2, KCTD12, KIRREL, SYNGR1 or NTNG2; and
providing a therapeutic regimen based on the one or more methylated genomic CpG dinucleotide sequences.

7. A method, consisting of:
obtaining a sample comprising genomic DNA from a subject at risk of acquiring or suspected to have an adrenocortical tumor;
isolating genomic DNA from the sample; and
measuring a level of methylation in one or more genomic CpG dinucleotide sequences within one or more of malignant adrenocortical tumor-related molecules in genomic DNA isolated sample obtained from the subject at risk of acquiring or suspected to have an adrenocortical tumor,
wherein the one or more malignant adrenocortical tumor-related molecules comprise at least one of SLC16A9, IL13RA2, HTR2B, CCNB2, RARRES2, KCTD12, KIRREL, SYNGR1 or NTNG2; and contacting the isolated genomic DNA with sodium bisulfite prior to measuring the level of methylation in one or more genomic CpG dinucleotide sequences.

8. A method, consisting of:
obtaining a sample comprising genomic DNA from a subject at risk of acquiring or suspected to have an adrenocortical tumor;
isolating genomic DNA from the sample; and
measuring a level of methylation in one or more genomic CpG dinucleotide sequences within one or more of malignant adrenocortical tumor-related molecules in genomic DNA isolated sample obtained from the subject at risk of acquiring or suspected to have an adrenocortical tumor,
wherein the one or more malignant adrenocortical tumor-related molecules comprise at least one of SLC16A9, IL13RA2, HTR2B, CCNB2, RARRES2, KCTD12, KIRREL, SYNGR1 or NTNG2; and
contacting the isolated genomic DNA with sodium bisulfite prior to measuring the level of methylation in one or more genomic CpG dinucleotide sequences; and
amplifying the sodium bisulfite treated genomic DNA.

9. A method, consisting of:
obtaining a sample comprising genomic DNA from a subject at risk of acquiring or suspected to have an adrenocortical tumor;
isolating genomic DNA from the sample; and
measuring a level of methylation in one or more genomic CpG dinucleotide sequences within one or more of malignant adrenocortical tumor-related molecules in genomic DNA isolated sample obtained from the subject at risk of acquiring or suspected to have an adrenocortical tumor,
wherein the one or more malignant adrenocortical tumor-related molecules comprise at least one of SLC16A9, IL13RA2, HTR2B, CCNB2, RARRES2, KCTD12, KIRREL, SYNGR1 or NTNG2; and
administering to the subject an effective amount of a demethylating agent that alters activity and/or expression of one or more malignant adrenocortical tumor molecules, thereby treating a malignant adrenocortical tumor.

10. A method, consisting of:
contacting at least one malignant adrenocortical tumor-related nucleic acid in a sample from a subject at risk of acquiring or suspected to have a malignant adrenocortical cell proliferative disorder with a reagent that detects methylation, wherein the one or more malignant adrenocortical tumor-related nucleic acid comprises KCTD12, KIRREL, SYNGR1, NTNG2, RARRES2, SLC16A9, IL13RA2, HTR2B, and/or CCNB2; and
detecting methylation of the one or more malignant adrenocortical tumor-related nucleic acid comprising KCTD12, KIRREL, SYNGR1, NTNG2, RARRES2, SLC16A9, IL13RA2, HTR2B, and/or CCNB2 to identify a malignant adrenocortical cell proliferative disorder.

11. The method of claim 10, wherein the detecting methylation comprises detecting methylation within any two of KCTD12, KIRREL, SYNGR1, NTNG2, RARRES2, SLC16A9, IL13RA2, HTR2B, and CCNB2, any three of KCTD12, KIRREL, SYNGR1, NTNG2, RARRES2, SLC16A9, IL13RA2, HTR2B, and CCNB2, any four of KCTD12, KIRREL, SYNGR1, NTNG2, RARRES2, SLC16A9, IL13RA2, HTR2B, and CCNB2, any five of KCTD12, KIRREL, SYNGR1, NTNG2, RARRES2, SLC16A9, IL13RA2, HTR2B, and CCNB2, any six of KCTD12, KIRREL, SYNGR1, NTNG2, RARRES2, SLC16A9, IL13RA2, HTR2B, and CCNB2, any seven of KCTD12, KIRREL, SYNGR1, NTNG2, RARRES2, SLC16A9, IL13RA2, HTR2B, and CCNB2, any eight of KCTD12, KIRREL, SYNGR1, NTNG2, RARRES2, SLC16A9, IL13RA2, HTR2B, and CCNB2, or all nine.

12. The method of claim 10, wherein the reagent is a nucleic acid probe.

13. The method of claim 10, wherein the method is used to distinguish a primary malignant adrenocortical cell proliferative disorder from a benign adrenocortical cell proliferative disorder.

14. The method of claim 13, wherein the benign adrenocortical cell proliferative disorder is a benign adrenocortical tumor.

15. The method of claim 10, wherein the sample comprises adrenocortical tissue.

16. The method of claim 10, wherein the one or more malignant adrenocortical tumor-related nucleic acid comprise at least KCTD12, KIRREL, SYNGR1, NTNG2, RARRES2, SLC16A9, IL13RA2, HTR2B, and CCNB2.

* * * * *

SEQUENCE LISTING

```
<160> NUMBER OF SEQ ID NOS: 77

<210> SEQ ID NO 1
<211> LENGTH: 50
<212> TYPE: DNA
<213> ORGANISM: Homo sapiens

<400> SEQUENCE: 1
tcttactaat tcacaataaa attataatat catccatctc cataacaacc            50

<210> SEQ ID NO 2
<211> LENGTH: 50
<212> TYPE: DNA
<213> ORGANISM: Homo sapiens

<400> SEQUENCE: 2
attacaccca caaaaaaaac ccatatcctc ttttaccaaa ttaataaaac            50

<210> SEQ ID NO 3
<211> LENGTH: 50
<212> TYPE: DNA
<213> ORGANISM: Homo sapiens

<400> SEQUENCE: 3
cataaattaa aaaatccatt aaaaaaccct aaaattaaaa accccactac            50

<210> SEQ ID NO 4
<211> LENGTH: 50
<212> TYPE: DNA
<213> ORGANISM: Homo sapiens

<400> SEQUENCE: 4
aaataaaaaa acctaaaaat aacccttttct ccaaattaac cttaaaatcc            50

<210> SEQ ID NO 5
<211> LENGTH: 50
<212> TYPE: DNA
<213> ORGANISM: Homo sapiens
```

```
<400> SEQUENCE: 5
actacaactt aaattccaac ctcacaaata ttccaactaa aaaaaactac      50

<210> SEQ ID NO 6
<211> LENGTH: 50
<212> TYPE: DNA
<213> ORGANISM: Homo sapiens

<400> SEQUENCE: 6
taactatacc taaaacctac taacctacat aacctcttac tcctaaactc      50

<210> SEQ ID NO 7
<211> LENGTH: 50
<212> TYPE: DNA
<213> ORGANISM: Homo sapiens

<400> SEQUENCE: 7
accaacccaa caaaatccca acttacaaca aacaaacaat tcactctacc      50

<210> SEQ ID NO 8
<211> LENGTH: 50
<212> TYPE: DNA
<213> ORGANISM: Homo sapiens

<400> SEQUENCE: 8
acctacaatt ttaacaaaat tccctaccca crctaaaaat caatcaattc      50

<210> SEQ ID NO 9
<211> LENGTH: 50
<212> TYPE: DNA
<213> ORGANISM: Homo sapiens

<400> SEQUENCE: 9
taaatcrata taccctaaca atttcttata tttaaattaa cttcaacttc      50

<210> SEQ ID NO 10
<211> LENGTH: 50
<212> TYPE: DNA
<213> ORGANISM: Homo sapiens

<400> SEQUENCE: 10
aaaatatttc cctctattta tcatacaaat atatcaatct cctcttctac      50

<210> SEQ ID NO 11
<211> LENGTH: 50
<212> TYPE: DNA
<213> ORGANISM: Homo sapiens

<400> SEQUENCE: 11
acttaaaata acacttaaca attacttaac accctaaaat attaataaac      50

<210> SEQ ID NO 12
<211> LENGTH: 50
<212> TYPE: DNA
<213> ORGANISM: Homo sapiens

<400> SEQUENCE: 12
acttaaaata acacttaaca attacttaac accctaaaat attaataaac      50

<210> SEQ ID NO 13
<211> LENGTH: 50
<212> TYPE: DNA
<213> ORGANISM: Homo sapiens
```

```
<400> SEQUENCE: 13
ccccacaaaa aatcaaaaaa aacctaaaac aacaacaaaa aaattaaaca                50

<210> SEQ ID NO 14
<211> LENGTH: 50
<212> TYPE: DNA
<213> ORGANISM: Homo sapiens

<400> SEQUENCE: 14
aaataaatac caaccacaaa aacaccacct aaactccctc aaactaatca                50

<210> SEQ ID NO 15
<211> LENGTH: 50
<212> TYPE: DNA
<213> ORGANISM: Homo sapiens

<400> SEQUENCE: 15
acaaaccaaa accaaataaa caaaaatcaa aaaaaactac ctaaaacaca                50

<210> SEQ ID NO 16
<211> LENGTH: 50
<212> TYPE: DNA
<213> ORGANISM: Homo sapiens

<400> SEQUENCE: 16
ctttcrcctc tacctctata tacctctaaa ctataaactt taatttacac                50

<210> SEQ ID NO 17
<211> LENGTH: 50
<212> TYPE: DNA
<213> ORGANISM: Homo sapiens

<400> SEQUENCE: 17
cattcaaacc ttaacaacta acactctaca aaacaaacca aaaatataca                50

<210> SEQ ID NO 18
<211> LENGTH: 50
<212> TYPE: DNA
<213> ORGANISM: Homo sapiens

<400> SEQUENCE: 18
taaccrtaca aactaaaact tacaacccaa aaacacacaa aaacaaaaac                50

<210> SEQ ID NO 19
<211> LENGTH: 50
<212> TYPE: DNA
<213> ORGANISM: Homo sapiens

<400> SEQUENCE: 19
tataaacaat ttaaaaacaa ataaaacaaa cttataattt ccactaactc                50

<210> SEQ ID NO 20
<211> LENGTH: 50
<212> TYPE: DNA
<213> ORGANISM: Homo sapiens

<400> SEQUENCE: 20
aaaaaaaaac aattaaaaca aacaatcrct caaataccaa caccaaattc                50

<210> SEQ ID NO 21
<211> LENGTH: 50
<212> TYPE: DNA
```

<213> ORGANISM: Homo sapiens

<400> SEQUENCE: 21
acaaccacaa aaatatacca cattaaaaaa actaacaata cctaatatcc        50

<210> SEQ ID NO 22
<211> LENGTH: 50
<212> TYPE: DNA
<213> ORGANISM: Homo sapiens

<400> SEQUENCE: 22
craaattaat ccctaaaatc aaaattccct tactttaaaa cataataacc        50

<210> SEQ ID NO 23
<211> LENGTH: 50
<212> TYPE: DNA
<213> ORGANISM: Homo sapiens

<400> SEQUENCE: 23
tcctcraatt accatcacca atttcttacc tatcttacca aaattattac        50

<210> SEQ ID NO 24
<211> LENGTH: 50
<212> TYPE: DNA
<213> ORGANISM: Homo sapiens

<400> SEQUENCE: 24
aaataaaaat ataatttata tattcttaaa ttaaacattt tccccaattc        50

<210> SEQ ID NO 25
<211> LENGTH: 50
<212> TYPE: DNA
<213> ORGANISM: Homo sapiens

<400> SEQUENCE: 25
tatataaaca acgtatccaa accacgaatc taaataccta accgaacccg        50

<210> SEQ ID NO 26
<211> LENGTH: 50
<212> TYPE: DNA
<213> ORGANISM: Homo sapiens

<400> SEQUENCE: 26
ccccacaaaa aatcaaaaaa aacctaaaac gacaacgaaa aaattaaacg        50

<210> SEQ ID NO 27
<211> LENGTH: 50
<212> TYPE: DNA
<213> ORGANISM: Homo sapiens

<400> SEQUENCE: 27
aaataaatac cgaccgcaaa aacaccacct aaactccctc aaactaatcg        50

<210> SEQ ID NO 28
<211> LENGTH: 50
<212> TYPE: DNA
<213> ORGANISM: Homo sapiens

<400> SEQUENCE: 28
acaaaccaaa accgaataaa cgaaaatcga aaaaaactac ctaaaacgcg        50

<210> SEQ ID NO 29
<211> LENGTH: 50

```
<212> TYPE: DNA
<213> ORGANISM: Homo sapiens

<400> SEQUENCE: 29
cgttcaaacc ttaacaacta acgctctaca aaacgaacca aaaatatacg                50

<210> SEQ ID NO 30
<211> LENGTH: 122
<212> TYPE: DNA
<213> ORGANISM: Homo sapiens

<400> SEQUENCE: 30
cacgagagtg ttcttactgg ttcacaatgg agttatgata tcatccatct ccatagcaac    60
cgtctcccct agcaacacat aaaacacagt caaatactct tttctgaggg gaaaaaaga   120 aa                                                                  122

<210> SEQ ID NO 31
<211> LENGTH: 122
<212> TYPE: DNA
<213> ORGANISM: Homo sapiens

<400> SEQUENCE: 31
actgaagttc agcagtgatg gagctgtggt tgaggtgtct ggaggagacc atgaggtctg    60
cgtttcacta acctggtaaa agaggatatg ggttttttt gtgggtgtaa tagtgacatt   120
ta                                                                  122

<210> SEQ ID NO 32
<211> LENGTH: 122
<212> TYPE: DNA
<213> ORGANISM: Homo sapiens

<400> SEQUENCE: 32
accagccact ctcacaacct tgggctcagg ctgagccact ccacctctaa ggaggctctt    60
cgcagtgggg tctctaacct cagggcttct taatggacct cccaattcat gcatgcacac   120
cc                                                                  122

<210> SEQ ID NO 33
<211> LENGTH: 122
<212> TYPE: DNA
<213> ORGANISM: Homo sapiens

<400> SEQUENCE: 33
acgctgggca caggtgaagg agcctggaaa tggcccttc tccaaattga ccttagggtc    60
cgcctggccc tctccgttcc ctcccaccct gcccgcgctg ttccctgggg cctgcagttt   120
ta                                                                  122

<210> SEQ ID NO 34
<211> LENGTH: 122
<212> TYPE: DNA
<213> ORGANISM: Homo sapiens

<400> SEQUENCE: 34
gcagcttgtc tgctgcagct taaattccag cctcacaaat attccagctg ggaagggctg    60
cggacagaca ggcaggcaga ggatggccgg tagccagctg agggtgcaga gcaagccctg   120
gt                                                                  122

<210> SEQ ID NO 35
```

<211> LENGTH: 122
<212> TYPE: DNA
<213> ORGANISM: Homo sapiens

<400> SEQUENCE: 35

```
gcatcatgag ggtgggagcc agggctgccc atcatgggac cagatcccca actaggccct    60
cgagcccagg agcaagaggt catgcaggcc agcaggtttc aggcacagcc accctagaat   120
gt                                                                  122
```

<210> SEQ ID NO 36
<211> LENGTH: 122
<212> TYPE: DNA
<213> ORGANISM: Homo sapiens

<400> SEQUENCE: 36

```
aaggcattac ggttagaaac tggccaggtg tcatttttga gagattagat aactgttttc    60
cggtagagtg aattgcctgt ttgttgcaag ttgggacttt gctgggctgg tttacagggc   120
ca                                                                  122
```

<210> SEQ ID NO 37
<211> LENGTH: 122
<212> TYPE: DNA
<213> ORGANISM: Homo sapiens

<400> SEQUENCE: 37

```
tgttccctgg ggcctgcagt tttagcaaag ttccctgccc acgctaggaa tcagtcagtt    60
cgcactccca ccctacaccc ctaatcttgc ccattgtgtc tctccctggg tctccggcac   120
ga                                                                  122
```

<210> SEQ ID NO 38
<211> LENGTH: 122
<212> TYPE: DNA
<213> ORGANISM: Homo sapiens

<400> SEQUENCE: 38

```
ctcttcggaa tcttctctag cttcctcagc cctctgccta aacctgcctg aagaatttct    60
cgaagctgaa gccaactcaa atataagaaa ctgttagggc ataccgattt acagaatttg   120
at                                                                  122
```

<210> SEQ ID NO 39
<211> LENGTH: 122
<212> TYPE: DNA
<213> ORGANISM: Homo sapiens

<400> SEQUENCE: 39

```
acattccttc ctggccataa attggaccct cccattttca ggccctcttg tgtgagtcag    60
cgcagaagag gagactgata catttgcatg acaaatagag ggaaatattc tgtgccagta   120
tt                                                                  122
```

<210> SEQ ID NO 40
<211> LENGTH: 122
<212> TYPE: DNA
<213> ORGANISM: Homo sapiens

<400> SEQUENCE: 40

```
ggtgtagctt tacttagagt gacacttggc agttacttga caccctggaa tgttggtgga    60
cgtggcactg gtaaaatggc ggggggggggg ggaataaggg ggacaaagca gggttcaaga   120
```

| | |
|---|---|
| at | 122 |

<210> SEQ ID NO 41
<211> LENGTH: 122
<212> TYPE: DNA
<213> ORGANISM: Homo sapiens

<400> SEQUENCE: 41

| | |
|---|---|
| ctcagatgtc cggagactgg accctccgtg agccgcatgg acacacggtc ccgtgtcacc | 60 |
| cgggcccggc caggcaccca gatccgtggc ttggacacgc tgcccacaca ctcaggagcg | 120 |
| tc | 122 |

<210> SEQ ID NO 42
<211> LENGTH: 122
<212> TYPE: DNA
<213> ORGANISM: Homo sapiens

<400> SEQUENCE: 42

| | |
|---|---|
| agggatggcc accccacag ggagtcaggg agggcctggg gcgacagcgg aaaggttaag | 60 |
| cgtcgaaaag gtcaagtgct accgtggaga gatcatctga gggggaggct cccggtggga | 120 |
| ca | 122 |

<210> SEQ ID NO 43
<211> LENGTH: 122
<212> TYPE: DNA
<213> ORGANISM: Homo sapiens

<400> SEQUENCE: 43

| | |
|---|---|
| gggtcacagc ctgccgaagg cagccaggcc tgcagctctt ccccggcccc tctcggacag | 60 |
| cgaccagcct gagggagtcc aggtggtgcc cctgcggccg gcacccactc ctggcctagg | 120 |
| cc | 122 |

<210> SEQ ID NO 44
<211> LENGTH: 122
<212> TYPE: DNA
<213> ORGANISM: Homo sapiens

<400> SEQUENCE: 44

| | |
|---|---|
| cccagatccg tggcttggac acgctgccca cacactcagg agcgtctgcc gcgtaaccca | 60 |
| cgcgccccag gcagcttccc tcgaccccg cccactcggc cttggcctgc tgggtcacag | 120 |
| cc | 122 |

<210> SEQ ID NO 45
<211> LENGTH: 122
<212> TYPE: DNA
<213> ORGANISM: Homo sapiens

<400> SEQUENCE: 45

| | |
|---|---|
| tgcagattta actttcgcct ctgcctctgt gtgcctctgg gctgtaagct ttagtttgca | 60 |
| cggttaacgg ggatggcctc tcccatggtc ggttggagtg tgttgcacag cgtctggtcc | 120 |
| ag | 122 |

<210> SEQ ID NO 46
<211> LENGTH: 122
<212> TYPE: DNA
<213> ORGANISM: Homo sapiens

```
<400> SEQUENCE: 46
ctgctgagct gtcgttcagg ccttggcaac tgacgctctg cagaacggac caggagtgtg      60
cggtggtgga gtccggctgg cctgggttgc agatttaact ttcgcctctg cctctgtgtg     120
cc                                                                    122

<210> SEQ ID NO 47
<211> LENGTH: 122
<212> TYPE: DNA
<213> ORGANISM: Homo sapiens

<400> SEQUENCE: 47
gaacggacca ggagtgtgcg gtggtggagt ccggctggcc tgggttgcag atttaactttt     60 cgcctctgcc tctgtgtgcc tctgggctgt aagctttagt ttgcacggtt aacggggatg    120
gc                                                                    122

<210> SEQ ID NO 48
<211> LENGTH: 122
<212> TYPE: DNA
<213> ORGANISM: Homo sapiens

<400> SEQUENCE: 48
cctgttcatc ctgtgagcag tttagagaca gatgagacag gcttatggtt tccactggct     60
cggctccgtg cgtgtgcgga ttgggcttcc tgagagcctg gttagcccct tttatctgct    120
ct                                                                    122

<210> SEQ ID NO 49
<211> LENGTH: 122
<212> TYPE: DNA
<213> ORGANISM: Homo sapiens

<400> SEQUENCE: 49
gccctccctc cacctatttg gattagacca ggagactgca gcaaacttct caagggagg      60 cgaacttggt gttggtatct gagcgattgt ctgtttcaat tgtttccctc tgtcttggaa    120
aa                                                                    122

<210> SEQ ID NO 50
<211> LENGTH: 122
<212> TYPE: DNA
<213> ORGANISM: Homo sapiens

<400> SEQUENCE: 50
aactgtaaat tacaaccaca aggatatacc acattagaaa gactgacaat acctaatgtc     60
cggaaggctg tggcacaacc ataataactc ccatacttg ctagttggag tgtaaaatgg    120
ta                                                                    122

<210> SEQ ID NO 51
<211> LENGTH: 122
<212> TYPE: DNA
<213> ORGANISM: Homo sapiens

<400> SEQUENCE: 51
gtgatcccgc ccgcctcggc ctcccgaagt gctaggatta caggcgtgag ccaccgcgcc     60
cggccaccat gttttaaagt aagggaatcc tgatttcagg gattaatctc gtattgtcat    120
tg                                                                    122
```

```
<210> SEQ ID NO 52
<211> LENGTH: 122
<212> TYPE: DNA
<213> ORGANISM: Homo sapiens

<400> SEQUENCE: 52
tgttttaagc aaaaaaagaa aaaataatct atatatctct aggtgtactt gccaaagcac      60
cgtaataatt ctggtaagat aggcaagaaa ttggtgatgg taacccgagg agaaaaacag     120
ta                                                                   122

<210> SEQ ID NO 53
<211> LENGTH: 122
<212> TYPE: DNA
<213> ORGANISM: Homo sapiens

<400> SEQUENCE: 53
ttgtagaact tgagtaaaag tgtggtttgt atgttcttaa gttgagcatt ttccccaatt      60
cgcacacgtt ttactgtttt tttgttttttt tttttttttt tttttttttt gagacggagt   120
tt                                                                   122

<210> SEQ ID NO 54
<211> LENGTH: 50
<212> TYPE: DNA
<213> ORGANISM: Homo sapiens

<400> SEQUENCE: 54
cggttgctat ggagatggat gatatcataa ctccattgtg aaccagtaag                 50

<210> SEQ ID NO 55
<211> LENGTH: 50
<212> TYPE: DNA
<213> ORGANISM: Homo sapiens

<400> SEQUENCE: 55
ttacacccac aaaaaaaacc catatcctct tttaccaggt tagtgaaacg                 50

<210> SEQ ID NO 56
<211> LENGTH: 50
<212> TYPE: DNA
<213> ORGANISM: Homo sapiens

<400> SEQUENCE: 56
cgcagtgggg tctctaacct cagggcttct taatggacct cccaattcat                 50

<210> SEQ ID NO 57
<211> LENGTH: 50
<212> TYPE: DNA
<213> ORGANISM: Homo sapiens

<400> SEQUENCE: 57
ggtgaaggag cctggaaatg gccctttctc caaattgacc ttagggtccg                 50

<210> SEQ ID NO 58
<211> LENGTH: 50
<212> TYPE: DNA
<213> ORGANISM: Homo sapiens

<400> SEQUENCE: 58 cgcagcccttc cccagctgga atatttgtga ggctggaatt taagctgcag                50

<210> SEQ ID NO 59
```

```
<211> LENGTH: 50
<212> TYPE: DNA
<213> ORGANISM: Homo sapiens

<400> SEQUENCE: 59
ggctgtgcct gaaacctgct ggcctgcatg acctcttgct cctgggctcg            50

<210> SEQ ID NO 60
<211> LENGTH: 50
<212> TYPE: DNA
<213> ORGANISM: Homo sapiens

<400> SEQUENCE: 60
cggtagagtg aattgcctgt ttgttgcaag ttgggacttt gctgggctgg            50

<210> SEQ ID NO 61
<211> LENGTH: 50
<212> TYPE: DNA
<213> ORGANISM: Homo sapiens

<400> SEQUENCE: 61
cctgcagttt tagcaaagtt ccctgcccac gctaggaatc agtcagttcg            50

<210> SEQ ID NO 62
<211> LENGTH: 50
<212> TYPE: DNA
<213> ORGANISM: Homo sapiens

<400> SEQUENCE: 62
aaatcggtat gccctaacag tttcttatat ttgagttggc ttcagcttcg            50

<210> SEQ ID NO 63
<211> LENGTH: 50
<212> TYPE: DNA
<213> ORGANISM: Homo sapiens

<400> SEQUENCE: 63
gaatatttcc ctctatttgt catgcaaatg tatcagtctc ctcttctgcg            50

<210> SEQ ID NO 64
<211> LENGTH: 50
<212> TYPE: DNA
<213> ORGANISM: Homo sapiens

<400> SEQUENCE: 64
cttagagtga cacttggcag ttacttgaca ccctggaatg ttggtggacg            50

<210> SEQ ID NO 65
<211> LENGTH: 50
<212> TYPE: DNA
<213> ORGANISM: Homo sapiens

<400> SEQUENCE: 65
cgggcccggc caggcaccca gatccgtggc ttggacacgc tgcccacaca            50

<210> SEQ ID NO 66
<211> LENGTH: 50
<212> TYPE: DNA
<213> ORGANISM: Homo sapiens

<400> SEQUENCE: 66
cgcttaacct ttccgctgtc gccccaggcc ctccctgact ccctgtgggg            50
```

```
<210> SEQ ID NO 67
<211> LENGTH: 50
<212> TYPE: DNA
<213> ORGANISM: Homo sapiens

<400> SEQUENCE: 67
gagtgggtgc cggccgcagg ggcaccacct ggactccctc aggctggtcg            50

<210> SEQ ID NO 68
<211> LENGTH: 50
<212> TYPE: DNA
<213> ORGANISM: Homo sapiens

<400> SEQUENCE: 68
cgcgccccag gcagcttccc tcgaccccg cccactcggc cttggcctgc             50

<210> SEQ ID NO 69
<211> LENGTH: 50
<212> TYPE: DNA
<213> ORGANISM: Homo sapiens

<400> SEQUENCE: 69
tttcgcctct gcctctgtgt gcctctgggc tgtaagcttt agtttgcacg            50

<210> SEQ ID NO 70
<211> LENGTH: 50
<212> TYPE: DNA
<213> ORGANISM: Homo sapiens

<400> SEQUENCE: 70
cgttcaggcc ttggcaactg acgctctgca gaacggacca ggagtgtgcg            50

<210> SEQ ID NO 71
<211> LENGTH: 50
<212> TYPE: DNA
<213> ORGANISM: Homo sapiens

<400> SEQUENCE: 71
cgcctctgcc tctgtgtgcc tctgggctgt aagctttagt ttgcacggtt            50

<210> SEQ ID NO 72
<211> LENGTH: 50
<212> TYPE: DNA
<213> ORGANISM: Homo sapiens

<400> SEQUENCE: 72
gtgagcagtt tagagacaga tgagacaggc ttatggtttc cactggctcg            50

<210> SEQ ID NO 73
<211> LENGTH: 50
<212> TYPE: DNA
<213> ORGANISM: Homo sapiens

<400> SEQUENCE: 73
gagggaaaca attgaaacag acaatcgctc agataccaac accaagttcg            50

<210> SEQ ID NO 74
<211> LENGTH: 50
<212> TYPE: DNA
<213> ORGANISM: Homo sapiens

<400> SEQUENCE: 74
cggacattag gtattgtcag tctttctaat gtggtatatc cttgtggttg            50
```

-continued

```
<210> SEQ ID NO 75
<211> LENGTH: 50
<212> TYPE: DNA
<213> ORGANISM: Homo sapiens

<400> SEQUENCE: 75
gagattaatc cctgaaatca ggattccctt actttaaaac atggtggccg            50

<210> SEQ ID NO 76
<211> LENGTH: 50
<212> TYPE: DNA
<213> ORGANISM: Homo sapiens

<400> SEQUENCE: 76
cctcgggtta ccatcaccaa tttcttgcct atcttaccag aattattacg            50

<210> SEQ ID NO 77
<211> LENGTH: 50
<212> TYPE: DNA
<213> ORGANISM: Homo sapiens

<400> SEQUENCE: 77
agtaaaagtg tggtttgtat gttcttaagt tgagcatttt ccccaattcg            50
```